United States Patent
Andrews et al.

(10) Patent No.: US 10,485,852 B2
(45) Date of Patent: *Nov. 26, 2019

(54) ENHANCING HEALTH IN MAMMALS USING TELOMERASE REVERSE TRANSCRIPTASE GENE THERAPY

(71) Applicant: Sierra Sciences, LLC, Reno, NV (US)

(72) Inventors: William H. Andrews, Reno, NV (US); Lancer K. Brown, Sparks, NV (US); Hamid Mohammadpour, Reno, NV (US); Laura A. Briggs, Reno, NV (US)

(73) Assignee: Sierra Sciences, LLC, Reno, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/994,421

(22) Filed: May 31, 2018

(65) Prior Publication Data
US 2018/0344816 A1  Dec. 6, 2018

Related U.S. Application Data

(63) Continuation of application No. 15/220,250, filed on Jul. 26, 2016, which is a continuation of application No. 14/655,140, filed as application No. PCT/US2013/077619 on Dec. 23, 2013, now Pat. No. 9,453,209.

(60) Provisional application No. 61/746,438, filed on Dec. 27, 2012.

(51) Int. Cl.
| | |
|---|---|
| *C07H 21/04* | (2006.01) |
| *A61K 38/45* | (2006.01) |
| *C12N 9/12* | (2006.01) |
| *C12N 7/00* | (2006.01) |
| *A61K 48/00* | (2006.01) |
| *A61K 38/00* | (2006.01) |

(52) U.S. Cl.
CPC .............. *A61K 38/45* (2013.01); *A61K 48/00* (2013.01); *A61K 48/005* (2013.01); *A61K 48/0066* (2013.01); *C12N 7/00* (2013.01); *C12N 9/1276* (2013.01); *C12Y 207/07049* (2013.01); *A61K 38/00* (2013.01); *C12N 2710/10341* (2013.01); *C12N 2740/15041* (2013.01); *C12N 2750/14143* (2013.01)

(58) Field of Classification Search
CPC .................................................... C07H 21/04
See application file for complete search history.

(56) References Cited

U.S. PATENT DOCUMENTS

| | | |
|---|---|---|
| 6,475,789 B1 | 11/2002 | Cech et al. |
| 2009/0175892 A1 | 7/2009 | Langlade-Demoyen et al. |

FOREIGN PATENT DOCUMENTS

| | | |
|---|---|---|
| WO | WO0216555 A2 | 2/2002 |
| WO | WO0216657 A1 | 2/2002 |
| WO | WO0216658 A1 | 2/2002 |
| WO | WO02070668 A2 | 9/2002 |
| WO | WO02072787 A2 | 9/2002 |
| WO | WO02090570 A2 | 11/2002 |
| WO | WO02090571 A2 | 11/2002 |
| WO | WO02101010 A2 | 12/2002 |
| WO | WO03000916 A2 | 1/2003 |
| WO | WO03016474 A2 | 2/2003 |
| WO | WO03034985 A2 | 5/2003 |
| WO | WO2012001170 A1 | 1/2012 |

OTHER PUBLICATIONS

Harley, Calvin B. (Telomerase and cancer therapeutics. Nature Reviews Cancer 8.3 (2008): 167).*
Cristofari et al., Telomere length homeostasis requires that telomerase levels are limiting, The EMBO Journal (2006) 25:565-574.
De Jesus et al., Telomerase gene therapy in adult and old mice delays aging and increases longevity without increasing cancer, EMBO Mol Med (2012) 4(8): 691-704.
Vidale et al., The catalytic and the RNA subunits of human telomerase are required to immortalize equid primary fibroblasts, Chromosoma (2012) 121:475-488.
Sinn et al., Gene therapy progress and prospects: development of improved lentiviral and retroviral vectors—design, biosafety, and production, Gene Ther. Jul. 2005;12(14):1089-98.
Yamaguchi et al., Mutations in TERT, the gene for telomerase reverse transcriptase, in aplastic anemia, N Engl J Med. Apr. 7, 2005;352(14):1413-24.
Bachand et al., Expression of hTERT and hTR in cis reconstitutes and active human telomerase ribonucleoprotein, RNA. May 2000;6(5):778-84.
Li et al., Expression and suppression of human telomerase RNA, Cold Spring Harb Symp Quant Biol. 2006;71:211-5.
Prel et al., Highly efficient in vitro and in vivo delivery of functional RNAs using new versatile MS2-chimeric retrovirus-like particle, Mol Ther Methods Clin Dev. Oct. 21, 2015;2:15039.
Shaw et al., Design and Potential of Non-Integrating Lentiviral Vectors, Biomedicines. Mar. 2014; 2(1): 14-35.
Chen et al., Episomal lentiviral vectors confer erythropoietin expression in dividing cells, Plasmid. Mar. 2017;90:15-19.
Delluc-Clavieres et al., Efficient gene transfer in skeletal muscle with AAV-derived bicistronic vector using the FGF-1 IRES, Gene Ther. Aug. 2008;15(15):1090-8.

* cited by examiner

*Primary Examiner* — Kimberly Chong
(74) *Attorney, Agent, or Firm* — Bret E. Field; Bozicevic, Field & Francis LLP

(57) ABSTRACT

Methods of treating an age-related disorder in a subject are provided. Aspects of the methods include administering to the subject a nucleic acid vector including a coding sequence for telomerase reverse transcriptase (TERT) and/or telomerase RNA (TR). Gene therapy methods are also provided. Aspects of the invention further include compositions, e.g., nucleic acid vectors and kits, etc., that find use in methods of the invention.

20 Claims, 7 Drawing Sheets

Specification includes a Sequence Listing.

SEQUENCE LISTING

<160> NUMBER OF SEQ ID NOS: 3

<210> SEQ ID NO 1
<211> LENGTH: 38420
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (761)..(761)
<223> OTHER INFORMATION: n is a, c, g, or t
<220> FEATURE:
<221> NAME/KEY: misc_feature
<222> LOCATION: (2450)..(2450)
<223> OTHER INFORMATION: n is a, c, g, or t

<400> SEQUENCE: 1

| | | | | | |
|---|---|---|---|---|---|
| tcacagaacc | ctagtattca | acctgccacc | tccctcccaa | cacacagagt | acacagtcct       60 |
| ttctccccgg | ctggccttaa | aaagcatcat | atcatgggta | acagacatat | tcttaggtgt      120 |
| tatattccac | acggtttcct | gtcgagccaa | acgctcatca | agtgatatta | ataaactccc      180 |
| cgggcagctc | acttaagttc | atgtcgctgt | ccagctgctg | agccacaggc | tgctgtccaa      240 |
| cttgcggttg | cttaacgggc | ggcgaaggag | aagtccacgc | ctacatgggg | ggagagtcat      300 |
| aatcgtgcat | caggatagggg | cggtggtgct | gcagcagcgc | gcgaataaac | tgctgccgcc      360 |
| gccgctccgt | cctgcaggaa | tacaacatgg | cagtggtctc | ctcagcgatg | attcgcaccg      420 |
| cccgcagcat | aaggcgcttg | tcctccgggc | acagcagcgc | accctgatct | cacttaaatc      480 |
| agcacagtaa | ctgcagcaca | gcaccacaat | attgttcaaa | atcccacagt | gcaaggcgct      540 |
| gtatccaaag | ctcatggcgg | ggaccacaga | acccacgtgg | ccatcatacc | acaagcgcag      600 |
| gtagattaag | tggcgacccc | tcataaacac | gctggacata | aacattacct | cttttggcat      660 |
| gttgtaattc | accacctccc | ggtaccatat | aaacctctga | ttaaacatgg | cgccatccac      720 |
| caccatccta | aaccagctgg | ccaaaacctg | ccccgccggg | ntatacactg | cagggaaccg      780 |
| ggacttggac | aatgacaagt | gggagagccc | aggactcgta | accatggatc | atcatgctcg      840 |
| tcatgatatc | aatgttggca | caacacaggc | acacgtgcat | acacttcctc | aggattacaa      900 |
| gctcctcccg | cgttagaacc | atatcccagg | gaacaaccca | ttcctgaatc | agcgtaaatc      960 |
| ccacactgca | gggaagacct | cgcacgtaac | tcacgttgtg | cattgtcaaa | gtgttacatt     1020 |
| cgggcagcag | cggatgatcc | tccagtatgg | tagcgcgggt | ttctgtctca | aaaggaggta     1080 |
| gacgatccct | actgtacgga | gtgcgccgag | acaaccgaga | tcgtgttggt | cgtagtgtca     1140 |
| tgccaaatgg | aacgccggac | gtagtcatat | ttcctgaagc | aaaaccaggt | gcgggcgtga     1200 |
| caaacagatc | tgcgtctccg | gtctcgccgc | ttagatcgct | ctgtgtagta | gttgtagtat     1260 |
| atccactctc | tcaaagcatc | caggcgcccc | ctggcttcgg | gttctatgta | aactccttca     1320 |
| tgcgccgctg | ccctgataac | atccaccacc | gcagaataag | ccacacccag | ccaacctaca     1380 |
| cattcgttct | gcgagtcaca | cacgggagga | gcgggaagag | ctggaagaac | catgtttttt     1440 |
| tttttattcc | aaaagattat | ccaaaacctc | aaaatgaaga | tctattaagt | gaacgcgctc     1500 |
| ccctccggtg | gcgtggtcaa | actctacagc | caaagaacag | ataatggcat | ttgtaagatg     1560 |
| ttgcacaatg | gcttccaaaa | ggcaaacggc | cctcacgtcc | aagtggacgt | aaaggctaaa     1620 |

```
cccttcaggg tgaatctcct ctataaacat tccagcacct tcaaccatgc ccaaataatt    1680
ctcatctcgc caccttctca atatatctct aagcaaatcc cgaatattta agtccgggcc    1740
attgtaaaaa atttggctcc agagcgccct ccaccttcag cctcaagcag cgaatcatga    1800
ttgcaaaaat tcaggttcct cacagacctg tataagattc aaaagcggaa cattaacaaa    1860
aataccgcga tcccgtaggt cccttcgcag ggccagctga acataatcgt gcaggtctgc    1920
acggaccagc gcggccactt ccccgccagg aaccatgaca aaagaaccca cactgattat    1980
gacacgcata ctcggagcta tgctaaccag cgtagccccg atgtaagctt gttgcatggg    2040
cggcgatata aaatgcaagg tgctgctcaa aaaatcaggc aaagcctcgc gcaaaaaaga    2100
aagcacatcg tagtcatgct catgcagata aaggcaggta agctccggaa ccaccacaga    2160
aaaagacacc attttctct  caaacatgtc tgcgggtttc tgcataaaca caaaataaaa    2220
taacaaaaaa acatttaaac attagaagcc tgtcttacaa caggaaaaac aacccttata    2280
agcataagac ggactacggc catgccggcg tgaccgtaaa aaaactggtc accgtgatta    2340
aaaagcacca ccgacagctc ctcggtcagt ccggagtcat aatgtaagac tcggtaaaca    2400
catcaggttg attcacatcg gtcagtgtta aaaagcgacc gaaatagccn ggggaatac    2460 aataccgca  ggcgtagaga caacattaca gcccccatag gaggtataac aaaattaata    2520
ggagagaaaa acacataaac acctgaaaaa ccctcctgcc taggcaaaat agcaccctcc    2580
cgctccagaa caacatacag cgcttccaca gcggcagcca taacagtcag ccttaccagt    2640 aaaaagaaa  acctattaaa aaaacaccac tcgacacggc accagctcaa tcagtcacag    2700
tgtaaaaaag ggccaagtgc agagcgagta tatataggac taaaaaatga cggtaacggt    2760
taaagtccac aaaaaacacc cagaaaaccg cacgcgaacc tacgcccaga acgaaagcc     2820 aaaaaaccca caacttcctc aaatcgtcac ttccgttttc ccacgttacg tcacttccca    2880
ttttaagaaa actacaattc ccaacacata caagttactc cgccctaaaa cctacgtcac    2940
ccgccccgtt cccacgcccc gcgccacgtc acaaactcca cccccctcatt atcatattgg    3000 cttcaatcca aaataaggta tattattgat gatgttaatt aacatgcatg gatccatatg    3060
cggtgtgaaa taccgcacag atgcgtaagg agaaaatacc gcatcaggcg ctcttccgct    3120
tcctcgctca ctgactcgct gcgctcggtc gttcggctgc ggcgagcggt atcagctcac    3180
tcaaaggcgg taatacggtt atccacagaa tcagggggata acgcaggaaa gaacatgtga    3240
gcaaaaggcc agcaaaaggc caggaaccgt aaaaaggccg cgttgctggc gttttccat     3300 aggctccgcc cccctgacga gcatcacaaa aatcgacgct caagtcagag gtggcgaaac    3360
ccgacaggac tataaagata ccaggcgttt cccccctggaa gctccctcgt gcgctctcct    3420
gttccgaccc tgccgcttac cggatacctg tccgcctttc tcccttcggg aagcgtggcg    3480
ctttctcata gctcacgctg taggtatctc agttcggtgt aggtcgttcg ctccaagctg    3540
ggctgtgtgc acgaaccccc cgttcagccc gaccgctgcg ccttatccgg taactatcgt    3600
cttgagtcca acccggtaag acacgactta tcgccactgg cagcagccac tggtaacagg    3660
attagcagag cgaggtatgt aggcggtgct acagagttct tgaagtggtg gcctaactac    3720
ggctacacta aaggacagt  atttggtatc tgcgctctgc tgaagccagt taccttcgga    3780
aaaagagttg gtagctcttg atccggcaaa caaaccaccg ctggtagcgg tggttttttt    3840
gtttgcaagc agcagattac gcgcagaaaa aaaggatctc aagaagatcc tttgatcttt    3900
tctacggggt ctgacgctca gtggaacgaa aactcacgtt aagggatttt ggtcatgaga    3960
```

```
ttatcaaaaa ggatcttcac ctagatcctt ttaaattaaa aatgaagttt taaatcaatc    4020
taaagtatat atgagtaaac ttggtctgac agttaccaat gcttaatcag tgaggcacct    4080
atctcagcga tctgtctatt tcgttcatcc atagttgcct gactcccgt cgtgtagata     4140 actacgatac gggagggctt accatctggc cccagtgctg caatgatacc gcgagaccca    4200
cgctcaccgg ctccagattt atcagcaata aaccagccag ccggaagggc cgagcgcaga    4260
agtggtcctg caactttatc cgcctccatc cagtctatta attgttgccg ggaagctaga    4320
gtaagtagtt cgccagttaa tagtttgcgc aacgttgttg ccattgctgc agccatgaga    4380
ttatcaaaaa ggatcttcac ctagatcctt ttcacgtaga aagccagtcc gcagaaacgg    4440
tgctgacccc ggatgaatgt cagctactgg gctatctgga caagggaaaa cgcaagcgca    4500
aagagaaagc aggtagcttg cagtgggctt acatggcgat agctagactg ggcggtttta    4560
tggacagcaa gcgaaccgga attgccagct ggggcgccct ctggtaaggt tgggaagccc    4620
tgcaaagtaa actggatggc tttcttgccg ccaaggatct gatggcgcag ggatcaagc     4680 tctgatcaag agacaggatg aggatcgttt cgcatgattg aacaagatgg attgcacgca    4740
ggttctccgg ccgcttgggt ggagaggcta ttcggctatg actgggcaca acagacaatc    4800
ggctgctctg atgccgccgt gttccggctg tcagcgcagg ggcgcccggt tcttttgtc     4860 aagaccgacc tgtccggtgc cctgaatgaa ctgcaagacg aggcagcgcg gctatcgtgg    4920
ctggccacga cgggcgttcc ttgcgcagct gtgctcgacg ttgtcactga agcgggaagg    4980
gactggctgc tattgggcga agtgccgggg caggatctcc tgtcatctca ccttgctcct    5040
gccgagaaag tatccatcat ggctgatgca atgcggcggc tgcatacgct tgatccggct    5100
acctgcccat tcgaccacca agcgaaacat cgcatcgagc gagcacgtac tcggatggaa    5160
gccggtcttg tcgatcagga tgatctggac gaagagcatc aggggctcgc gccagccgaa    5220
ctgttcgcca ggctcaaggc gagcatgccc gacggcgagg atctcgtcgt gacccatggc    5280
gatgcctgct tgccgaatat catggtggaa aatggccgct tttctggatt catcgactgt    5340
ggccggctgg gtgtggcgga ccgctatcag gacatagcgt tggctacccg tgatattgct    5400
gaagagcttg gcggcgaatg ggctgaccgc ttcctcgtgc tttacggtat cgccgctccc    5460
gattcgcagc gcatcgcctt ctatcgcctt cttgacgagt tcttctgaat tttgttaaaa    5520 ttttgttaa atcagctcat tttttaacca ataggccgaa atcggcaaca tcccttataa    5580
atcaaaagaa tagaccgcga tagggttgag tgttgttcca gtttggaaca agagtccact    5640
attaaagaac gtggactcca acgtcaaagg gcgaaaaacc gtctatcagg gcgatggccc    5700
actacgtgaa ccatcaccca atcaagtttt ttgcggtcg aggtgccgta aagctctaaa     5760
tcggaaccct aaagggagcc ccgatttag agcttgacgg ggaaagccgg cgaacgtggc     5820
gagaaaggaa gggaagaaag cgaaaggagc gggcgctagg gcgctggcaa gtgtagcggt    5880
cacgctgcgc gtaaccacca cacccgcgcg cttaatgcgc cgctacaggg cgcgtccatt    5940
cgccattcag gatcgaatta attcttaatt aacatcatca ataatatacc ttattttgga    6000
ttgaagccaa tatgataatg agggggtgga gtttgtgacg tggcgcgggg cgtgggaacg    6060
gggcgggtga cgtagtagtg tggcggaagt gtgatgttgc aagtgtggcg aacacatgt     6120 aagcgacgga tgtggcaaaa gtgacgtttt tggtgtgcgc cggtgtacac aggaagtgac    6180
aattttcgcg cggttttagg cggatgttgt agtaaatttg ggcgtaaccg agtaagattt    6240
ggccattttc gcgggaaaac tgaataagag gaagtgaaat ctgaataatt ttgtgttact    6300
catagcgcgt aatactggta ccgcggccgc ctcgagtcta gagatatcga attcaagctt    6360
```

```
aaggtgcacg gcccacgtgg ccactagtaa ttttctgca gaaaacgtac ccggggatcc      6420
tctaggatcc caccgaaagg ttgctcctta acacaggcta aggaccagct tctttgggag      6480
agaacagacg caggggcggg agggaaaaag ggagaggcag acgtcacttc cccttggcgg      6540
ctctggcagc agattggtcg gttgagtggc agaaaggcag acggggactg ggcaaggcac      6600
tgtcggtgac atcacggaca gggcgacttc tatgtagatg aggcagcgca gaggctgctg      6660
cttcgccact tgctgcttcg ccacgaagga gttcccgtgc cctgggagcg ggttcaggac      6720
cgcggatcgg aagtgagaat cccagctgtg tgtcagggct ggaaagggct cgggagtgcg      6780
cggggcaagt gaccgtgtgt gtaaagagtg aggcgtatga ggctgtgtcg gggcagagcc      6840
cgaagatccg ggttgcggag ggtgggcctg ggaggggtgg tggccatttt ttgtctaacc      6900
ctaactgaga agggcgtagg cgccgtgctt ttgctcccg cgcgctgttt ttctcgctga      6960 cttttcagcgg gcggaaaagc ctcggcctgc cgccttccac cgttcattct agagcaaaca      7020
aaaaatgtca gctgctggcc cgttcgcccc tcccggggac ctgcggcggg tcgcctgccc      7080
agcccccgaa ccccgcctgg aggccgcggt cggcccgggg cttctccgga ggcacccact      7140
gccaccgcga agagttgggc tctgtcagcc gcgggtctct cggggcgag ggcgaggttc      7200 aggcctttca ggccgcagga agaggaacgg agcgagtccc cgcgcgcggc gcgattccct      7260
gagctgtggg acgtgcaccc aggactcggc tcacacatgc agttcgcttt cctgttggtg      7320
gggggaacgc cgatcgtgcg catccgtcac ccctcgccgg caatgggggc ttgtgaaccc      7380
ccaaacctga ctgactgggc cagtgtgctg caaattggca ggagacgtga aggcacctcc      7440
aaagtcgact ttctggagtt tcaaaaacag accgtacgat gcattagtta ttaatagtaa      7500
tcaattacgg ggtcattagt tcatagccca tatgtgagt tccgcgttac ataacttacg      7560
gtaaatggcc cgcctggctg accgcccaac gaccccgcc cattgacgtc aataatgacg      7620
tatgttccca tagtaacgcc aatagggact ttccattgac gtcaatgggt ggagtattta      7680
cggtaaactg cccacttggc agtacatcaa gtgtatcata tgccaagtac gccccctatt      7740
gacgtcaatg acggtaaatg gcccgcctgg cattatgccc agtacatgac cttatgggac      7800
tttcctactt ggcagtacat ctacgtatta gtcatcgcta ttaccatggt gatgcggttt      7860
tggcagtaca tcaatgggcg tggatagcgg tttgactcac ggggatttcc aagtctccac      7920
cccattgacg tcaatgggag tttgttttgg caccaaaatc aacgggactt tccaaaatgt      7980
cgtaacaact ccgccccatt gacgcaaatg ggcggtaggc gtgtacggtg ggaggtctat      8040
ataagcagag ctggtttagt gaaccgtcag atccgctagc ccaccatgc cgcgcgctcc      8100 ccgctgccga gccgtgcgct ccctgctgcg cagccactac cgcgaggtgc tgccgctggc      8160
cacgttcgtg cggcgcctgg ggcccaggg ctggcggctg gtgcagcgcg ggacccggc      8220 ggctttccgc gcgctggtgg cccagtgcct ggtgtgcgtg ccctgggacg cacggccgcc      8280
ccccgccgcc ccctccttcc gccaggtgtc ctgcctgaag gagctggtgg cccgagtgct      8340
gcagaggctg tgcgagcgcg gcgcgaagaa cgtgctggcc ttcggcttcg cgctgctgga      8400
cggggcccgc gggggccccc ccgaggcctt caccaccagc gtgcgcagct acctgcccaa      8460
cacggtgacc gacgcactgc gggggagcgg ggcgtggggg ctgctgttgc gccgcgtggg      8520
cgacgacgtg ctggttcacc tgctggcacg ctgcgcgctc tttgtgctgg tggctcccag      8580
ctgcgcctac caggtgtgcg ggcgccgcct gtaccagctc ggcgctgcca tcaggcccg      8640 gcccccgcca cacgctagtg gaccccgaag gcgtctggga tgcgaacggg cctggaacca      8700
```

```
tagcgtcagg gaggccgggg tcccctgggg cctgccagcc ccgggtgcga ggaggcgcgg    8760
gggcagtgcc agccgaagtc tgccgttgcc caagaggccc aggcgtggcg ctgccctga    8820 gccggagcgg acgcccgttg gcaggggtc ctgggcccac ccgggcagga cgcgtggacc    8880
gagtgaccgt ggtttctgtg tggtgtcacc tgccagaccc gccgaagaag ccacctcttt    8940
ggagggtgcg ctctctggca cgcgccactc ccacccatcc gtgggccgcc agcaccacgc    9000 gggccccccca tccacatcgc ggccaccacg tccctgggac acgccttgtc ccccggtgta    9060
cgccgagacc aagcacttcc tctactcctc aggcgacaag gagcagctgc ggccctcctt    9120
cctactcagc tctctgaggc ccagcctgac tggcgctcgg aggctcgtgg agaccatctt    9180
tctgggttcc aggccctgga tgccagggac tcccccgcagg ttgccccgcc tgccccagcg    9240
ctactggcaa atgcggcccc tgtttctgga gctgcttggg aaccacgcgc agtgccccta    9300
cggggtgctc ctcaagacgc actgcccgct gcgagctgcg gtcacccccag cagccggtgt    9360 ctgtgcccgg gagaagcccc agggctctgt ggcggccccc gaggaggagg acacagaccc    9420
ccgtcgcctg gtgcagctgc tccgccagca cagcagcccc tggcaggtgt acggcttcgt    9480
gcgggcctgc ctgcgccggc tggtgccccc aggcctctgg ggctccaggc acaacgaacg    9540
ccgcttcctc aggaacacca agaagttcat ctccctgggg aagcatgcca agctctcgct    9600
gcaggagctg acgtgaagaa tgagcgtgcg gggctgcgct tggctgcgca ggagcccagg    9660
ggttggctgt gttccggccg cagagcaccg tctgcgtgag gagatcctgg ccaagttcct    9720
gcactggctg atgagtgtgt acgtcgtcga gctgctcagg tctttctttt atgtcacgga    9780
gaccacgttt caaaagaaca ggctcttttt ctaccggaag agtgtctgga gcaagttgca    9840
aagcattgga atcagacagc acttgaagag ggtgcagctg cgggagctgt cggaagcaga    9900
ggtcaggcag catcgggaag ccaggcccgc cctgctgacg tccagactcc gcttcatccc    9960
caagcctgac gggctgcggc cgattgtgaa catggactac gtcgtgggag ccagaacgtt   10020
ccgcagagaa aagagggccg agcgtctcac ctccagggtg aaggcactgt tcagcgtgct   10080
caactacgag cgggcgcggc gccccggcct cctgggcgcc tctgtgctgg gcctggacga   10140
tatccacagg gcctggcgca ccttcgtgct gcgtgtgcgg gcccaggacc cgccgcctga   10200
gctgtacttt gtcaaggtgg atgtgacggg cgcgtacgac accatccccc aggacaggct   10260
cacggaggtc atcgccagca tcatcaaacc ccagaacacg tactgcgtgc gtcggtatgc   10320
cgtggtccag aaggccgccc atgggcacgt ccgcaaggcc ttcaagagcc acgtctctac   10380
cttgacagac ctccagccgt acatgcgaca gttcgtggct cacctgcagg agaccagccc   10440
gctgagggat gccgtcgtca tcgagcagag ctcctccctg aatgaggcca gcagtggcct   10500
cttcgacgtc ttcctacgct tcatgtgcca ccacgccgtg cgcatcaggg gcaagtccta   10560
cgtccagtgc caggggatcc gcagggctc catcctctcc acgctgctct gcagcctgtg   10620
ctacggcgac atgagagaaca agctgttttgc ggggattcgg cgggacgggc tgctcctgcg   10680
tttggtggat gatttcttgt tggtgacacc tcacctcacc cacgcgaaaa ccttcctcag   10740 gacccctggtc cgaggtgtcc ctgagtatgg ctgcgtggtg aacttgcgga agacagtggt   10800
gaacttccct gtagaagacg aggccctggg tggcacggct tttgttcaga tgccggccca   10860
cggcctattc ccctggtgcg gcctgctgct ggatacccgg accctggagg tgcagagcga   10920
ctactccagc tatgcccgga cctccatcag agccagtctc accttcaacc gcggcttcaa   10980
ggctgggagg aacatgcgtc gcaaactctt tgggtcttg cggctgaagt gtcacagcct   11040
gtttctggat ttgcaggtga acagcctcca gacggtgtgc accaacatct acaagatcct   11100
```

```
cctgctgcag gcgtacaggt ttcacgcatg tgtgctgcag ctcccatttc atcagcaagt    11160
ttggaagaac cccacatttt tcctgcgcgt catctctgac acggcctccc tctgctactc    11220
catcctgaaa gccaagaacg cagggatgtc gctgggggcc aagggcgccg ccggccctct    11280
gccctccgag gccgtgcagt ggctgtgcca ccaagcattc ctgctcaagc tgactcgaca    11340
ccgtgtcacc tacgtgccac tcctggggtc actcaggaca gcccagacgc agctgagtcg    11400
gaagctcccg gggacgacgc tgactgccct ggaggccgca gccaacccgg cactgccctc    11460
agacttcaag accatcctgg actgagtcga aactcgcggc cgccatatgc atcctaggcc    11520
tattaatatt ccgagtata cgtagccggc taacgttaac ttgtttattg cagcttataa     11580
tggttacaaa taaagcaata gcatcacaaa tttcacaaat aaagcatttt tttcactgca    11640
ttctagttgt ggtttgtcca aactcatcaa tgtatcttaa cgcggatctg ggcgtggtta    11700
agggtgggaa agaatatata aggtgggggt cttatgtagt tttgtatctg ttttgcagca    11760
gccgccgccg ccatgagcac caactcgttt gatggaagca ttgtgagctc atatttgaca    11820
acgcgcatgc ccccatgggc cggggtgcgt cagaatgtga tgggctccag cattgatggt    11880
cgccccgtcc tgcccgcaaa ctctactacc ttgacctacg agaccgtgtc tggaacgccg    11940
ttggagactg cagcctccgc cgccgcttca gccgctgcag ccaccgcccg cgggattgtg    12000
actgactttg ctttcctgag cccgcttgca agcagtgcag cttcccgttc atccgcccgc    12060
gatgacaagt tgacggctct tttggcacaa ttggattctt tgacccggga acttaatgtc    12120
gtttctcagc agctgttgga tctgcgccag caggtttctg ccctgaaggc ttcctcccct    12180
cccaatgcgg tttaaaacat aaataaaaaa ccagactctg tttggatttg gatcaagcaa    12240
gtgtcttgct gtctttattt agggttttg cgcgcgcggt aggcccggga ccagcggtct    12300
cggtcgttga gggtcctgtg tattttttcc aggacgtggt aaaggtgact ctggatgttc    12360
agatacatgg gcataagccc gtctctgggg tggaggtagc accactgcag agcttcatgc    12420
tgcggggtgg tgttgtagat gatccagtcg tagcaggagc gctgggcgtg gtgcctaaaa    12480
atgtctttca gtagcaagct gattgccagg gcaggcccct tggtgtaagt gtttacaaag    12540
cggttaagct gggatgggtg catacgtggg gatatgagat gcatcttgga ctgtattttt    12600
aggttggcta tgttcccagc catatccctc cggggattca tgttgtgcag aaccaccagc    12660
acagtgtatc cggtgcactt gggaaatttg tcatgtagct tagaaggaaa tgcgtggaag    12720
aacttggaga cgcccttgtg acctccaaga ttttccatgc attcgtccat aatgatggca    12780
atgggcccac gggcggcggc ctgggcgaag atatttctgg gatcactaac gtcatagttg    12840
tgttccagga tgagatcgtc ataggccatt tttacaaagc gcgggcggag ggtgccagac    12900
tgcggtataa tggttccatc cggcccaggg gcgtagttac cctcacagat ttgcatttcc    12960
cacgctttga gttcagatgg gggatcatg tctacctgcg gggcgatgaa gaaaacggtt     13020
tccggggtag gggagatcag ctgggaagaa gcaggttcc tgagcagctg cgacttaccg      13080
cagccggtgg gcccgtaaat cacacctatt accgggtgca actggtagtt aagagagctg    13140
cagctgccgt catccctgag caggggggcc acttcgttaa gcatgtccct gactcgcatg    13200 tttttccctga ccaaatccgc cagaaggcgc tcgccgccca gcgatagcag ttcttgcaag   13260
gaagcaaagt ttttcaacgg tttgagaccg tccgccgtag gcatgctttt gagcgtttga    13320
ccaagcagtt ccaggcggtc ccacagctcg gtcacctgct ctacggcatc tcgatccagc    13380
atatctcctc gtttcgcggg ttggggcggc tttcgctgta cggcagtagt cggtgctcgt    13440
```

```
ccagacgggc cagggtcatg tctttccacg ggcgcagggt cctcgtcagc gtagtctggg    13500
tcacggtgaa ggggtgcgct ccgggctgcg cgctggccag ggtgcgcttg aggctggtcc    13560
tgctggtgct gaagcgctgc cggtcttcgc cctgcgcgtc ggccaggtag catttgacca    13620
tggtgtcata gtccagcccc tccgcggcgt ggcccttggc gcgcagcttg cccttggagg    13680
aggcgccgca cgaggggcag tgcagacttt tgagggcgta gagcttgggc gcgagaaata    13740
ccgattccgg ggagtaggca tccgcgccgc aggccccgca gacggtctcg cattccacga    13800
gccaggtgag ctctggccgt tcggggtcaa aaaccaggtt tcccccatgc ttttgatgc     13860 gtttcttacc tctggtttcc atgagccggt gtccacgctc ggtgacgaaa aggctgtccg    13920
tgtccccgta tacagacttg agaggcctgt cctcgagcgg tgttccgcgg tcctcctcgt    13980
atagaaactc ggaccactct gagacaaagg ctcgcgtcca ggccagcacg aaggaggcta    14040
agtgggaggg gtagcggtcg ttgtccacta gggggtccac tcgctccagg gtgtgaagac    14100
acatgtcgcc ctcttcggca tcaaggaagg tgattggttt gtaggtgtag gccacgtgac    14160
cgggtgttcc tgaagggggg ctataaaagg gggtgggggc gcgttcgtcc tcactctctt    14220
ccgcatcgct gtctgcgagg gccagctgtt ggggtgagta ctccctctga aaagcgggca    14280
tgacttctgc gctaagattg tcagtttcca aaaacgagga ggatttgata ttcacctggc    14340
ccgcggtgat gcctttgagg gtggccgcat ccatctggtc agaaaagaca atcttttgt     14400 tgtcaagctt ggtggcaaac gacccgtaga gggcgttgga cagcaacttg gcgatggagc    14460
gcagggtttg gttttgtcg cgatcggcgc gctccttggc cgcgatgttt agctgcacgt     14520
attcgcgcgc aacgcaccgc cattcgggaa agacggtggt gcgctcgtcg ggcaccaggt    14580
gcacgcgcca accgcggttg tgcagggtga caaggtcaac gctggtggct acctctccgc    14640
gtaggcgctc gttggtccag cagaggcggc cgcccttgcg cgagcagaat ggcggtaggg    14700
ggtctagctg cgtctcgtcc gggggtctg cgtccacggt aaagaccccg ggcagcaggc     14760
gcgcgtcgaa gtagtctatc ttgcatcctt gcaagtctag cgcctgctgc catgcgcggg    14820
cggcaagcgc gcgctcgtat gggttgagtg ggggacccca tggcatgggg tgggtgagcg    14880
cggaggcgta catgccgcaa atgtcgtaaa cgtagagggg ctctctgagt attccaagat    14940
atgtaggata gcatcttcca ccgcggatgc tggcgcgcac gtaatcgtat agttcgtgcg    15000
agggagcgag gaggtcggga ccgaggttgc tacgggcggg ctgctctgct cggaagacta    15060
tctgcctgaa gatggcatgt gagttggatg atatggttgg acgctggaag acgttgaagc    15120
tggcgtctgt gagacctacc gcgtcacgca cgaaggaggc gtaggagtcg cgcagcttgt    15180
tgaccagctc ggcggtgacc tgcacgtcta gggcgcagta gtccagggtt tccttgatga    15240
tgtcatactt atcctgtccc ttttttttcc acagctcgcg gttgaggaca aactcttcgc    15300 ggtcttttcca gtactcttgg atcggaaacc cgtcggcctc cgaacggtaa gagcctagca    15360
tgtagaactg gttgacggcc tggtaggcgc agcatccctt ttctacgggt agcgcgtatg    15420
cctgcgcggc cttccggagc gaggtgtggg tgagcgcaaa ggtgtccctg accatgactt    15480
tgaggtactg gtatttgaag tcagtgtcgt cgcatccgcc ctgctcccag agcaaaaagt    15540
ccgtgcgctt tttggaacgc ggatttgcag gggcgaaggt gacatcgttg aagagtatct    15600
ttcccgcgcg aggcataaag ttgcgtgtga tgcggaaggg tcccggcacc tcggaacggt    15660
tgttaattac ctgggcggcg agcacgatct cgtcaaagcc gttgatgttg tggcccacaa    15720
tgtaaagttc caagaagcgc gggatgccct tgatggaagg caattttta agttcctcgt     15780 aggtgagctc ttcaggggag ctgagcccgt gctctgaaag ggcccagtct gcaagatgag    15840
```

```
ggttggaagc gacgaatgag ctccacaggt cacgggccat tagcatttgc aggtggtcgc    15900
gaaaggtcct aaactggcga cctatggcca tttttctgg ggtgatgcag tagaaggtaa    15960
gcgggtcttg ttcccagcgg tcccatccaa ggttcgcggc taggtctcgc gcggcagtca    16020
ctagaggctc atctccgccg aacttcatga ccagcatgaa gggcacgagc tgcttcccaa    16080
aggcccccat ccaagtatag gtctctacat cgtaggtgac aaagagacgc tcggtgcgag    16140
gatgcgagcc gatcgggaag aactggatct cccgccacca attggaggag tggctattga    16200
tgtggtgaaa gtagaagtcc ctgcgacggg ccgaacactc gtgctggctt ttgtaaaaac    16260
gtgcgcagta ctggcagcgg tgcacgggct gtacatcctg cacgaggttg acctgacgac    16320
cgcgcacaag gaagcagagt gggaatttga gcccctcgcc tggcgggttt ggctggtggt    16380
cttctacttc ggctgcttgt ccttgaccgt ctggctgctc gaggggagtt acggtggatc    16440
ggaccaccac gccgcgcgag cccaaagtcc agatgtccgc gcgcggcggt cggagcttga    16500
tgacaacatc gcgcagatgg gagctgtcca tggtctggag ctcccgcggc gtcaggtcag    16560
gcgggagctc ctgcaggttt acctcgcata gacgggtcag ggcgcgggct agatccaggt    16620
gatacctaat ttccagggc tggttggtgg cggcgtcgat ggcttgcaag aggccgcatc    16680
cccgcggcgc gactacggta ccgcgcggcg ggcggtgggc cgcggggtg tccttggatg    16740 atgcatctaa aagcggtgac gcgggcgagc ccccggaggt agggggggct ccggacccgc    16800
cgggagaggg ggcaggggca cgtcggcgcc gcgcgcgggc aggagctggt gctgcgcgcg    16860
taggttgctg gcgaacgcga cgacgcggcg gttgatctcc tgaatctggc gcctctgcgt    16920
gaagacgacg ggcccggtga gcttgagcct gaaagagagt tcgacagaat caatttcggt    16980
gtcgttgacg gcggcctggc gcaaaatctc ctgcacgtct cctgagttgt cttgataggc    17040
gatctcggcc atgaactgct cgatctcttc ctcctggaga tctccgcgtc cggctcgctc    17100
cacggtggcg gcgaggtcgt tggaaatgcg ggccatgagc tgcagaagg cgttgaggcc    17160 tccctcgttc cagacgcggc tgtagaccac gccccttcg gcatcgcggg cgcgcatgac    17220
cacctgcgcg agattgagct ccacgtgccg ggcgaagacg gcgtagtttc gcaggcgctg    17280
aaagaggtag ttgagggtgg tggcggtgtg ttctgccacg aagaagtaca taacccagcg    17340
tcgcaacgtg gattcgttga tatccccaa ggcctcaagg cgctccatgg cctcgtagaa    17400
gtccacggcg aagttgaaaa actgggagtt gcgcgccgac acggttaact cctcctccag    17460
aagacggatg agctcggcga cagtgtcgcg cacctgcgcg tcaaaggcta caggggcctc    17520
ttcttcttct tcaatctcct cttccataag ggcctcccct tcttcttctt ctggcggcgg    17580
tggggagggg gggacacggc ggcgacgacg gcgcaccggg aggcggtcga caaagcgctc    17640
gatcatctcc ccgcggcgac ggcgcatggt ctcggtgacg gcgcggccgt tctcgcgggg    17700
gcgcagttgg aagacgccgc ccgtcatgtc ccggttatgg gttggcgggg ggctgccatg    17760
cggcagggat acgcgctaa cgatgcatct caacaattgt tgtgtaggta ctccgccgcc    17820
gagggacctg agcgagtccg catcgaccgg atcggaaaac ctctcgagaa aggcgtctaa    17880
ccagtcacag tcgcaaggta ggctgagcac cgtggcgggc ggcagcgggc ggcggtcggg    17940
gttgtttctg gcgaggtgc tgctgatgat gtaattaaag taggcggtct tgagacggcg    18000
gatggtcgac agaagcacca tgtccttggg tccggcctgc tgaatgcgca ggcggtcggc    18060
catgccccag gcttcgtttt gacatcggcg caggtctttg tagtagtctt gcatgagcct    18120
ttctaccggc acttcttctt ctccttcctc ttgtcctgca tctcttgcat ctatcgctgc    18180
```

```
ggcggcggcg gagtttggcc gtaggtggcg ccctcttcct cccatgcgtg tgaccccgaa   18240 gccoctcatc ggctgaagca gggctaggtc ggcgacaacg cgctcggcta atatggcctg   18300
ctgcacctgc gtgagggtag actggaagtc atccatgtcc acaaagcggt ggtatgcgcc   18360
cgtgttgatg gtgtaagtgc agttggccat aacggaccag ttaacggtct ggtgacccgg   18420
ctgcgagagc tcggtgtacc tgagacgcga gtaagccctc gagtcaaata cgtagtcgtt   18480
gcaagtccgc accaggtact ggtatcccac caaaaagtgc ggcggcggct ggcggtagag   18540
gggccagcgt agggtggccg gggctccggg ggcgagatct tccaacataa ggcgatgata   18600
tccgtagatg tacctggaca tccaggtgat gccggcggcg gtggtggagg cgcgcggaaa   18660
gtcgcggacg cggttccaga tgttgcgcag cggcaaaaag tgctccatgg tcgggacgct   18720
ctggccggtc aggcgcgcgc aatcgttgac gctctaccgt gcaaaaggag agcctgtaag   18780
cgggcactct tccgtggtct ggtggataaa ttcgcaaggg tatcatggcg gacgaccggg   18840
gttcgagccc cgtatccggc cgtccgccgt gatccatgcg gttaccgccc gcgtgtcgaa   18900
cccaggtgtg cgacgtcaga caacggggga gtgctccttt tggcttcctt ccaggcgcgg   18960
cggctgctgc gctagctttt ttggccactg gccgcgcgca gcgtaagcgg ttaggctgga   19020
aagcgaaagc attaagtggc tcgctccctg tagccggagg gttattttcc aagggttgag   19080
tcgcgggacc cccggttcga gtctcggacc ggccggactg cggcgaacgg gggtttgcct   19140
ccccgtcatg caagacccocg cttgcaaatt cctccggaaa cagggacgag ccccttttt   19200 gcttttccca gatgcatccg gtgctgcggc agatgcgccc ccctcctcag cagcggcaag   19260
agcaagagca gcggcagaca tgcagggcac cctccctcc tcctaccgcg tcaggagggg   19320
cgacatccgc ggttgacgcg gcagcagatg gtgattacga accccgcgg cgccgggccc   19380 ggcactacct ggacttggag gagggcgagg gcctggcgcg gctaggagcg ccctctcctg   19440
agcggtaccc aagggtgcag ctgaagcgtg atacgcgtga ggcgtacgtg ccgcggcaga   19500
acctgtttcg cgaccgcgag ggagaggagc ccgaggagat gcgggatcga aagttccacg   19560
cagggcgcga gctgcggcat ggcctgaatc gcgagcggtt gctgcgcgag gaggactttg   19620
agcccgacgc gcgaaccggg attagtcccg cgcgcgcaca cgtggcggcc gccgacctgg   19680
taaccgcata cgagcagacg gtgaaccagg agattaactt tcaaaaaagc tttaacaacc   19740
acgtgcgtac gcttgtggcg cgcgaggagg tggctatagg actgatgcat ctgtgggact   19800
ttgtaagcgc gctggagcaa aacccaaata gcaagccgct catggcgcag ctgttcctta   19860
tagtgcagca cagcagggac aacgaggcat tcagggatgc gctgctaaac atagtagagc   19920
ccgagggccg ctggctgctc gatttgataa acatcctgca gagcatagtg gtgcaggagc   19980
gcagcttgag cctggctgac aaggtggccg ccatcaacta ttccatgctt agcctgggca   20040
agttttacgc ccgcaagata taccataccc cttacgttcc catagacaag gaggtaaaga   20100
tcgaggggtt ctacatgcgc atggcgctga aggtgcttac cttgagcgac gacctgggcg   20160
tttatcgcaa cgagcgcatc cacaaggccg tgagcgtgag ccggcggcgc gagctcagcg   20220
accgcgagct gatgcacagc ctgcaaaggg ccctggctgg cacgggcagc ggcgatagag   20280
aggccgagtc ctactttgac gcgggcgctg acctgcgctg gccccaagc cgacgcgccc   20340 tggaggcagc tggggccgga cctgggctgg cggtggcacc cgcgcgcgct ggcaacgtcg   20400
gcggcgtgga ggaatatgac gaggacgatg agtacgagcc agaggacggc gagtactaag   20460
cggtgatgtt tctgatcaga tgatgcaaga cgcaacggac ccggcggtgc gggcggcgct   20520
gcagagccag ccgtccggcc ttaactccac ggacgactgg cgccaggtca tggaccgcat   20580
```

```
catgtcgctg actgcgcgca atcctgacgc gttccggcag cagccgcagg ccaaccggct   20640
ctccgcaatt ctggaagcgg tggtcccggc gcgcgcaaac cccacgcacg agaaggtgct   20700
ggcgatcgta aacgcgctgg ccgaaaacag ggccatccgg cccgacgagg ccggcctggt   20760
ctacgacgcg ctgcttcagc gcgtggctcg ttacaacagc ggcaacgtgc agaccaacct   20820
ggaccggctg gtggggatg tgcgcgaggc cgtggcgcag cgtgagcgcg cgcagcagca   20880
gggcaacctg ggctccatgg ttgcactaaa cgccttcctg agtacacagc ccgccaacgt   20940
gccgcgggga caggaggact acaccaactt tgtgagcgca ctgcggctaa tggtgactga   21000
gacaccgcaa agtgaggtgt accagtctgg gccagactat tttttccaga ccagtagaca   21060
aggcctgcag accgtaaacc tgagccaggc tttcaaaaac ttgcaggggc tgtgggggt   21120 gcgggctccc acaggcgacc gcgcgaccgt gtctagcttg ctgacgccca actcgcgcct   21180
gttgctgctg ctaatagcgc ccttcacgga cagtggcagc gtgtcccggg acacatacct   21240
aggtcacttg ctgacactgt accgcgaggc cataggtcag gcgcatgtgg acgagcatac   21300
tttccaggag attacaagtg tcagccgcgc gctggggcag gaggacacgg gcagcctgga   21360
ggcaacccta aactacctgc tgaccaaccg gcggcagaag atccccctcgt tgcacagttt   21420 aaacagcgag gaggagcgca ttttgcgcta cgtgcagcag agcgtgagcc ttaacctgat   21480
gcgcgacggg gtaacgccca gcgtggcgct ggacatgacc gcgcgcaaca tggaaccggg   21540
catgtatgcc tcaaaccggc cgtttatcaa ccgcctaatg gactacttgc atcgcgcggc   21600
cgccgtgaac cccgagtatt tcaccaatgc catcttgaac ccgcactggc taccgcccc   21660 tggtttctac accgggggat tcgaggtgcc cgagggtaac gatggattcc tctgggacga   21720
catagacgac agcgtgtttt ccccgcaacc gcagaccctg ctagagttgc aacagcgcga   21780
gcaggcagag gcggcgctgc gaaggaaag cttccgcagg ccaagcagct tgtccgatct   21840
aggcgctgcg gccccgcggt cagatgctag tagcccattt ccaagcttga tagggtctct   21900
taccagcact cgcaccaccc gcccgcgcct gctgggcgag gaggagtacc taaacaactc   21960
gctgctgcag ccgcagcgcg aaaaaaacct gcctccggca tttcccaaca acgggataga   22020
gagcctagtg gacaagatga gtagatggaa gacgtacgcg caggagcaca gggacgtgcc   22080 aggccccgcgc ccgcccaccc gtcgtcaaag gcacgaccgt cagcggggtc tggtgtggga   22140
ggacgatgac tcggcagacg acagcagcgt cctggatttg ggagggagtg caacccgtt   22200 tgcgcacctt cgccccaggc tgggagaat gttttaaaaa aaaaaagca tgatgcaaaa   22260 taaaaaactc accaaggcca tggcaccgag cgttggtttt cttgtattcc ccttagtatg   22320
cggcgcgcgg cgatgtatga ggaaggtcct cctccctcct acgagagtgt ggtgagcgcg   22380
gcgccagtgg cggcggcgct gggttctccc ttcgatgctc ccctggaccc gccgtttgtg   22440
cctccgcggt acctgcggcc taccgggggg agaaacagca tccgttactc tgagttggca   22500
cccctattcg acaccacccg tgtgtacctg gtggacaaca agtcaacgga tgtggcatcc   22560
ctgaactacc agaacgacca cagcaacttt ctgaccacgg tcattcaaaa caatgactac   22620
agcccggggg aggcaagcac acagaccatc aatcttgacg accggtcgca ctggggcggc   22680
gacctgaaaa ccatcctgca taccaacatg ccaaatgtga acgagttcat gtttaccaat   22740
aagtttaagg cgcgggtgat ggtgtcgcgc ttgcctacta aggacaatca ggtggagctg   22800
aaatacgagt gggtggagtt cacgctgccc gagggcaact actccgagac catgaccata   22860
gaccttatga acaacgcgat cgtggagcac tacttgaaag tgggcagaca gaacgggtt   22920
```

```
ctggaaagcg acatcggggt aaagtttgac acccgcaact tcagactggg gtttgacccc   22980
gtcactggtc ttgtcatgcc tggggtatat acaaacgaag ccttccatcc agacatcatt   23040
ttgctgccag gatgcggggt ggacttcacc cacagccgcc tgagcaactt gttgggcatc   23100
cgcaagcgga aacccttcca ggagggcttt aggatcacct acgatgatct ggagggtggt   23160
aacattcccg cactgttgga tgtggacgcc taccaggcga gcttgaaaga tgacaccgaa   23220
cagggcgggg tggcgcagg cggcagcaac agcagtggca gcggcgcgga agagaactcc   23280
aacgcggcag ccgcggcaat gcagccggtg gaggacatga acgatcatgc cattcgcggc   23340
gacacctttg ccacacgggc tgaggagaag cgcgctgagg ccgaagcagc ggccgaagct   23400
gccgcccccg ctgcgcaacc cgaggtcgag aagcctcaga gaaaccggt gatcaaaccc   23460
ctgacagagg acagcaagaa acgcagttac aacctaataa gcaatgacag caccttcacc   23520
cagtaccgca gctggtacct tgcatacaac tacggcgacc ctcagaccgg aatccgctca   23580
tggaccctgc tttgcactcc tgacgtaacc tgccggctcgg agcaggtcta ctggtcgttg   23640
ccagacatga tgcaagaccc cgtgaccttc cgctccacgc gccagatcag caactttccg   23700
gtggtgggcg ccgagctgtt gcccgtgcac tccaagagct tctacaacga ccaggccgtc   23760
tactcccaac tcatccgcca gtttacctct ctgacccacg tgttcaatcg ctttcccgag   23820
aaccagattt tggcgcgccc gccagccccc accatcacca ccgtcagtga aaacgttcct   23880
gctctcacag atcacgggac gctaccgctg cgcaacagca tcggaggagt ccagcgagtg   23940
accattactg acgccagacg ccgcacctgc ccctacgttt acaaggccct gggcatagtc   24000
tcgccgcgcg tcctatcgag ccgcactttt tgagcaagca tgtccatcct tatatcgccc   24060
agcaataaca caggctgggg cctgcgcttc ccaagcaaga tgtttggcgg ggccaagaag   24120
cgctccgacc aacacccagt gcgcgtgcgc gggcactacc gcgcgccctg gggcgcgcac   24180
aaacgcggcc gcactgggcg caccaccgtc gatgacgcca tcgacgcggt ggtggaggag   24240
gcgcgcaact acacgcccac gccgccacca gtgtccacag tggacgcggc cattcagacc   24300
gtggtgcgcg gagcccggcg ctatgctaaa atgaagagac ggcggaggcg cgtagcacgt   24360
cgccaccgcc gccgacccgg cactgccgcc aacgcgcgg cggcggcccct gcttaaccgc   24420
gcacgtcgca ccggccgacg ggcggccatg cgggccgctc gaaggctggc cgcgggtatt   24480
gtcactgtgc cccccaggtc caggcgacga gcggccgccg cagcagccgc ggccattagt   24540
gctatgactc agggtcgcag gggcaacgtg tattgggtgc gcgactcggt tagcggcctg   24600
cgcgtgcccg tgcgcacccg ccccccgcgc aactagattg caagaaaaaa ctacttagac   24660
tcgtactgtt gtatgtatcc agcggcggcg gcgcgcaacg aagctatgtc caagcgcaaa   24720
atcaaagaag agatgctcca ggtcatcgcg ccggagatct atggccccc gaagaaggaa   24780
gagcaggatt acaagccccg aaagctaaag cgggtcaaaa agaaaagaa agatgatgat   24840
gatgaacttg acgacgaggt ggaactgctg cacgctaccg cgcccaggcg acgggtacag   24900
tggaaaggtc gacgcgtaaa acgtgttttg cgacccggca ccaccgtagt ctttacgccc   24960
ggtgagcgct ccacccgcac ctacaagcgc gtgtatgatg aggtgtacgg cgacgaggac   25020
ctgcttgagc aggccaacga gcgcctcggg gagtttgcct acgaaagcg gcataaggac   25080
atgctggcgt tgccgctgga cgagggcaac ccaacaccta gcctaaagcc cgtaacactg   25140
cagcaggtgc tgcccgcgct tgcaccgtcc gaagaaaagc gcggcctaaa gcgcgagtct   25200
ggtgacttgg cacccaccgt gcagctgatg gtacccaagc gccagcgact ggaagatgtc   25260
ttggaaaaaa tgaccgtgga acctgggctg gagcccgagg tccgcgtgcg gccaatcaag   25320
```

```
caggtggcgc cgggactggg cgtgcagacc gtggacgttc agatacccac taccagtagc   25380
accagtattg ccaccgccac agagggcatg gagacacaaa cgtccccggt tgcctcagcg   25440
gtggcggatg ccgcggtgca ggcggtcgct gcggccgcgt ccaagacctc tacggaggtg   25500
caaacggacc cgtggatgtt tcgcgtttca gcccccgggc gcccgcgcgg ttcgaggaag   25560
tacggcgccg ccagcgcgct actgcccgaa tatgccctac atccttccat tgcgcctacc   25620
cccggctatc gtggctacac ctaccgcccc agaagacgag caactacccg acgccgaacc   25680
accactggaa cccgccgccg ccgtcgccgt cgccagcccg tgctggcccc gatttccgtg   25740
cgcagggtgg ctcgcgaagg aggcaggacc ctggtgctgc aacagcgcg ctaccacccc   25800 agcatcgttt aaaagccggt ctttgtggtt cttgcagata tggccctcac ctgccgcctc   25860
cgtttcccgg tgccgggatt ccgaggaaga atgcaccgta ggaggggcat ggccggccac   25920
ggcctgacgg gcggcatgcg tcgtgcgcac caccggcggc ggcgcgcgtc gcaccgtcgc   25980
atgcgcggcg gtatcctgcc cctccttatt ccactgatcg ccgcggcgat tggcgccgtg   26040
cccggaattg catccgtggc cttgcaggcg cagagacact gattaaaaac aagttgcatg   26100
tggaaaaatc aaaataaaaa gtctggactc tcacgctcgc ttggtcctgt aactattttg   26160
tagaatggaa gacatcaact ttgcgtctct ggccccgcga cacggctcgc gcccgttcat   26220
gggaaactgg caagatatcg gcaccagcaa tatgagcggt ggcgccttca gctgggcgtc   26280
gctgtggagc ggcattaaaa atttcggttc caccgttaag aactatggca gcaaggcctg   26340
gaacagcagc acaggccaga tgctgaggga taagttgaaa gagcaaaatt ccaacaaaa   26400 ggtggtagat ggcctggcct ctggcattag cggggtggtg gacctggcca accaggcagt   26460
gcaaaataag attaacagta agcttgatcc ccgcccctccc gtagaggagc ctccaccggc   26520
cgtggagaca gtgtctccag agggggcgtgg cgaaaagcgt ccgcgccccg acagggaaga   26580
aactctggtg acgcaaatag acgagcctcc ctcgtacgag gaggcactaa agcaaggcct   26640
gcccaccacc cgtcccatcg cgcccatggc taccggagtg ctgggccagc acacacccgt   26700
aacgctggac ctgcctcccc ccgccgacac ccagcagaaa cctgtgctgc caggcccgac   26760
cgccgttgtt gtaacccgtc ctagccgcgc gtccctgcgc cgcgccgcca gcggtccgcg   26820
atcgttgcgg cccgtagcca gtggcaactg gcaaagcaca ctgaacagca tcgtgggtct   26880
gggggtgcaa tccctgaagc gccgacgatg cttctgaata gctaacgtgt cgtatgtgtg   26940
tcatgtatgc gtccatgtcg ccgccagagg agctgctgag ccgccgcgcg cccgcttt cc   27000 aagatggcta ccccttcgat gatgccgcag tggtcttaca tgcacatctc gggccaggac   27060
gcctcggagt acctgagccc cgggctggtg cagtttgccc gcgccaccga acgtacttc   27120 agcctgaata acaagtttag aaaccccacg gtggcgccta cgcacgacgt gaccacagac   27180
cggtcccagc gtttgacgct gcggttcatc cctgtggacc gtgaggatac tgcgtactcg   27240
tacaaggcgc ggttcaccct agctgtgggt gataaccgtg tgctggacat ggcttccacg   27300
tactttgaca tccgcggcgt gctggacagg ggccctactt ttaagcccta ctctggcact   27360
gcctacaacg ccctggctcc caagggtgcc ccaaatcctt gcgaatggga tgaagctgct   27420
actgctcttg aaataaacct agaagaagag gacgatgaca acgaagacga agtagacgag   27480
caagctgagc agcaaaaaac tcacgtattt gggcaggcgc cttattctgg tataaatatt   27540
acaaaggagg gtattcaaat aggtgtcgaa ggtcaaacac ctaaatatgc cgataaaaca   27600
tttcaacctg aacctcaaat aggagaatct cagtggtacg aaactgaaat taatcatgca   27660
```

```
gctgggagag tccttaaaaa gactacccca atgaaaccat gttacggttc atatgcaaaa   27720
cccacaaatg aaaatggagg gcaaggcatt cttgtaaagc aacaaaatgg aaagctagaa   27780
agtcaagtgg aaatgcaatt tttctcaact actgaggcga ccgcaggcaa tggtgataac   27840
ttgactccta aagtggtatt gtacagtgaa gatgtagata tagaaacccc agacactcat   27900
atttcttaca tgcccactat taaggaaggt aactcacgag aactaatggg ccaacaatct   27960
atgcccaaca ggcctaatta cattgctttt agggacaatt ttattggtct aatgtattac   28020
aacagcacgg gtaatatggg tgttctggcg ggccaagcat cgcagttgaa tgctgttgta   28080
gatttgcaag acagaaacac agagctttca taccagcttt tgcttgattc cattggtgat   28140
agaaccaggt acttttctat gtggaatcag gctgttgaca gctatgatcc agatgttaga   28200
attattgaaa tcatggaac tgaagatgaa cttccaaatt actgctttcc actgggaggt   28260
gtgattaata cagagactct taccaaggta aaacctaaaa caggtcagga aaatggatgg   28320 gaaaagatg ctacagaatt ttcagataaa aatgaaataa gagttggaaa taattttgcc   28380
atggaaatca atctaaatgc caacctgtgg agaaatttcc tgtactccaa catagcgctg   28440
tatttgcccg acaagctaaa gtacagtcct tccaacgtaa aaatttctga taacccaaac   28500
acctacgact acatgaacaa gcgagtggtg gctcccgggt tagtggactg ctacattaac   28560
cttggagcac gctggtccct tgactatatg gacaacgtca acccatttaa ccaccaccgc   28620
aatgctggcc tgcgctaccg ctcaatgttg ctgggcaatg gtcgctatgt gcccttccac   28680
atccaggtgc ctcagaagtt ctttgccatt aaaaacctcc ttctcctgcc gggctcatac   28740
acctacgagt ggaacttcag gaaggatgtt aacatggttc tgcagagctc cctaggaaat   28800
gacctaaggg ttgacggagc cagcattaag tttgatagca tttgcctttta cgccaccttc   28860 ttccccatgg cccacaacac cgcctccacg cttgaggcca tgcttagaaa cgacaccaac   28920
gaccagtcct ttaacgacta tctctccgcc gccaacatgc tctaccctat acccgccaac   28980
gctaccaacg tgcccatatc catccccctcc cgcaactggg cggctttccg cggctgggcc   29040
ttcacgcgcc ttaagactaa ggaaacccca tcactgggct cgggctacga cccttattac   29100
acctactctg gctctatacc ctacctagat ggaacctttt acctcaacca caccttaag   29160 aaggtggcca ttaccttga ctcttctgtc agctggcctg gcaatgaccg cctgcttacc   29220
cccaacgagt ttgaaattaa cgcgctcagtt gacggggagg gttacaacgt tgcccagtgt   29280
aacatgacca aagactggtt cctggtacaa atgctagcta actacaacat tggctaccag   29340
ggcttctata tcccagagag ctacaaggac cgcatgtact ccttctttag aaacttccag   29400
cccatgagcc gtcaggtggt ggatgatact aaaatacaagg actaccaaca ggtgggcatc   29460
ctacaccaac acaacaactc tggatttgtt ggctaccttg cccccaccat gcgcgaagga   29520
caggcctacc ctgctaactt cccctatccg cttataggca agaccgcagt tgacagcatt   29580
acccagaaaa agtttctttg cgatcgcacc ctttggcgca tcccattctc cagtaacttt   29640
atgtccatgg gcgcactcac agacctgggc caaaaccttc tctacgccaa ctccgcccac   29700
gcgctagaca tgactttgga ggtggatccc atggacgagc ccaccccttct ttatgttttg   29760 tttgaagtct ttgacgtggt ccgtgtgcac ggccgcacc gcggcgtcat cgaaaccgtg   29820
tacctgcgca cgcccttctc ggccggcaac gccacaacat aaagaagcaa gcaacatcaa   29880
caacagctgc cgccatgggc tccagtgagc aggaactgaa agccattgtc aaagatcttg   29940
gttgtgggcc atattttttg ggcacctatg acaagcgctt tccaggcttt gtttctccac   30000
acaagctcgc ctgcgccata gtcaatacgg ccggtcgcga gactggggggc gtacactgga   30060
```

```
tggcctttgc ctggaacccg cactcaaaaa catgctacct cttttgagccc tttggctttt    30120
ctgaccagcg actcaagcag gtttaccagt ttgagtacga gtcactcctg cgccgtagcg    30180
ccattgcttc ttcccccgac cgctgtataa cgctggaaaa gtccacccaa agcgtacagg    30240
ggcccaactc ggccgcctgt ggactattct gctgcatgtt tctccacgcc tttgccaact    30300
ggccccaaac tcccatggat cacaacccca ccatgaacct tattaccggg gtacccaact    30360
ccatgctcaa cagtccccag gtacagccca ccctgcgtcg caaccaggaa cagctctaca    30420
gcttcctgga gcgccactcg ccctacttcc gcagccacag tgcgcagatt aggagcgcca    30480
cttcttttg tcacttgaaa aacatgtaaa aataatgtac tagagacact ttcaataaag    30540
gcaaatgctt ttatttgtac actctcgggt gattatttac ccccacccctt gccgtctgcg    30600
ccgtttaaaa atcaaagggg ttctgccgcg catcgctatg cgccactggc agggacacgt    30660
tgcgatactg gtgtttagtg ctccacttaa actcaggcac aaccatccgc ggcagctcgg    30720
tgaagttttc actccacagg ctgcgcacca tcaccaacgc gtttagcagg tcgggcgccg    30780
atatcttgaa gtcgcagttg gggcctccgc cctgcgcgcg cgagttgcga tacacagggt    30840
tgcagcactg gaacactatc agcgccgggt ggtgcacgct ggccagcacg ctcttgtcgg    30900
agatcagatc cgcgtccagg tcctccgcgt tgctcagggc gaacggagtc aactttggta    30960
gctgccttcc caaaagggc gcgtgcccag gctttgagtt gcactcgcac cgtagtggca    31020
tcaaaaggtg accgtgcccg gtctgggcgt taggatacag cgcctgcata aaagccttga    31080
tctgcttaaa agccacctga gccttttgcgc cttcagagaa gaacatgccg caagacttgc    31140
cggaaaactg attggccgga caggccgcgt cgtgcacgca gcaccttgcg tcggtgttgg    31200
agatctgcac cacatttcgg ccccaccggt tcttcacgat cttggccttg ctagactgct    31260
ccttcagcgc gcgctgcccg ttttcgctcg tcacatccat ttcaatcacg tgctccttat    31320
ttatcataat gcttccgtgt agacacttaa gctcgccttc gatctcagcg cagcggtgca    31380
gccacaacgc gcagcccgtg ggctcgtgat gcttgtaggt cacctctgca aacgactgca    31440
ggtacgcctg caggaatcgc cccatcatcg tcacaaaggt cttgttgctg gtgaaggtca    31500
gctgcaaccc gcggtgctcc tcgttcagcc aggtcttgca tacggccgcc agagcttcca    31560
cttggtcagg cagtagtttg aagttcgcct ttagatcgtt atccacgtgg tacttgtcca    31620
tcagcgcgcg cgcagcctcc atgcccttct cccacgcaga cacgatcggc acactcagcg    31680
ggttcatcac cgtaatttca ctttccgctt cgctgggctc ttcctcttcc tcttgcgtcc    31740
gcataccacg cgccactggg tcgtcttcat tcagccgccg cactgtgcgc ttacctcctt    31800
tgccatgctt gattagcacc ggtgggttgc tgaaacccac catttgtagc gccacatctt    31860
ctctttcttc ctcgctgtcc acgattacct ctggtgatgg cggcgctcg ggcttgggag    31920
aagggcgctt ctttttcttc ttgggcgcaa tggccaaatc cgccgccgag gtcgatggcc    31980
gcgggctggg tgtgcgcggc accagcgcgt cttgtgatga gtcttcctcg tcctcggact    32040
cgatacgccg cctcatccgc ttttttgggg gcgcccgggg aggcggcggc gacggggacg    32100
gggacgacac gtcctccatg gttggggac gtcgcgccgc accgcgtccg cgctcggggg    32160
tggtttcgcg ctgctcctct tcccgactgg ccatttcctt ctcctatagg cagaaaaaga    32220
tcatggagtc agtcgagaag aaggacagcc taaccgcccc ctctgagttc gccaccaccg    32280
cctccaccga tgccgccaac gcgcctacca ccttccccgt cgaggcaccc ccgcttgagg    32340
aggaggaagt gattatcgag caggacccag gttttgtaag cgaagacgac gaggaccgct    32400
```

```
cagtaccaac agaggataaa aagcaagacc aggacaacgc agaggcaaac gaggaacaag    32460
tcgggcgggg ggacgaaagg catggcgact acctagatgt gggagacgac gtgctgttga    32520
agcatctgca gcgccagtgc gccattatct gcgacgcgtt gcaagagcgc agcgatgtgc    32580
ccctcgccat agcggatgtc agccttgcct acgaacgcca cctattctca ccgcgcgtac    32640
cccccaaacg ccaagaaaac ggcacatgcg agcccaaccc gcgcctcaac ttctaccccg    32700
tatttgccgt gccagaggtg cttgccacct atcacatctt tttccaaaac tgcaagatac    32760
ccctatcctg ccgtgccaac cgcagccgag cggacaagca gctggccttg cggcagggcg    32820
ctgtcatacc tgatatcgcc tcgctcaacg aagtgccaaa aatctttgag ggtcttggac    32880
gcgacgagaa gcgcgcggca aacgctctgc aacaggaaaa cagcgaaaat gaaagtcact    32940
ctggagtgtt ggtggaactc gagggtgaca acgcgcgcct agccgtacta aaacgcagca    33000
tcgaggtcac ccactttgcc tacccggcac ttaacctacc ccccaaggtc atgagcacag    33060
tcatgagtga gctgatcgtg cgccgtgcgc agccctgga gagggatgca aatttgcaag    33120
aacaaacaga ggagggccta cccgcagttg gcgacgagca gctagcgcgc tggcttcaaa    33180
cgcgcgagcc tgccgacttg gaggagcgac gcaaactaat gatggccgca gtgctcgtta    33240
ccgtggagct tgagtgcatg cagcggttct ttgctgaccc ggagatgcag cgcaagctag    33300
aggaaacatt gcactacacc tttcgacagg gctacgtacg ccaggcctgc aagatctcca    33360
acgtggagct ctgcaacctg gtctcctacc ttggaatttt gcacgaaaac cgccttgggc    33420
aaaacgtgct tcattccacg ctcaagggcg aggcgcgccg cgactacgtc cgcgactgcg    33480
tttacttatt tctatgctac acctggcaga cggccatggg cgtttggcag cagtgcttgg    33540
aggagtgcaa cctcaaggag ctgcagaaac tgctaaagca aaacttgaag gacctatgga    33600
cggccttcaa cgagcgctcc gtggccgcgc acctggcgga catcatttc cccgaacgcc    33660 tgcttaaaac cctgcaacag ggtctgccag acttcaccag tcaaagcatg ttgcagaact    33720
ttaggaactt tatcctagag cgctcaggaa tcttgcccgc cacctgctgt gcacttccta    33780
gcgactttgt gccattaag taccgcgaat gccctccgcc gctttgggc cactgctacc    33840 ttctgcagct agccaactac cttgcctacc actctgacat aatggaagac gtgagcggtg    33900
acggtctact ggagtgtcac tgtcgctgca acctatgcac cccgcaccgc tccctggttt    33960
gcaattcgca gctgcttaac gaaagtcaaa ttatcggtac cttgagctg cagggtccct    34020 cgcctgacga aaagtccgcg gctccggggt tgaaactcac tccggggctg tggacgtcgg    34080
cttaccttcg caaatttgta cctgaggact accacgccca cgagattagg ttctacgaag    34140
accaatcccg cccgccaaat gcggagctta ccgcctgcgt cattacccag ggccacattc    34200
ttggccaatt gcaagccatc aacaaagccc gccaagagtt tctgctacga aagggacggg    34260
gggtttactt ggaccccag tccggcgagg agctcaaccc aatcccccg ccgccgcagc    34320 cctatcagca gcagccgcgg gcccttgctt cccaggatgg cacccaaaaa gaagctgcag    34380
ctgccgccgc cacccacgga cgaggaggaa tactgggaca gtcaggcaga ggaggttttg    34440
gacgaggagg aggaggacat gatggaagac tgggagagcc tagacgagga agcttccgag    34500
gtcgaagagg tgtcagacga aacaccgtca ccctcggtcg cattccctc gccggcgccc    34560 cagaaatcgg caaccggttc cagcatggct acaacctccg ctcctcaggc gccgccggca    34620
ctgcccgttc gccgacccaa ccgtagatgg gacaccactg gaaccagggc cggtaagtcc    34680
aagcagccgc cgccgttagc ccaagagcaa caacagcgcc aaggctaccg ctcatggcgc    34740
gggcacaaga acgccatagt tgcttgcttg caagactgtg ggggcaacat ctccttcgcc    34800
```

```
cgccgctttc ttctctacca tcacggcgtg gccttccccc gtaacatcct gcattactac    34860
cgtcatctct acagcccata ctgcaccggc ggcagcggca gcggcagcaa cagcagcggc    34920
cacacagaag caaaggcgac cggatagcaa gactctgaca aagcccaaga aatccacagc    34980
ggcggcagca gcaggaggag gagcgctgcg tctggcgccc aacgaacccg tatcgacccg    35040
cgagcttaga aacaggattt ttcccactct gtatgctata tttcaacaga gcaggggcca    35100
agaacaagag ctgaaaataa aaaacaggtc tctgcgatcc ctcacccgca gctgcctgta    35160
tcacaaaagc gaagatcagc ttcggcgcac gctggaagac gcggaggctc tcttcagtaa    35220
atactgcgcg ctgactctta aggactagtt tcgcgccctt tctcaaattt aagcgcgaaa    35280
actacgtcat ctccagcggc cacacccggc gccagcacct gtcgtcagcg ccattatgag    35340
caaggaaatt cccacgccct acatgtggag ttaccagcca caaatgggac ttgcggctgg    35400
agctgcccaa gactactcaa cccgaataaa ctacatgagc gcggaccccc acatgatatc    35460
ccgggtcaac ggaatccgcg cccaccgaaa ccgaattctc ttggaacagg cggctattac    35520
caccacacct cgtaataacc ttaatccccg tagttggccc gctgccctgg tgtaccagga    35580
aagtcccgct cccaccactg tggtacttcc cagagacgcc caggccgaag ttcagatgac    35640
taactcaggg gcgcagcttg cgggcggctt tcgtcacagg gtgcggtcgc ccgggcaggg    35700
tataactcac ctgacaatca gagggcgagg tattcagctc aacgacgagt cggtgagctc    35760
ctcgcttggt ctccgtccgg acgggacatt tcagatcggc ggcgccggcc gtccttcatt    35820
cacgcctcgt caggcaatcc taactctgca gacctcgtcc tctgagccgc gctctggagg    35880
cattggaact ctgcaattta ttgaggagtt tgtgccatcg gtctacttta accccttctc    35940
gggacctccc ggccactatc cggatcaatt tattcctaac tttgacgcgg taaaggactc    36000
ggcggacggc tacgactgaa tgttaagtgg agaggcagag caactgcgcc tgaaacacct    36060
ggtccactgt cgccgccaca agtgctttgc ccgcgactcc ggtgagtttt gctactttga    36120
attgcccgag gatcatatcg agggcccggc gcacggcgtc cggcttaccg cccagggaga    36180
gcttgcccgt agcctgattc gggagtttac ccagcgcccc ctgctagttg agcgggacag    36240
gggaccctgt gttctcactg tgatttgcaa ctgtcctaac cttggattac atcaagatcc    36300
tctagttata actagagtac ccgggggatct tattccctttt aactaataaa aaaaaataat   36360
aaagcatcac ttacttaaaa tcagttagca aatttctgtc cagtttattc agcagcacct    36420
ccttgccctc ctcccagctc tggtattgca gcttcctcct ggctgcaaac tttctccaca    36480
atctaaatgg aatgtcagtt tcctcctgtt cctgtccatc cgcacccact atcttcatgt    36540
tgttgcagat gaagcgcgca agaccgtctg aagatacctt caaccccgtg tatccatatg    36600
acacggaaac cggtcctcca actgtgcctt ttcttactcc tcccttttgta tcccccaatg    36660 ggtttcaaga gagtcccccct ggggtactct ctttgcgcct atccgaacct ctagttacct    36720
ccaatggcat gcttgcgctc aaaatgggca acggcctctc tctggacgag gccggcaacc    36780
ttacctccca aaatgtaacc actgtgagcc cacctctcaa aaaaccaag tcaaacataa     36840 acctggaaat atctgcaccc ctcacagtta cctcagaagc cctaactgtg gctgccgccg    36900
cacctctaat ggtcgcgggc aacacactca ccatgcaatc acaggccccg ctaaccgtgc    36960
acgactccaa acttagcatt gccacccaag gaccccctcac agtgtcagaa ggaaagctag    37020
ccctgcaaac atcaggcccc ctcaccacca ccgatagcag taccctact atcactgcct     37080 cacccccctct aactactgcc actggtagct tgggcattga cttgaaagag cccatttata    37140
```

```
cacaaaatgg aaaactagga ctaaagtacg gggctccttt gcatgtaaca gacgacctaa    37200
acactttgac cgtagcaact ggtccaggtg tgactattaa taatacttcc ttgcaaacta    37260
aagttactgg agccttgggt tttgattcac aaggcaatat gcaacttaat gtagcaggag    37320
gactaaggat tgattctcaa aacagacgcc ttatacttga tgttagttat ccgtttgatg    37380
ctcaaaacca actaaatcta agactaggac agggccctct ttttataaac tcagcccaca    37440
acttggatat taactacaac aaaggccttt acttgtttac agcttcaaac aattccaaaa    37500
agcttgaggt taacctaagc actgccaagg ggttgatgtt tgacgctaca gccatagcca    37560
ttaatgcagg agatgggctt gaatttggtt cacctaatgc accaaacaca aatcccctca    37620
aaacaaaaat tggccatggc ctagaatttg attcaaacaa ggctatggtt cctaaactag    37680
gaactggcct tagttttgac agcacaggtg ccattacagt aggaaacaaa ataatgata    37740 agctaacttt gtggaccaca ccagctccat ctcctaactg tagactaaat gcagagaaag    37800
atgctaaact cactttggtc ttaacaaaat gtggcagtca atacttgct acagtttcag    37860 ttttggctgt taaaggcagt ttggctccaa tatctggaac agttcaaagt gctcatctta    37920
ttataagatt tgacgaaaat ggagtgctac taaacaattc cttcctggac ccagaatatt    37980
ggaactttag aaatggagat cttactgaag gcacagccta tacaaacgct gttggattta    38040 tgcctaaccct atcagcttat ccaaaatctc acggtaaaac tgccaaaagt aacattgtca    38100
gtcaagttta cttaaacgga gacaaaacta aacctgtaac actaaccatt acactaaacg    38160
gtacacagga acaggagac acaactccaa gtgcatactc tatgtcattt tcatgggact    38220
ggtctggcca caactacatt aatgaaatat ttgccacatc ctcttacact ttttcataca    38280
ttgcccaaga ataaagaatc gtttgtgtta tgtttcaacg tgtttatttt tcaattgcag    38340
aaaatttcaa gtcattttc attcagtagt atagccccac caccacatag cttatacaga    38400
tcaccgtacc ttaatcaaac                                                38420
```

<210> SEQ ID NO 2
<211> LENGTH: 12741
<212> TYPE: DNA
<213> ORGANISM: Artificial Sequence
<220> FEATURE:
<223> OTHER INFORMATION: Synthetic polynucleotide

<400> SEQUENCE: 2

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcgggggaga     600
attagatcgc gatgggaaaa aattcggtta aggccagggg gaagaaaaaa atataaatta     660
aaacatatag tatgggcaag cagggagcta gaacgattcg cagttaatcc tggcctgtta     720
gaaacatcag aaggctgtag acaaatactg ggacagctac aaccatccct tcagacagga     780
```

```
tcagaagaac ttagatcatt atataataca gtagcaaccc tctattgtgt gcatcaaagg      840
atagagataa aagacaccaa ggaagcttta gacaagatag aggaagagca aaacaaaagt      900
aagaccaccg cacagcaagc ggccgctgat cttcagacct ggaggaggag atatgaggga      960
caattggaga agtgaattat ataaatataa agtagtaaaa attgaaccat taggagtagc     1020
acccaccaag gcaaagagaa gagtggtgca gagagaaaaa agagcagtgg gaataggagc     1080
tttgttcctt gggttcttgg gagcagcagg aagcactatg ggcgcagcgt caatgacgct     1140
gacggtacag gccagacaat tattgtctgg tatagtgcag cagcagaaca atttgctgag     1200
ggctattgag gcgcaacagc atctgttgca actcacagtc tggggcatca agcagctcca     1260
ggcaagaatc ctggctgtgg aaagatacct aaaggatcaa cagctcctgg ggatttgggg     1320
ttgctctgga aaactcattt gcaccactgc tgtgccttgg aatgctagtt ggagtaataa     1380
atctctggaa cagatttgga atcacacgac ctggatggag tgggacagag aaattaacaa     1440
ttacacaagc ttaatacact ccttaattga agaatcgcaa aaccagcaag aaaagaatga     1500
acaagaatta ttggaattag ataaatgggc aagtttgtgg aattggttta acataacaaa     1560
ttggctgtgg tatataaaat tattcataat gatagtagga ggcttggtag gtttaagaat     1620 agttttgct gtactttcta tagtgaatag agttaggcag ggatattcac cattatcgtt      1680
tcagacccac ctcccaaccc cgaggggacc cgacaggccc gaaggaatag aagaagaagg     1740
tggagagaga gacagagaca gatccattcg attagtgaac ggatctcgac ggtatcgatt     1800
gggcccgaga tctcgcgcgc gaggcctgcc atgggcatgc ctgcaggtcg atgcgtggcc     1860
ggcctaggat ccatatggta ccggtaaatg gcccgcctgg ctgaccgccc aacgacccc     1920 gcccattgac gtcaataatg acgtatgttc ccatagtaac gccaataggg actttccatt     1980
gacgtcaatg ggtggagtat ttacggtaaa ctgcccactt ggcagtacat caagtgtatc     2040
atatgccaag tacgccccct attgacgtca atgacggtaa atggcccgcc tggcattatg     2100
cccagtacat gaccttatgg gactttccta cttggcagta catctagtat tagtcatcgc     2160
tattaccatg gtgatgcggt tttggcagta catcaatggg cgtggatagc ggtttgactc     2220
acggggattt ccaagtctcc accccattga cgtcaatggg agtttgtttt ggcaccaaaa     2280
tcaacgggac tttccaaaat gtcgtaacaa ctccgcccca ttgacgcaaa tgggcggtag     2340
gcgtgtacgg tgggaggtct atataagcag agctcgttta gtgaaccgtc agatcgcctg     2400
gagacgccat ccacgctgtt ttgacctcca tagaagacac cgggaccgat ccagcctccg     2460
cggccgggaa cggtgcattg gaacgcggat tccccgtgcc aagagtgacg taagtaccgc     2520
ctatagactc tataggcaca ccctttggc tcttatgcat gaattaatac gactcactat      2580
agggagacag actgttcctt tcctgggtct tttctgcagg ctagcccac catgccgcgc      2640 gctccccgct gccgagccgt gcgctccctg ctgcgcagcc actaccgcga ggtgctgccg     2700
ctggccacgt tcgtgcggcg cctggggccc cagggctggc ggctggtgca gcgcggggac     2760
ccggcggctt tccgcgcgct ggtggcccag tgcctggtgt gcgtgccctg ggacgcacgg     2820
ccgccccccg ccgcccccctc cttccgccag gtgtcctgcc tgaaggagct ggtggcccga     2880
gtgctgcaga ggctgtgcga gcgcggcgcg aagaacgtgc tggccttcgg cttcgcgctg     2940
ctggacgggg cccgcggggg ccccccgag gccttcacca ccagcgtgcg cagctacctg      3000
cccaacacgt tgaccgacgc actgcggggg agcggggcgt gggggctgct gttgcgccgc     3060
gtgggcgacg acgtgctggt tcacctgctg gcacgctgcg cgctctttgt gctggtggct     3120
```

-continued

```
cccagctgcg cctaccaggt gtgcgggccg ccgctgtacc agctcggcgc tgccactcag    3180
gcccggcccc cgccacacgc tagtggaccc cgaaggcgtc tgggatgcga acgggcctgg    3240
aaccatagcg tcagggaggc cggggtcccc ctgggcctgc cagccccggg tgcgaggagg    3300
cgcgggggca gtgccagccg aagtctgccg ttgcccaaga ggcccaggcg tggcgctgcc    3360
cctgagccgg agcggacgcc cgttgggcag gggtcctggg cccacccggg caggacgcgt    3420
ggaccgagtg accgtggttt ctgtgtggtg tcacctgcca gacccgccga agaagccacc    3480
tctttggagg gtgcgctctc tggcacgcgc cactcccacc catccgtggg ccgccagcac    3540
cacgcgggcc cccatccac atcgcggcca ccagtccct gggacacgcc ttgtcccccg    3600
gtgtacgccg agaccaagca cttcctctac tcctcaggcg acaaggagca gctgcggccc    3660
tccttcctac tcagctctct gaggcccagc ctgactggcg ctcggaggct cgtggagacc    3720
atctttctgg gttccaggcc ctggatgcca gggactcccc gcaggttgcc ccgcctgccc    3780
cagcgctact ggcaaatgcg gcccctgttt ctggagctgc ttgggaacca cgcgcagtgc    3840
ccctacgggg tgctcctcaa gacgcactgc ccgctgcgag ctgcgtcac cccagcagcc    3900 ggtgtctgtg cccgggagaa gccccagggc tctgtggcgg ccccgagga ggaggacaca    3960 gacccccgtc gcctggtgca gctgctccgc cagcacagca gccctggca ggtgtacggc    4020 ttcgtgcggg cctgcctgcg ccggctggtg cccccaggcc tctgggctc caggcacaac    4080 gaacgccgct tcctcaggaa caccaagaag ttcatctccc tggggaagca tgccaagctc    4140
tcgctgcagg agctgacgtg gaagatgagc gtgcggggct gcgcttggct gcgcaggagc    4200
ccaggggttg gctgtgttcc ggccgcagag caccgtctgc gtgaggagat cctggccaag    4260
ttcctgcact ggctgatgag tgtgtacgtc gtcgagctgc tcaggtcttt cttttatgtc    4320
acggagacca cgtttcaaaa gaacaggctc tttttctacc ggaagagtgt ctggagcaag    4380
ttgcaaagca ttggaatcag acagcacttg aagagggtgc agctgcggga gctgtcggaa    4440
gcagaggtca ggcagcatcg ggaagccagg cccgccctgc tgacgtccag actccgcttc    4500
atccccaagc ctgacgggct gcggccgatt gtgaacatgg actacgtcgt gggagccaga    4560
acgttccgca gagaaaagag ggccgagcgt ctcacctcca gggtgaaggc actgttcagc    4620
gtgctcaact acgagcgggc gcggcgcccc ggcctcctgg gcgcctctgt gctgggcctg    4680
gacgatatcc acagggcctg gcgcaccttc gtgctgcgtg tgcgggccca ggacccgccg    4740
cctgagctgt actttgtcaa ggtggatgtg acgggcgcgt acgacaccat cccccaggac    4800
aggctcacgg aggtcatcgc cagcatcatc aaacccagaa acacgtactg cgtgcgtcgg    4860
tatgccgtgg tccagaaggc cgcccatggg cacgtccgca aggccttcaa gagccacgtc    4920
tctaccttga cagacctcca gccgtacatg cgacagttcg tggctcacct gcaggagacc    4980
agcccgctga gggatgccgt cgtcatcgag cagagctcct ccctgaatga ggccagcagt    5040
ggcctcttcg acgtcttcct acgcttcatg tgccaccacg ccgtgcgcat caggggcaag    5100
tcctacgtcc agtgccaggg gatcccgcag ggctccatcc tctccacgct gctctgcagc    5160
ctgtgctacg gcgacatgga gaacaagctg tttgcgggga ttcggcggga cgggctgctc    5220
ctgcgtttgg tggatgattt cttgttggtg acacctcacc tcacccacgc gaaaaccttc    5280
ctcaggaccc tggtccgagg tgtccctgag tatggctgcg tggtgaactt gcggaagaca    5340
gtggtgaact tccctgtaga agacgaggcc ctgggtggca cggcttttgt tcagatgccg    5400
gcccacggcc tattccctg gtgcggcctg ctgctggata cccggaccct ggaggtgcag    5460
agcgactact ccagctatgc ccggacctcc atcagagcca gtctcacctt caaccgcggc    5520
```

```
ttcaaggctg ggaggaacat gcgtcgcaaa ctctttgggg tcttgcggct gaagtgtcac    5580
agcctgtttc tggatttgca ggtgaacagc ctccagacgt gtgcaccaa catctacaag     5640 atcctcctgc tgcaggcgta caggtttcac gcatgtgtgc tgcagctccc atttcatcag    5700
caagtttgga agaaccccac attttttcctg cgcgtcatct ctgacacggc ctccctctgc   5760
tactccatcc tgaaagccaa gaacgcaggg atgtcgctgg gggccaaggg cgccgccggc    5820
cctctgccct ccgaggccgt gcagtggctg tgccaccaag cattcctgct caagctgact    5880
cgacaccgtg tcacctacgt gccactcctg gggtcactca ggacagccca gacgcagctg    5940
agtcggaagc tcccggggac gacgctgact gccctggagg ccgcagccaa cccggcactg    6000
ccctcagact tcaagaccat cctggactga gtcgaaactc gaggatccgg ctgtggaatg    6060
tgtgtcagtt agggtgtgga aagtcccag gctccccagc aggcagaagt atgcaaagca     6120
tgcatctcaa ttagtcagca accaggtgtg gaaagtcccc aggctcccca gcaggcagaa    6180
gtatgcaaag catgcatctc aattagtcag caaccatagt cccgcccta actccgccca     6240 tcccgcccct aactccgccc agttccgccc attctccgcc ccatggctga ctaatttttt    6300
ttatttatgc agaggccgag gccgcctcgg cctctgagct attccagaag tagtgaggag    6360
gcttttttgg aggccgtcgg ccgccacgac cggtgccgcc accatcccct gacccacgcc    6420
cctgacccct cacaaggaga cgaccttcca tgaccgagta caagcccacg gtgcgcctcg    6480
ccacccgcga cgacgtcccc cgggccgtac gcaccctcgc cgccgcgttc gccgactacc    6540
ctgcaacacg ccatacagtg gaccctgacc gccacatcga gcgggtcacc gagctgcaag    6600
aactcttcct cacgcgcgtc gggctcgaca tcggcaaggt gtgggtcgcg gacgacggcg    6660
ccgcggtggc ggtctggacc acgcggaga gcgtcgaagc gggggcggtg ttcgccgaga     6720
tcggcccgcg catggccgag ttgagcggtt cccggctggc cgcgcagcaa cagatggaag    6780
gcctcctggc gccgcaccgg cccaaggagc ccgcgtggtt cctggccacc gtcggcgtct    6840
cgcccgacca ccagggcaag gtctgggca gcgccgtcgt gctccccgga gtggaggcgg     6900
ccgagcgcgc cggggtgccc gccttcctgg agacctccgc gccccgcaac ctccccttct    6960
acgagcggct cggcttcacc gtcaccgccg acgtcgaggt gcccgaagga ccgcgcacct    7020
ggtgcatgac ccgcaagccc ggtgcctgac gcccgcccca cgacccgcag cgcccgaccg    7080
aaaggagcgc acgaccccat gcatcgataa aataaaagat tttatttagt ctccagaaaa    7140 agggggaat gaaagacccc acctgtaggt ttggcaagct aggcctatta atattccgga     7200
gtatacgtag ccggctaacg ttaacaaccg gtacgatgca ttagttatta atagtaatca    7260
attacggggt cattagttca tagcccatat atggagttcc gcgttacata acttacggta    7320
aatggcccgc ctggctgacc gcccaacgac ccccgcccat tgacgtcaat aatgacgtat    7380
gttcccatag taacgccaat agggactttc cattgacgtc aatgggtgga gtatttacgg    7440
taaactgccc acttggcagt acatcaagtg tatcatatgc caagtacgcc cctattgac    7500 gtcaatgacg gtaaatggcc cgcctggcat tatgcccagt acatgaccctt atgggacttt    7560 cctacttggc agtacatcta cgtattagtc atcgctatta ccatggtgat gcggttttgg    7620
cagtacatca atgggcgtgg atagcggttt gactcacggg gatttccaag tctccacccc    7680
attgacgtca atgggagttt gttttggcac caaaatcaac gggactttcc aaaatgtcgt    7740
aacaactccg ccccattgac gcaaatgggc ggtaggcgtg tacggtggga ggtctatata    7800
agcagagctg gtttagtgaa ccgtcagatc cgctagcgct accggactca gatctcgagc    7860
```

-continued

```
tcaagcttcg aattctgcag tcgacccacc atggctcttt caaacaagtt tatcggagat    7920
gacatgaaaa tgacctacca tatggatggc tgtgtcaatg ggcattactt taccgtcaaa    7980
ggtgaaggca gcgggaagcc atacgaaggg acgcagacct cgactttaa agtcaccatg     8040 gccaacggtg ggcccttgc attctccttt gacatactat ctacagtgtt catgtatgga     8100
aatcgatgct ttactgcgta tcctaccagt atgcccgact atttcaaaca agcatttcct    8160 gacgaatgt catatgaaag gacttttacc tatgaagatg gaggagttgc tacagccagt     8220
tgggaaataa gccttaaagg caactgcttt gagcacaaat ccacgtttca tggagtgaac    8280
tttcctgctg atggacctgt gatggcgaag atgacaactg gttgggaccc atcttttgag    8340
aaaatgactg tctgcgatgg aatattgaag ggtgatgtca ccgcgttcct catgctgcaa    8400
ggaggtggca attacagatg ccaattccac acttcttaca agacaaaaaa accggtgacg    8460
atgccaccaa accatgcggt ggaacatcgc attgcgagga ccgaccttga caaggtggc    8520 aacagtgttc agctgacgga gcacgctgtt gcacatataa cctctgttgt cccttctag    8580 cggccgcgat aatcaacctc tggattacaa aatttgtgaa agattgactg gtattcttaa    8640
ctatgttgct cctttacgc tatgtggata cgctgcttta atgcctttgt atcatgctat     8700
tgcttcccgt atggctttca ttttctcctc cttgtataaa tcctggttgc tgtctcttta    8760
tgaggagttg tggcccgttg tcaggcaacg tggcgtggtg tgcactgtgt ttgctgacgc    8820 aaccccccact ggttggggca ttgccaccac ctgtcagctc cttccggga ctttcgcttt    8880 cccctccct attgccacgg cggaactcat cgccgcctgc cttgcccgct gctggacagg    8940
ggctcggctg ttgggcactg acaattccgt ggtgttgtcg gggaagctga cgtccttcc    9000 atggctgctc gcctgtgttg ccacctggat tctgcgcggg acgtccttct gctacgtccc    9060
ttcggccctc aatccagcgg accttccttc ccgcggcctg ctgccggctc tgcggcctct    9120
tccgcgtctt cgccttcgcc ctcagacgag tcggatctcc cttttgggccg cctccccgca    9180 tcggacgcgt ggtacccttta agaccaatga cttacaaggc agctgtagat cttagccact    9240
ttttaaaaga aaaggggggga ctggaagggc taattcactc ccaacgaaga caagatctgc    9300 ttttttgcttg tactgggtct ctctggttag accagatctg agcctgggag ctctctggct    9360
aactagggaa cccactgctt aagcctcaat aaagcttgcc ttgagtgctt caagtagtgt    9420
gtgcccgtct gttgtgtgac tctggtaact agagatccct cagacccttt tagtcagtgt    9480
ggaaaatctc tagcagtagt agttcatgtc atcttattat tcagtattta aacttgcaa    9540 agaaatgaat atcagagagt gagaggaact tgtttattgc agcttataat ggttacaaat    9600
aaagcaatag catcacaaat ttcacaaata aagcattttt ttcactgcat tctagttgtg    9660
gtttgtccaa actcatcaat gtatcttatc atgtctggct ctagctatcc cgcccctaac    9720
tccgcccatc ccgcccctaa ctccgcccag ttccgcccat tctccgcccc atggctgact    9780
aatttttttt atttatgcag aggccgaggc cgcctcggcc tctgagctat tccagaagta    9840
gtgaggaggc ttttttggag gcctaggac gtacccaatt cgccctatag tgagtcgtat    9900
tacgcgcgct cactggccgt cgttttacaa cgtcgtgact gggaaaaccc tggcgttacc    9960
caacttaatc gccttgcagc acatccccct tcgccagctg gcgtaatag cgaagaggcc    10020 cgcaccgatc gcccttccca cagttgcgc agcctgaatg gcgaatggga cgcgccctgt    10080
agcggcgcat taagcgcggc gggtgtggtg gttacgcgca gcgtgaccgc tacacttgcc    10140
agcgccctag cgcccgctcc tttcgctttc ttcccttcct ttctcgccac gttcgccggc    10200
tttccccgtc aagctctaaa tcgggggctc cctttagggt tccgatttag tgctttacgg    10260
```

```
cacctcgacc ccaaaaaact tgattagggt gatggttcac gtagtgggcc atcgccctga   10320
tagacggttt ttcgcccttt gacgttggag tccacgttct ttaatagtgg actcttgttc   10380
caaactggaa caacactcaa ccctatctcg gtctattctt ttgatttata agggattttg   10440
ccgatttcgg cctattggtt aaaaaatgag ctgatttaac aaaaatttaa cgcgaatttt   10500
aacaaaatat taacgcttac aatttaggtg cacttttcg gggaaatgtg cgcggaaccc    10560
ctatttgttt atttttctaa atacattcaa atatgtatcc gctcatgaga caataaccct   10620
gataaatgct tcaataatat tgaaaaagga agagtatgag tattcaacat ttccgtgtcg   10680
cccttattcc cttttttgcg gcattttgcc ttcctgtttt tgctcaccca gaaacgctgg   10740
tgaaagtaaa agatgctgaa gatcagttgg gtgcacgagt gggttacatc gaactggatc   10800
tcaacagcgg taagatcctt gagagttttc gccccgaaga acgttttcca atgatgagca   10860
cttttaaagt tctgctatgt ggcgcggtat tatcccgtat tgacgccggg caagagcaac   10920
tcggtcgccg catacactat tctcagaatg acttggttga gtactcacca gtcacagaaa   10980
agcatcttac ggatggcatg acagtaagag aattatgcag tgctgccata accatgagtg   11040
ataacactgc ggccaactta cttctgacaa cgatcgagg accgaaggag ctaaccgctt    11100
ttttgcacaa catgggggat catgtaactc gccttgatcg ttgggaaccg gagctgaatg   11160
aagccatacc aaacgacgag cgtgacacca cgatgcctgt agcaatggca acaacgttgc   11220
gcaaactatt aactggcgaa ctacttactc tagcttcccg gcaacaatta atagactgga   11280
tggaggcgga taaagttgca ggaccacttc tgcgctcggc ccttccggct ggctggttta   11340
ttgctgataa atctggagcc ggtgagcgtg ggtctcgcgg tatcattgca gcactggggc   11400
cagatggtaa gccctcccgt atcgtagtta tctacacgac ggggagtcag gcaactatgg   11460
atgaacgaaa tagacagatc gctgagatag gtgcctcact gattaagcat tggtaactgt   11520
cagaccaagt ttactcatat atactttaga ttgatttaaa acttcatttt taatttaaaa   11580
ggatctaggt gaagatcctt tttgataatc tcatgaccaa aatcccttaa cgtgagtttt   11640
cgttccactg agcgtcagac cccgtagaaa agatcaaagg atcttcttga gatcctttt    11700 ttctgcgcgt aatctgctgc ttgcaaacaa aaaaaccacc gctaccagcg gtggtttgtt   11760
tgccggatca agagctacca actctttttc cgaaggtaac tggcttcagc agagcgcaga   11820
taccaaatac tgttcttcta gtgtagccgt agttaggcca ccacttcaag aactctgtag   11880
caccgcctac atacctcgct ctgctaatcc tgttaccagt ggctgctgcc agtggcgata   11940
agtcgtgtct taccgggttg gactcaagac gatagttacc ggataaggcg cagcggtcgg   12000
gctgaacggg gggttcgtgc acacagccca gcttggagcg aacgacctac accgaactga   12060
gatacctaca gcgtgagcta tgagaaagcg ccacgcttcc cgaagggaga aaggcggaca   12120
ggtatccggt aagcggcagg gtcggaacag gagagcgcac gagggagctt ccaggggaa    12180 acgcctggta tctttatagt cctgtcgggt ttcgccacct ctgacttgag cgtcgatttt   12240
tgtgatgctc gtcagggggg cggagcctat ggaaaaacgc cagcaacgcg gcctttttac   12300
ggttcctggc cttttgctgg ccttttgctc acatgttctt tcctgcgtta tcccctgatt   12360
ctgtggataa ccgtattacc gcctttgagt gagctgatac cgctcgccgc agccgaacga   12420
ccgagcgcag cgagtcagtg agcgaggaag cggaagagcg cccaatacgc aaaccgcctc   12480
tccccgcgcg ttggccgatt cattaatgca gctggcacga caggtttccc gactggaaag   12540
cgggcagtga gcgcaacgca attaatgtga gttagctcac tcattaggca ccccaggctt   12600
```

```
tacactttat gcttccggct cgtatgttgt gtggaattgt gagcggataa caatttcaca    12660
caggaaacag ctatgaccat gattacgcca agcgcgcaat taaccctcac taaagggaac    12720
aaaagctgga gctgcaagct t                                              12741

<210> SEQ ID NO 3
<211> LENGTH: 11626
<212> TYPE: DNA
<213> ORGANISM: Artificial Sequence
<220> FEATURE:
<223> OTHER INFORMATION: Synthetic polynucleotide

<400> SEQUENCE: 3
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac cttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcggggggaga     600 attagatcgc gatgggaaaa aattcggtta aggccagggg gaagaaaaaa atataaatta     660
aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
aagaccaccg cacagcaagc ggccgctgat cttcagacct ggaggaggag atatgaggga     960
caattggaga agtgaattat ataaatataa agtagtaaaa attgaaccat taggagtagc    1020
acccaccaag gcaaagagaa gagtggtgca gagagaaaaa agagcagtgg gaataggagc    1080
tttgttcctt gggttcttgg gagcagcagg aagcactatg ggcgcagcgt caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaagaatga    1500 acaagaatta ttggaattag ataaatgggc aagtttgtgg aattggttta acataacaaa    1560
ttggctgtgg tatataaaat tattcataat gatagtagga ggcttggtag gtttaagaat    1620 agttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcgata    1800
ctagtaattt ttctgcagaa aacgtacccg ggatcctct aggatcccac cgaaaggttg    1860
ctccttaaca caggctaagg accagcttct ttgggagaga acagacgcag gggcgggagg    1920
```

```
gaaaaaggga gaggcagacg tcacttcccc ttggcggctc tggcagcaga ttggtcggtt    1980
gagtggcaga aaggcagacg gggactgggc aaggcactgt cggtgacatc acggacaggg    2040
cgacttctat gtagatgagg cagcgcagag gctgctgctt cgccacttgc tgcttcgcca    2100
cgaaggagtt cccgtgccct gggagcgggt tcaggaccgc ggatcggaag tgagaatccc    2160
agctgtgtgt cagggctgga aagggctcgg gagtgcgcgg ggcaagtgac cgtgtgtgta    2220
aagagtgagg cgtatgaggc tgtgtcgggg cagagcccga agatccgggt tgcggagggt    2280
gggcctggga ggggtggtgg ccattttttg tctaacccta actgagaagg gcgtaggcgc    2340
cgtgcttttg ctccccgcgc gctgttttc tcgctgactt tcagcgggcg aaaagcctc     2400 ggcctgccgc cttccaccgt tcattctaga gcaaacaaaa aatgtcagct gctggcccgt    2460
tcgcccctcc cggggacctg cggcgggtcg cctgcccagc ccccgaaccc cgcctggagg    2520
ccgcggtcgg cccggggctt ctccggaggc acccactgcc accgcgaaga gttgggctct    2580
gtcagccgcg ggtctctcgg gggcgagggc gaggttcagg cctttcaggc cgcaggaaga    2640
ggaacggagc gagtccccgc gcgcggcgcg attccctgag ctgtgggacg tgcacccagg    2700
actcggctca cacatgcagt tcgctttcct gttggtgggg ggaacgccga tcgtgcgcat    2760
ccgtcacccc tcgccggcaa tgggggcttg tgaaccccca aacctgactg actgggccag    2820
tgtgctgcaa attggcagga gacgtgaagg cacctccaaa gtcgactttc tggagtttca    2880
aaaacagacc gtacatgtcc gcggtcgcga cgtacctacc gggtagggga ggcgcttttc    2940
ccaaggcagt ctggagcatg cgctttagca gccccgctgg gcacttggcg ctacacaagt    3000
ggcctctggc ctcgcacaca ttccacatcc accggtaggc gccaaccggc tccgttcttt    3060
ggtggcccct tcgcgccacc ttctactcct cccctagtca ggaagttccc ccccgccccg    3120
cagctcgcgt cgtgcaggac gtgacaaatg gaagtagcac gtctcactag tctcgtgcag    3180
atggacagca ccgctgagca atggaagcgg gtaggccttt ggggcagcgg ccaatagcag    3240 cttgctcct tcgctttctg ggctcagagg ctgggaaggg gtgggtccgg gggcgggctc     3300
aggggcgggc tcaggggcgg ggcggcgcgcc cgaagtcctc cggaggcccg gcattctgca    3360
cgcttcaaaa gcgcacgtct gccgcgctgt tctcctcttc ctcatctccg ggcctttcga    3420
ctctagacac gtgttgacaa ttaatcatcg gcatagtata tcggcatagt ataatacgac    3480
aaggtgagga actaaaccat ggccaagcct ttgtctcaag aagaatccac cctcattgaa    3540
agagcaacgg ctacaatcaa cagcatcccc atctctgaag actacagcgt cgccagcgca    3600
gctctctcta gcgacggccg catcttcact ggtgtcaatg tatatcattt tactggggga    3660
ccttgtgcag aactcgtggt gctgggcact gctgctgctg cggcagctgg caacctgact    3720
tgtatcgtcg cgatcggaaa tgagaacagg ggcatcttga gccctgcgg acggtgccga    3780 caggtgcttc tcgatctgca tcctgggatc aaagccatag tgaaggacag tgatggacag    3840
ccgacggcag ttgggattcg tgaattgctg ccctctggtt atgtgtggga gggctaagca    3900
caattcgagc tcggtacgcg tatcgatggc gccagctgca ggcggccgcc atatgcatcc    3960
taggcctatt aatattccgg agtatacgta gccggctaac gttaacaacc ggtacgatgc    4020
attagttatt aatagtaatc aattacgggg tcattagttc atagcccata tatgagttc     4080 cgcgttacat aacttacggt aaatggcccg cctggctgac cgcccaacga ccccgcccca    4140
ttgacgtcaa taatgacgta tgttcccata gtaacgccaa tagggacttt ccattgacgt    4200
caatgggtgg agtatttacg gtaaactgcc cacttggcag tacatcaagt gtatcatatg    4260
```

-continued

```
ccaagtacgc cccctattga cgtcaatgac ggtaaatggc ccgcctggca ttatgcccag    4320
tacatgacct tatgggactt tcctacttgg cagtacatct acgtattagt catcgctatt    4380
accatggtga tgcggttttg gcagtacatc aatgggcgtg gatagcggtt tgactcacgg    4440
ggatttccaa gtctccaccc cattgacgtc aatgggagtt tgttttggca ccaaaatcaa    4500
cgggactttc caaaatgtcg taacaactcc gccccattga cgcaaatggg cggtaggcgt    4560
gtacggtggg aggtctatat aagcagagct ggtttagtga accgtcagat ccgctagccc    4620
caccatgccg cgcgctcccc gctgccgagc cgtgcgctcc ctgctgcgca gccactaccg    4680
cgaggtgctg ccgctggcca cgttcgtgcg gcgcctgggg cccagggct ggcggctggt     4740
gcagcgcggg gacccggcgg cttttccgcgc gctggtggcc cagtgcctgg tgtgcgtgcc    4800
ctggacgca cggccgcccc ccgccgcccc ctccttccgc caggtgtcct gcctgaagga     4860
gctggtggcc cgagtgctgc agaggctgtg cgagcgcggc gcgaagaacg tgctggcctt    4920
cggcttcgcg ctgctggacg gggcccgcgg gggcccccc gaggccttca ccaccagcgt     4980
gcgcagctac ctgcccaaca cggtgaccga cgcactgcgg gggagcgggg cgtggggct     5040
gctgttgcgc cgcgtgggcg acgacgtgct ggttcacctg ctggcacgct gcgcgctctt    5100
tgtgctggtg gctcccagct gcgcctacca ggtgtgcggg ccgccgctgt accagctcgg    5160
cgctgccact caggcccggc ccccgccaca cgctagtgga ccccgaaggc gtctgggatg    5220
cgaacgggcc tggaaccata gcgtcaggga ggccgggtc cccctgggcc tgccagcccc     5280
gggtgcgagg aggcgcgggg gcagtgccag ccgaagtctg ccgttgccca agaggcccag    5340
gcgtggcgct gccctgagc cggagcggac gcccgttggg caggggtcct gggcccaccc     5400
ggcaggacg cgtggaccga gtgaccgtgg tttctgtgtg gtgtcacctg ccagacccgc     5460
cgaagaagcc acctctttgg agggtgcgct ctctggcacg cgccactccc acccatccgt    5520
gggccgccag caccacgcgg gccccccatc cacatcgcgg ccaccacgtc cctgggacac    5580
gccttgtccc ccggtgtacg ccgagaccaa gcacttcctc tactcctcag gcgacaagga    5640
gcagctgcgg ccctccttcc tactcagctc tctgaggccc agcctgactg cgctcggag     5700
gctcgtggag accatctttc tgggttccag gccctggatg ccaggactc cccgcaggtt     5760
gccccgcctg ccccagcgct actggcaaat gcggcccctg tttctggagc tgcttgggaa    5820
ccacgcgcag tgccctacg gggtgctcct caagacgcac tgcccgctgc gagctgcggt    5880
cacccagca gccggtgtct gtgcccggga gaagcccag ggctctgtgg cggccccga      5940
ggaggaggac acagacccc gtcgcctggt gcagctgctc cgccagcaca gcagcccctg     6000
gcaggtgtac ggcttcgtgc gggcctgcct cgccggctg gtgcccccag gcctctgggg     6060
ctccaggcac aacgaacgcc gcttcctcag gaacaccaag aagttcatct ccctggggaa    6120
gcatgccaag ctctcgctgc aggagctgac gtggaagatg agcgtgcggg gctgcgcttg    6180
gctgcgcagg agcccagggg ttggctgtgt tccggccgca gagcaccgtc tgcgtgagga    6240
gatcctggcc aagttcctgc actggctgat gagtgtgtac gtcgtcgagc tgctcaggtc    6300
tttcttttat gtcacggaga ccacgtttca aaagaacagg ctcttttttct accggaagag    6360
tgtctgagc aagttgcaaa gcattggaat cagacagcac ttgaagaggg tgcagctgcg     6420
ggagctgtcg gaagcagagg tcaggcagca tcgggaagcc aggcccgccc tgctgacgtc    6480
cagactccgc ttcatcccca agcctgacgg gctgcggccg attgtgaaca tggactacgt    6540
cgtgggagcc agaacgttcc gcagagaaaa gagggccgag cgtctcacct ccagggtgaa    6600
ggcactgttc agcgtgctca actacgagcg ggcgcggcgc cccggcctcc tgggcgcctc    6660
```

```
tgtgctgggc ctggacgata tccacagggc ctggcgcacc ttcgtgctgc gtgtgcgggc   6720
ccaggacccg ccgcctgagc tgtactttgt caaggtggat gtgacgggcg cgtacgacac   6780
catcccccag gacaggctca cggaggtcat cgccagcatc atcaaacccc agaacacgta   6840
ctgcgtgcgt cggtatgccg tggtccagaa ggccgcccat gggcacgtcc gcaaggcctt   6900
caagagccac gtctctacct tgacagacct ccagccgtac atgcgacagt tcgtggctca   6960
cctgcaggag accagcccgc tgagggatgc cgtcgtcatc gagcagagct cctccctgaa   7020
tgaggccagc agtggcctct tcgacgtctt cctacgcttc atgtgccacc acgccgtgcg   7080
catcagggge aagtcctacg tccagtgcca ggggatcccg cagggctcca tcctctccac   7140
gctgctctgc agcctgtgct acggcgacat ggagaacaag ctgtttgcgg ggattcggcg   7200
ggacgggctg ctcctgcgtt tggtggatga tttcttgttg gtgacacctc acctcaccca   7260
cgcgaaaacc ttcctcagga ccctggtccg aggtgtccct gagtatggct gcgtggtgaa   7320
cttgcggaag acagtggtga acttccctgt agaagacgag gccctgggtg gcacggcttt   7380
tgttcagatg ccggcccacg gcctattccc ctggtgcggc ctgctgctgg atcccggac    7440
cctggaggtg cagagcgact actccagcta tgcccggacc tccatcagag ccagtctcac   7500
cttcaaccgc ggcttcaagg ctgggaggaa catgcgtcgc aaactctttg gggtcttgcg   7560
gctgaagtgt cacagcctgt ttctggattt gcaggtgaac agcctccaga cggtgtgcac   7620
caacatctac aagatcctcc tgctgcaggc gtacaggttt cacgcatgtg tgctgcagct   7680
cccatttcat cagcaagttt ggaagaaccc cacattttc ctgcgcgtca tctctgacac    7740
ggcctccctc tgctactcca tcctgaaagc caagaacgca gggatgtcgc tgggggccaa   7800
gggcgccgcc ggccctctgc cctccgaggc cgtgcagtgg ctgtgccacc aagcattcct   7860
gctcaagctg actcgacacc gtgtcaccta cgtgccactc ctgggggtcac tcaggacagc   7920
ccagacgcag ctgagtcgga agctcccggg gacgacgctg actgccctgg aggccgcagc   7980
caacccggca ctgccctcag acttcaagac catcctggac tgagtcgaaa ctcgcggccg   8040
catgcgtcga cgcgtatcga tgcatcttaa gtagatgtac ctttaagacc aatgacttac   8100
aaggcagctg tagatcttag ccacttttta aaagaaaagg ggggactgga agggctaatt   8160
cactcccaac gaagacaaga tctgcttttt gcttgtactg ggtctctctg gttagaccag   8220
atctgagcct gggagctctc tggctaacta gggaacccac tgcttaagcc tcaataaagc   8280
ttgccttgag tgcttcaagt agtgtgtgcc cgtctgttgt gtgactctgg taactagaga   8340
tccctcagac ccttttagtc agtgtggaaa atctctagca gtagtagttc atgtcatctt   8400
attattcagt atttataact tgcaaagaaa tgaatatcag agagtgagag gaacttgttt   8460
attgcagctt ataatggtta caaataaagc aatagcatca caaatttcac aaataaagca   8520
ttttttttcac tgcattctag ttgtggtttg tccaaactca tcaatgtatc ttatcatgtc   8580
tggctctagc tatcccgccc ctaactccgc ccatcccgcc cctaactccg cccagttccg   8640
cccattctcc gccccatggc tgactaattt tttttattta tgcagaggcc gaggccgcct   8700
cggcctctga gctattccag aagtagtgag gaggcttttt tggaggccta gggacgtacc   8760
caattcgccc tatagtgagt cgtattacgc gcgctcactg gccgtcgttt tacaacgtcg   8820
tgactgggaa aaccctggcg ttacccaact taatcgcctt gcagcacatc cccctttcgc   8880
cagctggcgt aatagcgaag aggcccgcac cgatcgccct tcccaacagt tgcgcagcct   8940
gaatggcgaa tgggacgcgc cctgtagcgg cgcattaagc gcggcgggtg tggtggttac   9000
```

```
gcgcagcgtg accgctacac ttgccagcgc cctagcgccc gctcctttcg ctttcttccc      9060
ttcctttctc gccacgttcg ccggctttcc ccgtcaagct ctaaatcggg ggctcccttt      9120
agggttccga tttagtgctt tacggcacct cgaccccaaa aaacttgatt agggtgatgg      9180
ttcacgtagt gggccatcgc cctgatagac ggttttttcgc cctttgacgt tggagtccac     9240
gttctttaat agtggactct tgttccaaac tggaacaaca ctcaaccta tctcggtcta      9300 ttcttttgat ttataaggga ttttgccgat ttcggcctat tggttaaaaa atgagctgat     9360
ttaacaaaaa tttaacgcga attttaacaa aatattaacg cttacaattt aggtggcact      9420
tttcggggaa atgtgcgcgg aaccctatt tgtttatttt tctaaataca ttcaaatatg      9480
tatccgctca tgagacaata accctgataa atgcttcaat aatattgaaa aaggaagagt      9540
atgagtattc aacatttccg tgtcgccctt attccctttt ttgcggcatt ttgccttcct      9600 gttttgctc acccagaaac gctggtgaaa gtaaaagatg ctgaagatca gttgggtgca      9660
cgagtgggtt acatcgaact ggatctcaac agcggtaaga tccttgagag ttttcgcccc      9720
gaagaacgtt ttccaatgat gagcactttt aaagttctgc tatgtggcgc ggtattatcc      9780
cgtattgacg ccgggcaaga gcaactcggt cgccgcatac actattctca gaatgacttg      9840
gttgagtact caccagtcac agaaaagcat cttacggatg gcatgacagt aagagaatta      9900
tgcagtgctg ccataaccat gagtgataac actgcggcca acttacttct gacaacgatc      9960
ggaggaccga aggagctaac cgcttttttg cacaacatgg gggatcatgt aactcgcctt     10020
gatcgttggg aaccggagct gaatgaagcc ataccaaacg acgagcgtga ccaccgatg     10080 cctgtagcaa tggcaacaac gttgcgcaaa ctattaactg gcgaactact tactctagct      10140
tcccggcaac aattaataga ctggatggag gcggataaag ttgcaggacc acttctgcgc      10200
tcggcccttc cggctggctg gtttattgct gataaatctg gagccggtga gcgtgggtct      10260
cgcggtatca ttgcagcact ggggccagat ggtaagccct cccgtatcgt agttatctac      10320
acgacgggga gtcaggcaac tatggatgaa cgaaatagac agatcgctga gataggtgcc      10380
tcactgatta agcattggta actgtcagac caagtttact catatatact ttagattgat     10440
ttaaaacttc attttaatt taaaaggatc taggtgaaga tcctttttga taatctcatg      10500
accaaaatcc cttaacgtga gttttcgttc cactgagcgt cagaccccgt agaaaagatc      10560
aaaggatctt cttgagatcc ttttttttctg cgcgtaatct gctgcttgca acaaaaaaa      10620 ccaccgctac cagcggtggt ttgtttgccg gatcaagagc taccaactct ttttccgaag      10680
gtaactggct tcagcagagc gcagatacca aatactgttc ttctagtgta gccgtagtta      10740
ggccaccact tcaagaactc tgtagcaccg cctacatacc tcgctctgct aatcctgtta      10800
ccagtggctg ctgccagtgg cgataagtcg tgtcttaccg ggttggactc aagacgatag      10860
ttaccggata aggcgcagcg gtcgggctga acggggggtt cgtgcacaca gcccagcttg      10920
gagcgaacga cctacaccga actgagatac ctacagcgtg agctatgaga aagcgccacg      10980
cttcccgaag ggagaaaggc ggacaggtat ccggtaagcg gcagggtcgg aacaggagag     11040
cgcacgaggg agcttccagg gggaaacgcc tggtatcttt atagtcctgt cgggtttcgc     11100
cacctctgac ttgagcgtcg atttttgtga tgctcgtcag ggggcggag cctatggaaa     11160 aacgccagca acgcggcctt tttacggttc ctggcctttt gctggccttt tgctcacatg      11220
ttctttcctg cgttatcccc tgattctgtg ataaccgta ttaccgcctt tgagtgagct      11280
gataccgctc gccgcagccg aacgaccgag cgcagcgagt cagtgagcga ggaagcggaa      11340
gagcgcccaa tacgcaaacc gcctctcccc gcgcgttggc cgattcatta atgcagctgg     11400
```

```
cacgacaggt ttcccgactg gaaagcgggc agtgagcgca acgcaattaa tgtgagttag    11460
ctcactcatt aggcacccca ggctttacac tttatgcttc cggctcgtat gttgtgtgga    11520
attgtgagcg gataacaatt tcacacagga aacagctatg accatgatta cgccaagcgc    11580
gcaattaacc ctcactaaag ggaacaaaag ctggagctgc aagctt                   11626
```

ENHANCING HEALTH IN MAMMALS USING TELOMERASE REVERSE TRANSCRIPTASE GENE THERAPY

INTRODUCTION

The improvement of health during aging is of interest in aging research. Markers of aging include conditions such as epithelial barrier fitness, osteoporosis, glucose intolerance with insulin insensitivity, loss of memory, and neuromuscular degeneration associated with loss of neuromuscular coordination. For example, bone loss is a well-characterized sign of the aging progress both in mammals including humans which results from bone resorption due to osteoblast insufficiency. Therefore, methods that increase life span and ameliorate various age-related parameters are of interest.

Telomeres are regions of repetitive DNA found at the ends of the chromosomes of most eukaryotes. For example, human telomeres include many kilobases of (TTAGGG)n and are associated with various proteins. Small portions of these terminal sequences of telomeric DNA are lost from the tips of the chromosomes during the S phase of the cell cycle because of incomplete DNA replication. Many human cells progressively lose terminal sequences with cell division, a loss that correlates with the apparent absence of telomerase in these cells. The resulting telomere shortening limits cellular lifespan.

Telomerase is a ribonucleoprotein that synthesizes telomeric DNA. Telomerase is made up of two components: (1) an essential structural RNA component (TR or TER) (in humans the component is referred to as hTR or hTER), and (2) a catalytic protein (telomerase reverse transcriptase or TERT) (in humans the component is referred to as hTERT). Telomerase works by adding multiple DNA sequence repeats to the 3' end of DNA in the telomere region, where hTER serves as the template for nucleotide incorporation, and TERT as the catalyst. Both the catalytic protein component and the RNA template component of telomerase are activity-limiting components.

SUMMARY

Methods of treating an age-related disorder or condition in a subject are provided. Aspects of the methods include administering to the subject a nucleic acid vector including a coding sequence for telomerase reverse transcriptase (TERT) and/or telomerase RNA (TR). Gene therapy methods are also provided. Aspects of the invention further include compositions, e.g., nucleic acid vectors and kits, etc., that find use in methods of the invention.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
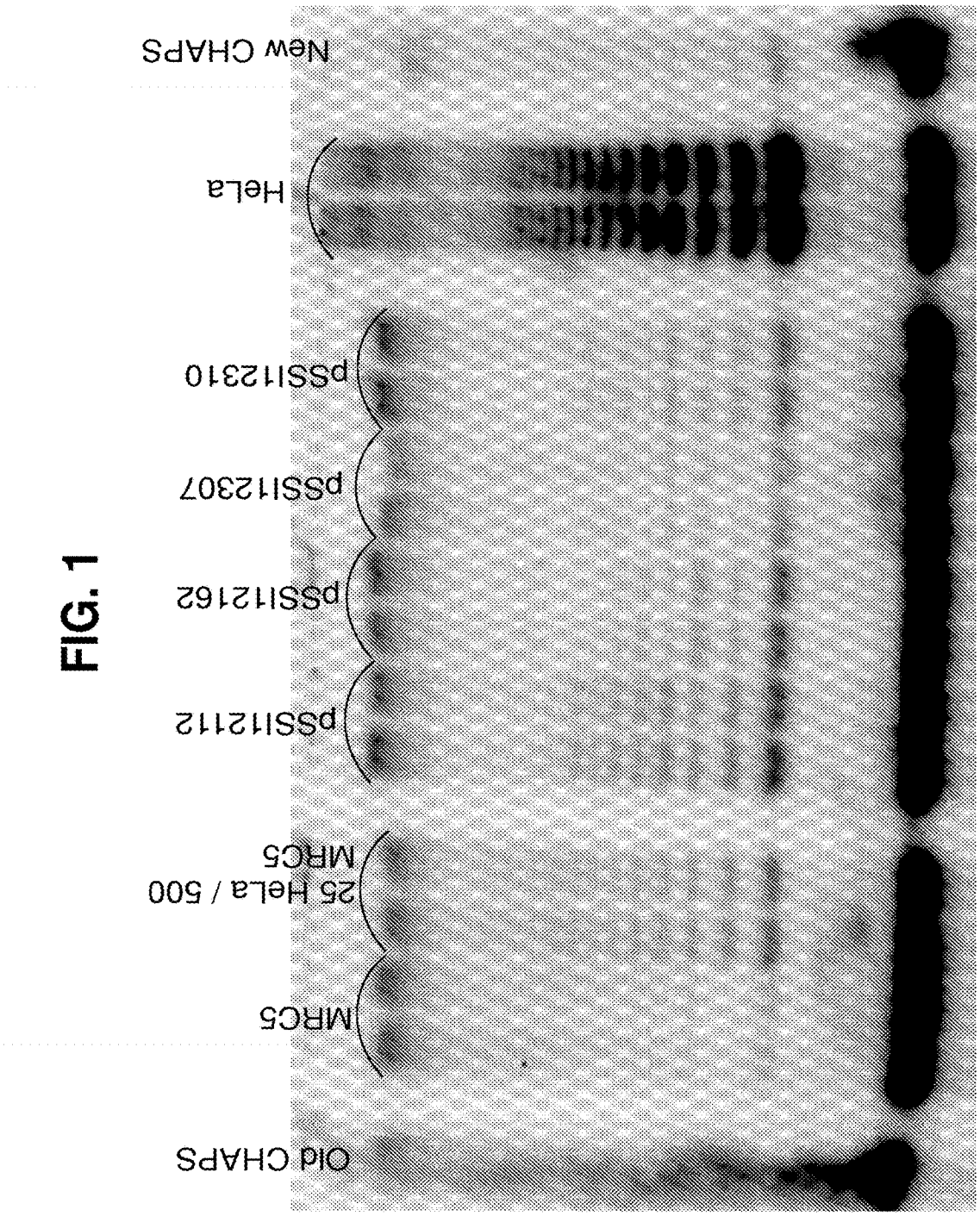
FIG. 1 depicts the results of a TRAP Assay using the vectors pSSI12112, pSSI12162, pSSI112307 and pSSI12310 where sample cells are collected at 7 days post BSD selection, 17 days post infection.

As summarized above, aspects of the invention include methods of treating an age-related disorder in a subject. Aspects of the methods include administering to the subject a nucleic acid vector including a coding sequence for telomerase reverse transcriptase (TERT). In some cases, the vector may include a coding sequence for telomerase RNA (TR). Gene therapy methods that utilize the subject vectors are also provided. Embodiments of the invention include compositions, e.g., nucleic acid vectors and kits, etc., that find use in the subject methods.

The subject methods may lead to increase the expression of telomerase reverse transcriptase and/or telomerase RNA when administered to adult mammals. Administration of the vectors to the subject may extend the lifespan of the subject (e.g., average or maximum lifespan), and may ameliorate one or more markers of ageing, including but not limited to epithelial barrier fitness, osteoporosis, glucose intolerance with insulin insensitivity, loss of memory, and neuromuscular degeneration associated with loss of neuromuscular coordination. The effect may be achieved without increasing the incidence of cancer (malignant neoplastic disease), as assessed by the number of spontaneous neoplasms evident among the population treated.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Vectors

As summarized above, one aspect of the invention is a nucleic acid vector. Application of the subject vector to a subject, e.g. using any convenient method such as a gene therapy method, may result in expression of one or more coding sequences of interest in cells of the subject, to produce a biologically active product that may modulate a biological activity of the cell. In some cases, the vector is a nucleic acid vector comprising a coding sequence for telomerase reverse transcriptase (TERT). In some cases, the nucleic acid vector comprises a coding sequence for one or more telomerase components, such as TERT and telomerase RNA (TR). In some embodiments, the vector does not include a cancer suppressing sequence.

In some instances, the vector comprises a coding sequence for telomerase reverse transcriptase (TERT) suitable for use in gene therapy. Gene therapy vectors of interest include any kind of particle that comprises a polynucleotide fragment encoding the telomerase reverse transcriptase (TERT) protein, operably linked to a regulatory element such as a promoter, which allows the expression of a functional TERT protein demonstrating telomerase reverse transcriptase activity in the targeted cells. In some cases, TERT is encoded by the nucleic acid sequence as set forth in SEQ ID NO:1 of WO2012001170 or SEQ ID NO:3 of WO2012001170, or is an active fragment or functional equivalent of TERT. In some instances, the vector include a regulatory sequence which is a constitutive promoter such as the cytomegalovirus (CMV) promoter.

The TERT and/or TR sequence used in the gene therapy vector may be derived from the same species as the subject. Any convenient TERT and/or TR sequences, or fragments or functional equivalents thereof, may be utilized in the subject vectors, including sequences from any convenient animal, such as a primate, ungulate, cat, dog, or other domestic pet or domesticated mammal, rabbit, pig, horse, sheep, cow, or a human. For example, gene therapy in humans may be carried out using the human TERT sequence. In some embodiments, the TERT and/or TR sequence is not a murine sequence.

As used herein, "functional equivalent" refers to a nucleic acid molecule that encodes a polypeptide that has TERT activity or a polypeptide that has TERT activity. The functional equivalent may displays 50%, 60%, 70%, 80%, 90%, 95%, 98%, 99%, 100% or more activity compared to a parent TERT sequence. Functional equivalents may be artificial or naturally-occurring. For example, naturally-occurring variants of the TERT sequence in a population fall within the scope of functional equivalent. TERT sequences derived from other species also fall within the scope of the term "functional equivalent", e.g., a murine TERT sequence. In a particular embodiment, the functional equivalent is a nucleic acid with a nucleotide sequence having at least 75%, 80%, 85%, 90%, 95%, 96%, 97%, 98%, 99%, 99.5%, 99.9% identity to the parent sequence. In a further embodiment, the functional equivalent is a polypeptide with an amino acid sequence having at least 75%, 80%, 85%, 90%, 95%, 96%, 97%, 98%, 99%, 99.5%, 99.9% identity to a parent sequence. In the case of functional equivalents, sequence identity should be calculated along the entire length of the nucleic acid. Functional equivalents may contain one or more, e.g. 2, 3, 4, 5, 10, 15, 20, 30 or more, nucleotide insertions, deletions and/or substitutions when compared to a parent sequence.

The term "functional equivalent" also encompasses nucleic acid sequences that encode a TERT polypeptide with at least 75%, 80%, 85%, 90%, 95%, 96%, 97%, 98%, 99%, 99.5%, 99.9% sequence identity to the parent amino acid sequence, but that show little homology to the parent nucleic acid sequence because of the degeneracy of the genetic code.

As used herein, the term "active fragment" refers to a nucleic acid molecule that encodes a polypeptide that has TERT activity or polypeptide that has TERT activity, but which is a fragment of the nucleic acid as set forth in the parent polynucleotide sequence or the amino acid sequence as set forth in parent polypeptide sequence. An active fragment may be of any size provided that TERT activity is retained. A fragment will have at least 75%, 80%, 85%, 90%, 95%, 96%, 97%, 98%, 99%, 99.5%, 100% identity to the parent sequence along the length of the alignment between the shorter fragment and longer parent sequence.

Fusion proteins including these fragments can be comprised in the nucleic acid vectors needed to carry out the invention. For example, an additional 5, 10, 20, 30, 40, 50 or even 100 amino acid residues from the polypeptide sequence, or from a homologous sequence, may be included at either or both the C terminal and/or N terminus without prejudicing the ability of the polypeptide fragment to fold correctly and exhibit biological activity. Sequence identity may be calculated by any one of the various methods in the art, including for example BLAST (Altschul S F, Gish W, Miller W, Myers E W, Lipman D J (1990). "Basic local alignment search tool". J Mol Biol 215 (3): 403-410) and PASTA (Lipman, D J; Pearson, W R (1985). "Rapid and sensitive protein similarity searches". Science 227 (4693): 1435-41; http://fasta.bioch.virginia.edu/fasta www2/fasta list2.shtml) and variations on these alignment programs.

The vector may further include one or more regulatory sequences. Any convenient regulatory sequences or promoter sequences may be utilized in the subject vectors, e.g., as described herein. In some embodiments, the regulatory sequence that is operatively linked to the coding sequence (e.g., the TERT and/or TR sequence) is the cytomegalovirus promoter (CMV), although any other convenient regulatory sequences may be utilized.

Viral Vectors

Any convenient viruses may be utilized in delivering the vector of interest to the subject. Viruses of interest include, but are not limited to a retrovirus, an adenovirus, an adeno-associated virus (AAV), a herpes simplex virus and a lentivirus. Viral gene therapy vectors are well known in the art, see e.g., Heilbronn & Weger (2010) Handb Exp Pharmacal. 197:143-70. Vectors of interest include integrative and non-integrative vectors such as those based on retroviruses, adenoviruses (AdV), adeno-associated viruses (AAV), lentiviruses, pox viruses, alphaviruses, and herpes viruses.

In some cases, non-integrative viral vectors, such as AAV, may be utilized. In one aspect, non-integrative vectors do not cause any permanent genetic modification. The vectors may be targeted to adult tissues to avoid having the subjects under the effect of constitutive telomerase expression from early stages of development. In some instances, non-integrative vectors effectively incorporate a safety mechanism to avoid over-proliferation of TERT expressing cells. The cells may lose the vector (and, as a consequence, the telomerase expression) if they start proliferating quickly.

Non-integrative vectors of interest include those based on adenoviruses (AdV) such as gutless adenoviruses, adeno-associated viruses (AAV), integrase deficient lentiviruses, pox viruses, alphaviruses, and herpes viruses. In certain embodiments, the non-integrative vector used in the invention is an adeno-associated virus-based non-integrative vector, similar to natural adeno-associated virus particles. Examples of adena-associated virus-based non integrative vectors include vectors based on any AAV serotype, i.e. AAVI, AAV2, AAV3, AAV4, AAV5, AAV6, AAV7, AAV8, AAV9, AAVIO, AAVII and pseudotyped AAV. Vectors of interest include those capable of transducing a broad range of tissues at high efficiency, with poor immunogenicity and an excellent safety profile. In some cases, the vectors transduce post-mitotic cells and can sustain long-term gene expression (up to several years) both in small and large animal models of age-related disorders.

Methods

As summarized above, aspects of the invention include methods of administering a nucleic acid vector to a subject. As such, aspects of the invention include contacting the subject with a viral vector, e.g., as described above, under conditions by which expression of one or more telomerase components (such as TERT and/or TR) in the subject results in a beneficial effect on one or more aspects of the subject's health, including increased longevity, delayed osteoporosis, improved epithelial barrier fitness, improved glucose tolerance, improved memory function, and improved neuromuscular coordination. In some cases, the subject did not develop increased incidence of cancer, illustrating the safety of this type of strategy.

In gene therapy methods, genes are directly inserted into cells affected by an age-related condition so that the function of the cells is normalized by expressing the inserted genes. The gene therapy methods may be used to prevent various diseases or age-related conditions or to reinforce treatment by inserting a specific gene into a body cell and granting a new function to the body cell. One aspect in the treatment of such conditions using gene therapy is that the inserted gene be successfully delivered to the nucleus of the target cell and that the gene be expressed strongly. The gene enters the target cell through endocytosis and is transported into the nucleus to be expressed. The gene can be inserted using a carrier such as a liposome since most DNAs are destroyed when entering the cell. However, most of the liposomes are also destroyed when entering the nucleus, thereby decreasing the transporting efficiency. A virus capable of infecting a human can be treated using gene therapy because the virus effectively inserts exogeneous genes into the human body. Specifically, the gene can effectively be transported and expressed by inserting the gene for the gene therapy into the DNA of the virus using gene recombination and infecting the subject (e.g., a human) with the recombinant virus, which can be mass produced in vitro. In some cases, an adenovirus can be effectively used for the gene therapy by using a mechanism of transporting the gene into the nucleus of the target cell with a high efficiency. In addition, retroviruses are being used in many internationally permissible clinical trials (Wiley—The Journal of Gene Medicine Website: http://www.wiley.co.uk/genetherapy). Retroviruses are effective for gene therapy when inserted into cell chromosomal DNA to allow long term expression of the desired protein.

In certain instances, the expression of the TERT and/or TR following gene therapy according to the invention persists for a time of one or more weeks, such as one or more months, e.g., several months to several years.

When treating specific age related disorders, it is advantageous to target the treatment to the effected tissues. The serotype of the capsid protein of the gene therapy vector may thus be selected based on the desired site of gene therapy, e.g., skeletal muscle tissue for treating neuromuscular coordination.

Any convenient methods may be employed. Methods and vectors of interest that may be adapted for use in the subject invention include, but are not limited to the methods and vectors of WO 2012/001170 and Vidale et al. "The catalytic and the RNA subunits of human telomerase are required to immortalize equid primary fibroblasts." Chromosoma. 2012 Jul. 14. Epub, the disclosures of which are herein incorporated by reference.

In some embodiments, the method of treatment is a gene therapy method and/or the nucleic acid vector used is a gene therapy vector. Gene therapy methods and vectors are well known in the art and generally include delivering a nucleic acid encoding a therapeutically active protein to a subject. The nucleic acid may be delivered in a number of ways including delivering naked DNA such as plasmid or minicircles, the use of liposomes or cationic polymers or other engineered nano-particles containing the nucleic acid, or viral vectors that encapsidate the nucleic acid.

In a further embodiment, the gene therapy is achieved using stable transformation of organisms with an inducible expression system. In certain embodiments, this aspect of the invention does not extend to human subjects. Expression of TERT or TR can be induced at a later date following transformation, for example, once the subject is an adult or an aged adult, or begins to show signs of age-related disorders. Suitable inducible expression systems are known in the art and include the CRE-LOX recombinase based system and the tetracycline-regulated system.

In some embodiments, the present invention is limited to the expression of TERT an/or TR in adult or aged subjects. In certain embodiments, the methods and vectors are utilized with post-mitotic cells within the subjects, and avoid any increased incidence of cancer.

Any convenient subjects may be treated according to the subject methods. The subject may be an adult animal, such as an adult mammal. The mammal may be a primate, ungulate, cat, dog, domestic pet or domesticated mammal. In some cases, the mammal may be a rabbit, pig, horse, sheep, cow, cat or dog, or a human. In certain embodiments the subject is not a murine mammal. An adult subject treated according to the invention may be aged. The term "aged" is applied to an individual who is older than the period of life during which the individuals of its species are generally healthy and free of chronic illness. According to the present application, an "adult" should be a fully developed individual who has attained reproductive ability, is fertile, or who evidences secondary sex characteristics. As used herein, the term adult when applied to humans, for example, describes early adulthood commencing at around 20 years of age and extending to 39; middle adulthood (40 to 59) and late adulthood (60+). As a comparison, a one year old mouse can be considered to be approximately equivalent in age to a 45 year old human. A 2 year old mouse can be considered to be approximately equivalent to an 80 year old human.

The particular protocol that is employed may vary. Administration of the vectors may be achieved using any convenient protocol. Vectors as described above (e.g., retroviral vectors and lentiviral vectors) may be administered in vivo to subjects by any convenient route. The term "administration" refers to the route of introduction of a formulated vector into the body. For example, administration may be intravenous, intramuscular, topical, oral, or by gene gun or hypospray instrumentation. Thus, administration can be direct to a target tissue or through systemic delivery. Administration directly to the target tissue can involve needle injection, hypospray, electroporation, or the gene gun. See, e.g., WO 93/18759, hereby incorporated by reference herein. Alternatively, vectors of the invention can be administered ex vivo or in vitro to cells or tissues using any convenient transfection techniques.

The vectors of the invention can also be transduced into host cells, including but not limited to, embryonic stem cells, somatic stem cells, or progenitor cells. Examples of progenitor host cells which can be transduced by the vectors of the invention include precursors of erythrocytes and hematopoietic stem cells. In another embodiment, the host cell is an erythrocyte. Transduced host cells can be used as a method of achieving erythroid-specific expression of the gene of interest in the treatment of hemoglobinopathies.

In some embodiments, the method does not include concomitant use of a cancer suppressor.

The step of facilitating the production of infectious viral particles in the cells may be carried out using conventional techniques, such as standard cell culture growth techniques. If desired by the skilled artisan, lentiviral stock solutions may be prepared using the vectors and methods of the present invention. Methods of preparing viral stock solutions are known in the art and are illustrated by, e.g., Y. Soneoka et al. (1995) Nucl. Acids Res. 23:628-633, and N. R. Landau et al. (1992) J. Virol. 66:5110-5113. In a method of producing a stock solution in the present invention, lentiviral-permissive cells (referred to herein as producer cells) are transfected with the vector system of the present invention. The cells are then grown under suitable cell culture conditions, and the lentiviral particles collected from either the cells themselves or from the cell media as described above. Suitable producer cell lines include, but are not limited to, the human embryonic kidney cell line 293, the equine dermis cell line NBL-6, and the canine fetal thymus cell line Cf2TH.

The step of collecting the infectious virus particles also can be carried out using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art.

Other methods relating to the use of viral vectors in gene therapy can be found in, e.g., Kay, M. A. (1997) Chest 111(6 Supp.): 138S-142S; Ferry, N. and Heard, J. M. (1998) Hum. Gene Ther. 9:1975-81; Shiratory, Y. et al. (1999) Liver 19:265-74; Oka, K. et al. (2000) Curr. Opin. Lipidol. 11:179-86; Thule, P. M. and Liu, J. M. (2000) Gene Ther. 7:1744-52; Yang, N. S. (1992) Crit. Rev. Biotechnol. 12:335-56; Alt, M. (1995) J. Hepatol. 23:746-58; Brody, S. L. and Crystal, R. G. (1994) Ann. N.Y. Acad. Sci. 716:90-101; Strayer, D. S. (1999) Expert Opin. Investig. Drugs 8:2159-2172; Smith-Arica, J. R. and Bartlett, J. S. (2001) Curr. Cardiol. Rep. 3:43-49; and Lee, H. C. et al. (2000) Nature 408:483-8.

As used herein "pharmaceutically acceptable carrier" includes any and all solvents, dispersion media, coatings, antibacterial and antifungal agents, isotonic and absorption delaying agents, and the like that are physiologically compatible. In one embodiment, the carrier is suitable for parenteral administration. Preferably, the carrier is suitable for administration directly into an affected joint. The carrier can be suitable for intravenous, intraperitoneal or intramuscular administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Another aspect of the invention pertains to pharmaceutical compositions of the vectors of the invention. In one embodiment, the composition includes a vector in a therapeutically effective amount sufficient to treat or prevent (e.g. ameliorate one or more age-related conditions), and a pharmaceutically acceptable carrier. A "therapeutically effective amount" refers to an amount effective, at dosages and for periods of time necessary, to achieve the desired therapeutic result, such as treatment or amelioration of an age-related condition. A therapeutically effective amount of vector may vary according to factors such as the disease state, age, sex, and weight of the individual, and the ability of the viral vector to elicit a desired response in the individual. Dosage regimens may be adjusted to provide the optimum therapeutic response. A therapeutically effective amount is also one in which any toxic or detrimental effects of the viral vector are outweighed by the therapeutically beneficial effects. The potential toxicity of the viral vectors of the invention can be assayed using cell-based assays or art recognized animal models and a therapeutically effective modulator can be selected which does not exhibit significant toxicity. In a preferred embodiment, a therapeutically effective amount of a viral vector is sufficient to treat or ameliorate one or more age-related conditions in as subject.

Sterile injectable solutions can be prepared by incorporating viral vector in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient plus any additional desired ingredient from a previously sterile-filtered solution thereof.

It is to be noted that dosage values may vary with the severity of the condition to be ameliorated. It is to be further understood that for any particular subject, specific dosage regimens can be adjusted over time according to the individual need and the professional judgment of the person administering or supervising the administration of the compositions, and that dosage ranges set forth herein are exemplary only and are not intended to limit the scope or practice of the claimed composition.

The amount of viral vector in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

In Vitro Methods

Also included are in vitro methods, where the subject vectors, e.g., as described above are contacted with a sample. The particular protocol that is employed may vary, e.g., depending on the sample. For in vitro protocols, contact of the vector with the sample may be achieved using any convenient protocol. In some instances, the sample includes cells that are maintained in a suitable culture medium, and the vector is introduced into the culture medium. Depending upon the nature of the vector (e.g., a viral vector), the response desired, the manner of contacting or administration, the number of cells present, various protocols may be employed. The term "sample" as used herein relates to a material or mixture of materials, typically, although not necessarily, in fluid form, containing one or more components of interest.

Utility

The vectors and methods of the invention, e.g., as described above, find use in a variety of applications. Applications of interest include, but are not limited to: research applications and therapeutic applications. Methods of the invention find use in a variety of different applications including any convenient application where the subject is experiencing one or more age-related conditions. In some cases, age-related disorders or conditions that may be modulated or ameliorated using the subject vectors and methods include, but are not limited to, osteoporosis, arthrosis, glucose intolerance, insulin resistant, reduced heart, circulatory and/or lung function, cardiovascular disease, loss of memory, loss of neuromuscular coordination and decrease of longevity, or combinations thereof.

The subject vectors and methods find use in a variety of research applications. The subject vectors and methods may be used to analyze the role of telomerase various biological processes including age-related disorders and conditions.

The subject vectors and methods find use in a variety of therapeutic applications. Therapeutic applications of interest include those applications in which the subject is suffering from one or more age-related disorders or conditions. As such, the subject vectors find use in the treatment of a variety of different age-related conditions in various subjects, and may lead to an extended lifespan. For example, the subject vectors and methods may find use in regulated gene therapy.

Extended lifespan may be an increase in the maximum lifespan possible for any particular species of subject. Extended lifespan may be an increase in the average lifespan of an individual of that species who reaches adulthood. Thus, extended lifespan may be a 5%, 10%, 15%, 20% or more increase in maximum lifespan and/or a 5%, 10%, 15%, 20% or more increase in average lifespan.

The application of the invention extends the period of time for which an individual is generally healthy and free of chronic illness and/or the invention ameliorates disorders that appear often in aged and ageing adult population, including reduced epithelial barrier fitness, osteoporosis, glucose intolerance and neuromuscular degeneration associated with loss of neuromuscular coordination. These are well established indicators of ageing progression.

Accordingly, the invention has beneficial effects in at least one of the following group: reducing the incidence of cancer, on delaying and/or ameliorating osteoporosis, improving epithelial barrier fitness, improving glucose tolerance, improving memory function, and improving neuromuscular coordination. The amelioration of age-related disorders provided by the invention can be as a result of reduction of symptoms in an affected subject or a reduction of incidence of the disease or disorder in a population as compared to an untreated population. The application of gene therapy according to the invention has the effect of treating and/or preventing various age-related conditions and diseases, as assessed by particular markers and disorders of ageing. In a further aspect, therefore, the invention refers to a gene therapy method or the used of a nucleic acid vector as described above, for use in the treatment or prevention in a subject of at least a disorder or marker of ageing that is selected from the group of reduced epithelial barrier fitness, osteoporosis, arthrosis, glucose intolerance, insulin resistance, loss of memory, loss of neuromuscular coordination, increase in cardiovascular disease, decrease in heart, circulatory or lung function and decrease in longevity, or combinations thereof. The gene therapy ameliorates at least one marker of ageing, selected for example, from the group of reduced epithelial barrier fitness, osteoporosis, arthrosis, glucose intolerance, insulin resistance, cardiovascular disease, reduced heart and circulatory function, reduced lung function, loss of memory, loss of neuromuscular coordination or decrease of longevity or combinations thereof.

Kits

Aspects of the invention further include kits, where the kits include one or more components employed in methods of the invention, e.g., vectors, as described herein. In some embodiments, the subject kit includes a vector (as described herein), and one or more components selected from a promoter, a virus, a cell, and a buffer. Any of the components described herein may be provided in the kits, e.g., cells, constructs (e.g., vectors) encoding for TERT and/or TR, components suitable for use in expression systems (e.g., cells, cloning vectors, multiple cloning sites (MSC), bi-directional promoters, an internal ribosome entry site (IRES), etc.), etc. A variety of components suitable for use in making and using constructs, cloning vectors and expression systems may find use in the subject kits. Kits may also include tubes, buffers, etc., and instructions for use. The various reagent components of the kits may be present in separate containers, or some or all of them may be pre-combined into a reagent mixture in a single container, as desired.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), Hard Drive etc., on which the information has been recorded. Yet another form of these instructions that may be present is a website address which may be used via the internet to access the information at a removed site.

Aspects of the invention include providing a virus particle that includes a nucleic acid vector, e.g., as described above. Any convenient virus particles may be utilized, and include viral vector particles described above.

Aspects of the invention include providing a cell that includes a nucleic acid vector. The cell that is provided with the vector of interest may vary depending on the specific application being performed. Target cells of interest include eukaryotic cells, e.g., animal cells, where specific types of animal cells include, but are not limited to: insect, worm or mammalian cells. Various mammalian cells may be used, including, by way of example, equine, bovine, ovine, canine, feline, murine, non-human primate and human cells. Among the various species, various types of cells may be used, such as hematopoietic, neural, glial, mesenchymal, cutaneous, mucosal, stromal, muscle (including smooth muscle cells), spleen, reticulo-endothelial, epithelial, endothelial, hepatic, kidney, gastrointestinal, pulmonary, fibroblast, and other cell types. Hematopoietic cells of interest include any of the nucleated cells which may be involved with the erythroid, lymphoid or myelomonocytic lineages, as well as myoblasts and fibroblasts. Also of interest are stem and progenitor cells, such as hematopoietic, neural, stromal, muscle, hepatic, pulmonary, gastrointestinal and mesenchymal stem cells, such as ES cells, epi-ES cells and induced pluripotent stem cells (iPS cells).

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

Construction of Vectors
pSSI4342:
Adeno vector containing hTR and hTERT was constructed.
LITR-U1-hTR-CMV-hTERT-SV40pA-RITR
Region base locations:
Adeno RITR: 2928-3030
U1 promoter: 6459-6668
hTR: 6850-7300
U1-3'box: 7458-7472
CMV promoter: 7485-8073
Kozak: 8082-8098
hTERT: 8087-11482
SV40 pA: 11558-11679
Adeno LITR: 5973-6075
pSSI10902:
Lentiviral vector pSSI10902 was constructed and contains hTERT, Puro gene (for selection of infected cells) and AmCyan gene (a fluorescent protein for color). In pSSI10902, hTERT is expressed using the CMV promoter, Puro gene is expressed using the SV40 promoter, and AmCyan gene is expressed using the CMV promoter. Below is shown the schematic for the pSSI10902 expression cassette. The sequence of this entire vector is also provided (SEQ ID NO: 2).
pSSI10902: 5'-LTR-CMV-hTERT-SV40-Puro-CMV-AmCyan-LTR-3'
Region base locations:
5' LTR: 230-410
CMV promoter: 1883-2374
Kozak: 2627-2643
hTERT: 2632-6027
SV40 promoter: 6053-6286
CMV promoter: 7242-7830
AmCyan: 7891-8577
3' LTR: 9315-9495
pSSI12112:
The lentiviral vector pSSI12112 was constructed as a dual vector containing both hTR and hTERT in the same vector. hTR is expressed using the U1 promoter and hTERT is expressed using the CMV promoter. Note: this plasmid also contains the BSD gene being expressed by the PGK promoter which allows selection for cells infected with the lentivirus created using this plasmid. Below is shown a schematic of the expression cassette for pSSI12112. The sequence of this entire vector is also attached (SEQ ID NO:3).

pSSI12112: 5'-LTR-U1-hTR-PGK-BSD-CMV-hTERT-LTR-3'

Region base locations:
5' LTR: 230-410
U1 promoter: 1876-2085
hTR: 2267-2717
U1-3'box: 2875-2889
PGK promoter: 2916-3421
BSD: 3499-3894
CMV promoter: 4023-4611
Kozak: 4620-4636
hTERT: 4625-8020
3' LTR: 8200-8380

Further vectors were constructed and tested as described herein.

pSSI12112=LTR-U1-hTR-PGK-BSD-CMV-TSS-hTERT-LTR
pSSI12162=LTR-U1-hTR-PGK-BSD-CMV-TSS-nonhTERT-LTR
pSSI12307=LTR-PGK-BSD-CMV-TSS-hTERT-LTR
pSSI12310=LTR-PGK-BSD-CMV-TSS-nonhTERT-LTR The viral vectors are tested in vitro or in vivo using any convenient methods. Methods of interest that are adapted for use in testing the viral vectors described herein include those methods described by WO 2012/001170 and Vidale et al. "The catalytic and the RNA subunits of human telomerase are required to immortalize equid primary fibroblasts." Chromosoma. 2012 Jul. 14. Epub.

Project 2273 pSSI12112 (hTR+hTERT) was tested in MRC5 cells. At 7 days post BSD selection, the TRAP activity from pSSI12112 is slightly stronger than the other 3 test samples (pSSI12162 (hTR+non-functional hTERT), pSSI12307 (hTERT), and pSSI12310 (non-functional hTERT)). At 14 days post selection, the pSSI12112 TRAP activity is less than the other 3 samples and eventually diminishes to no TRAP signal at 21 days post BSD selection.

FIG. 1 depicts the results of a TRAP Assay using the vectors pSSI12112, pSSI12162, pSSI12307 and pSSI12310 where sample cells are collected at 7 days post BSD selection, 17 days post infection.

Figure 2:
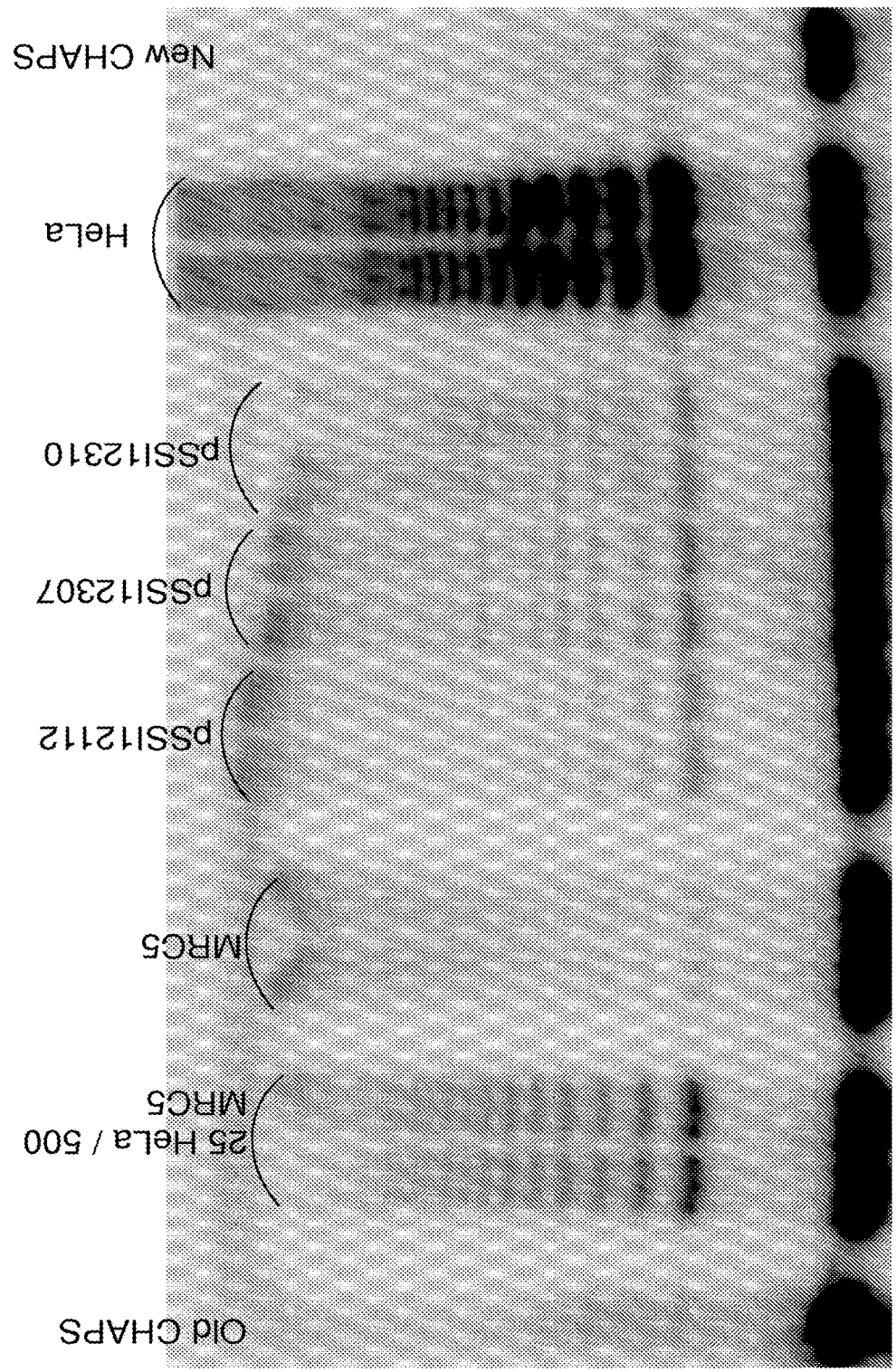
FIG. 2 depicts the results of a TRAP Assay using the vectors pSSI12112, pSSI12307 and pSSI12310 where sample cells are collected at 14 days post BSD selection, 24 days post infection.

FIG. 2 depicts the results of a TRAP Assay using the vectors pSSI12112, pSSI12307 and pSSI12310 where sample cells are collected at 14 days post BSD selection, 24 days post infection.

Figure 3:
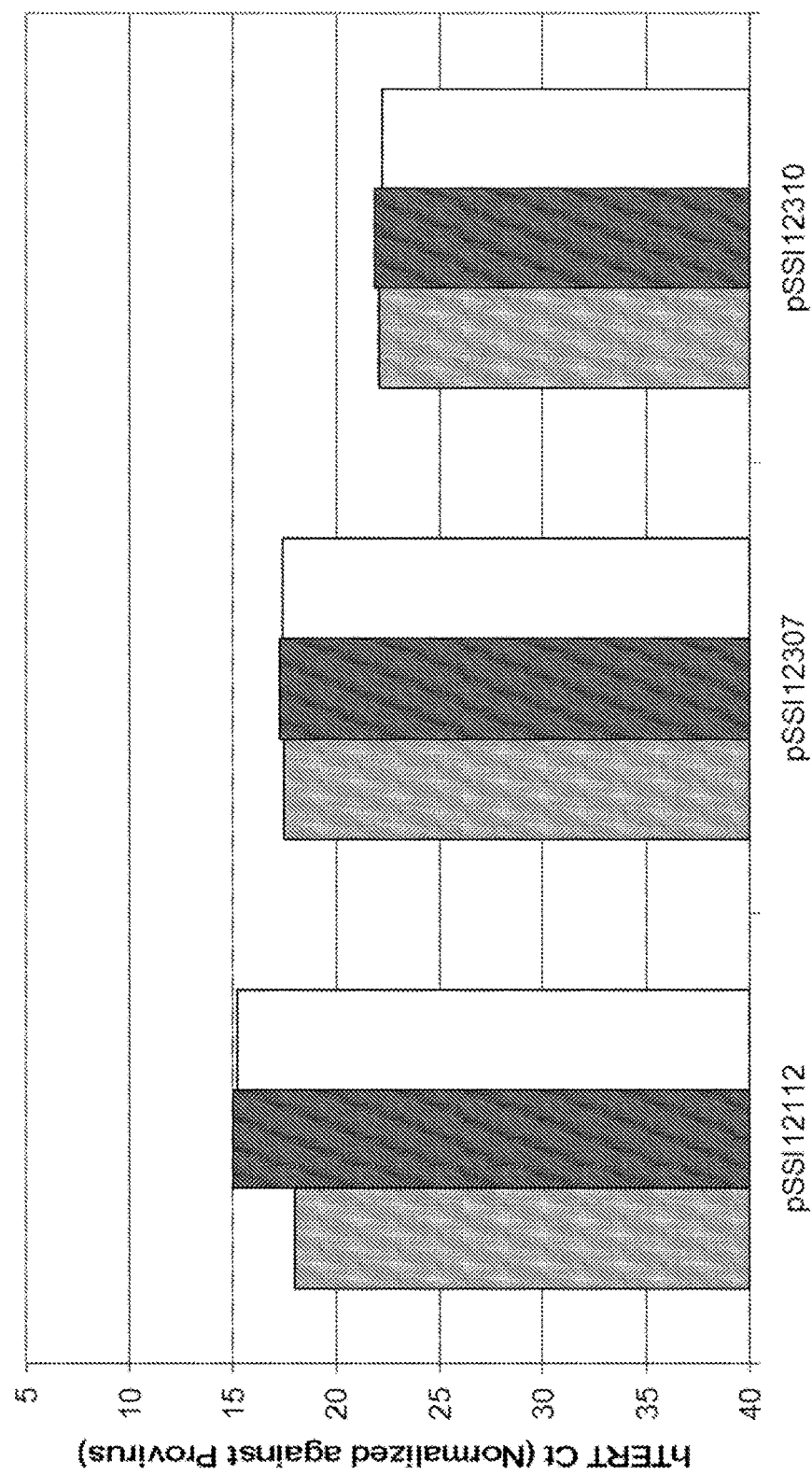
FIG. 3 illustrates RT-PCR results for hTERT Ct (normalized against provirus) using the vectors pSSI12112, pSSI112307 and pSSI12310 where sample cells are collected at 14 days post BSD selection, 24 days post infection.

FIG. 3 illustrates RT-PCR results for hTERT Ct (normalized against provirus) using the vectors pSSI12112, pSSI12307 and pSSI12310 where sample cells are collected at 14 days post BSD selection, 24 days post infection.

Figure 4:
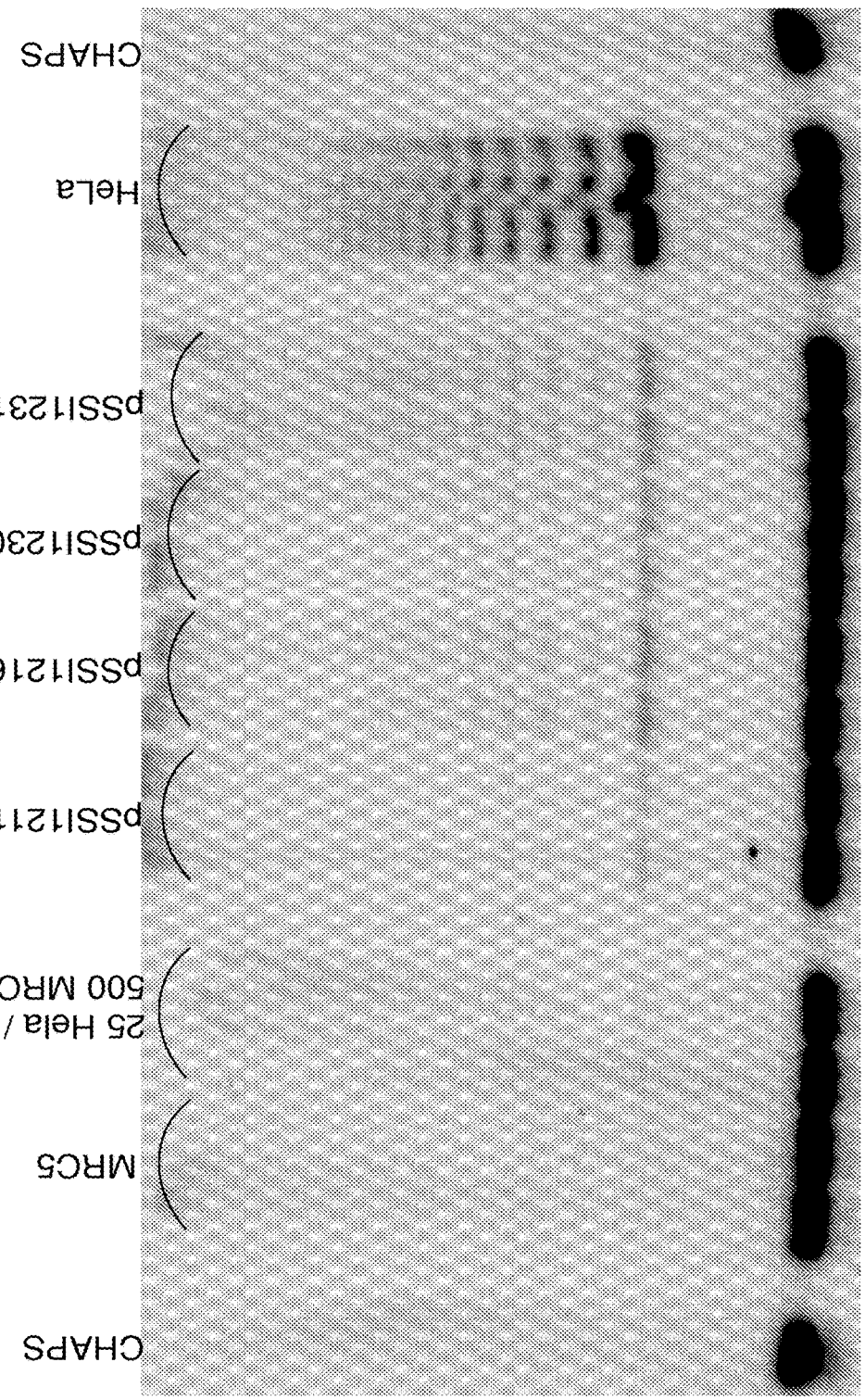
FIG. 4 depicts the results of a TRAP Assay using the vectors pSSI12112, pSSI12162, pSSI12307 and pSSI12310 where sample cells are collected at 21 days post BSD selection, 31 days post infection.

FIG. 4 depicts the results of a TRAP Assay using the vectors pSSI12112, pSSI12162, pSSI112307 and pSSI12310 where sample cells are collected at 21 days post BSD selection, 31 days post infection.

Figure 5:
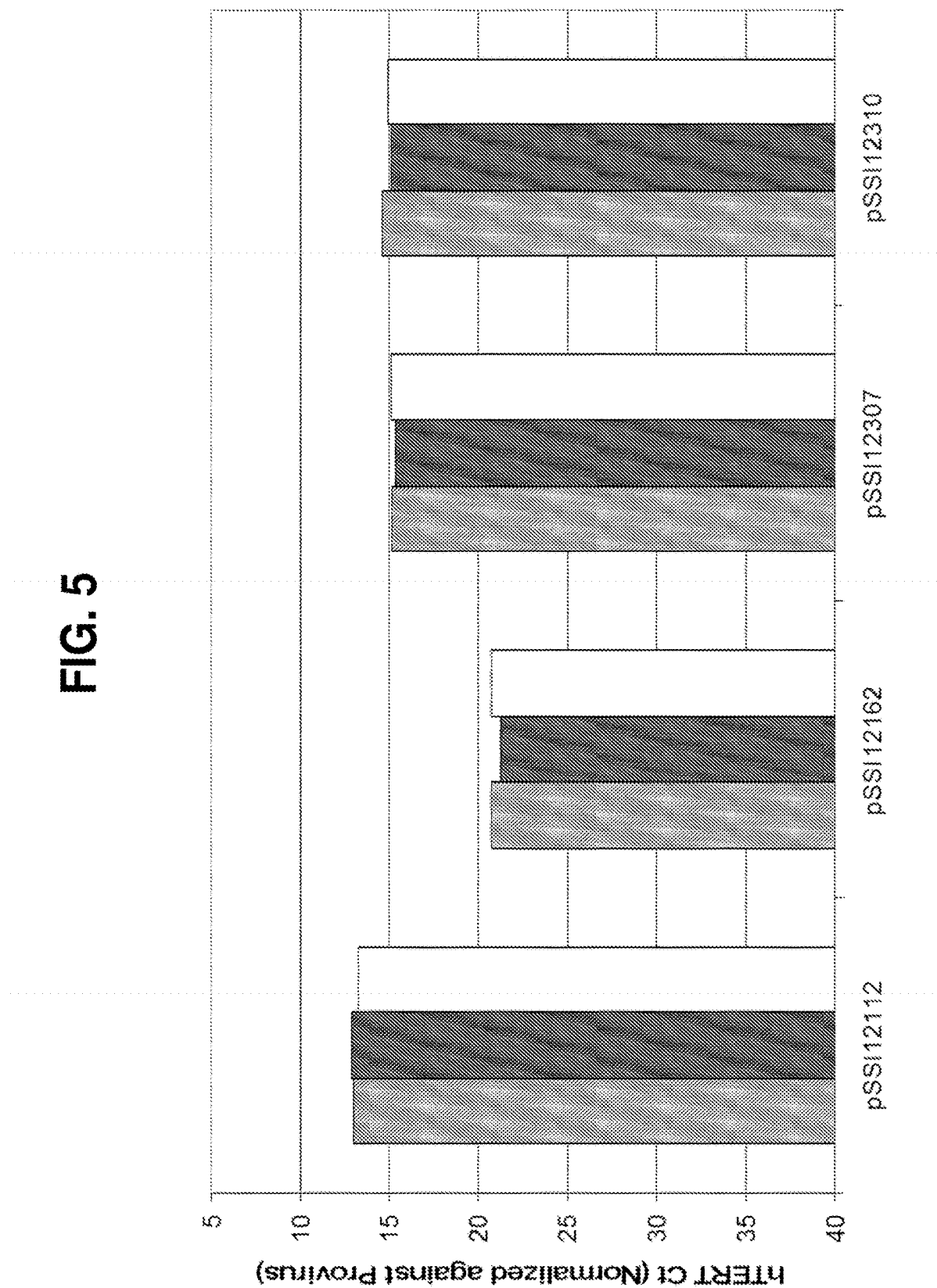
FIG. 5 illustrates RT-PCR results for hTERT Ct (normalized against provirus) using the vectors pSSI12112, pSSI12162, pSSI112307 and pSSI12310 where sample cells are collected at 14 days post BSD selection, 24 days post infection.

FIG. 5 illustrates RT-PCR results for hTERT Ct (normalized against provirus) using the vectors pSSI12112, pSSI12162, pSSI12307 and pSSI12310 where sample cells are collected at 14 days post BSD selection, 24 days post infection.

Figure 6:
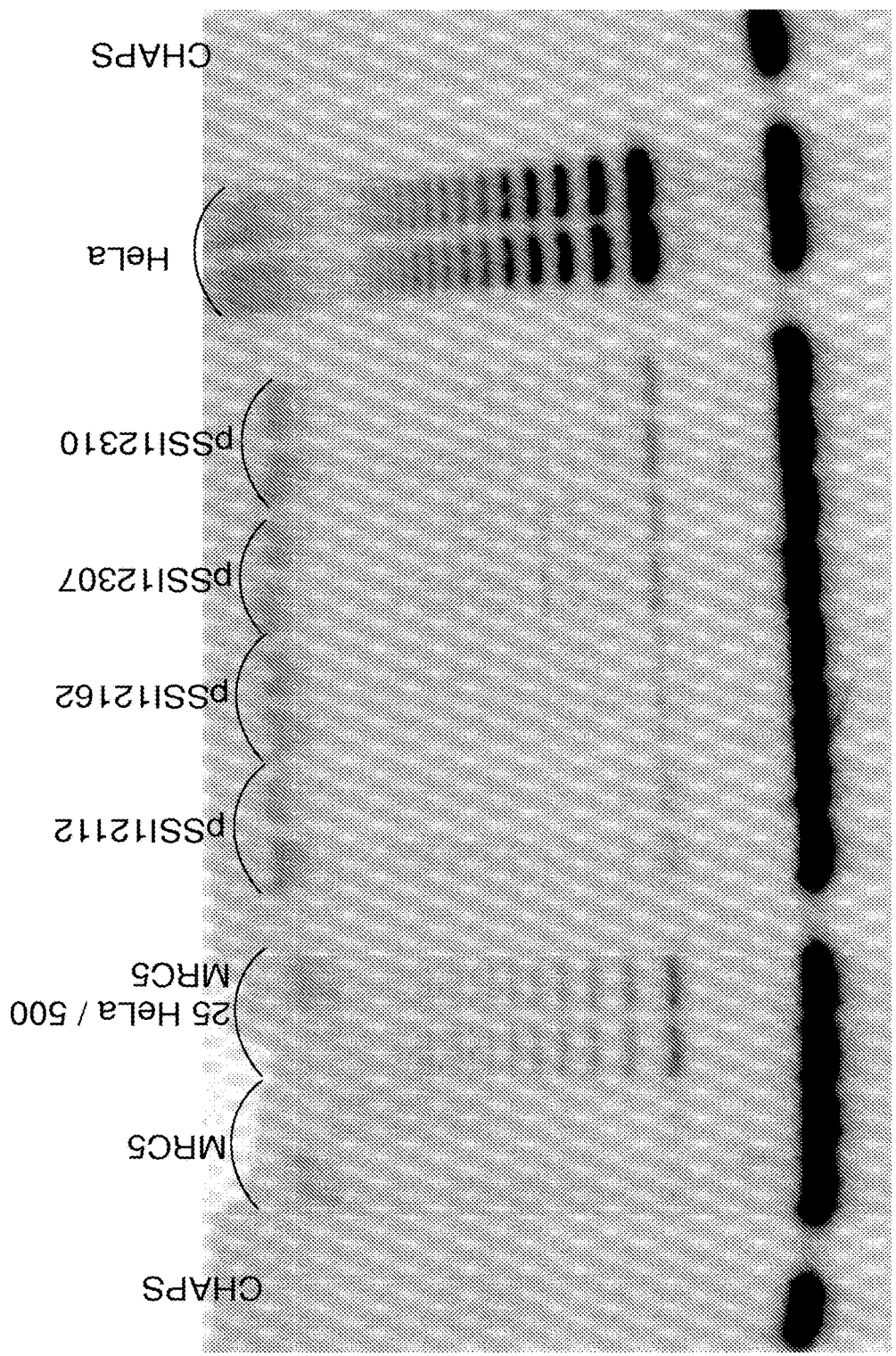
FIG. 6 depicts the results of a TRAP Assay using the vectors pSSI12112, pSSI12162, pSSI12307 and pSSI112310 where sample cells are collected at 49 days post BSD selection, 59 days post infection.

FIG. 6 depicts the results of a TRAP Assay using the vectors pSSI12112, pSSI12162, pSSI12307 and pSSI12310 where sample cells are collected at 49 days post BSD selection, 59 days post infection.

Figure 7:
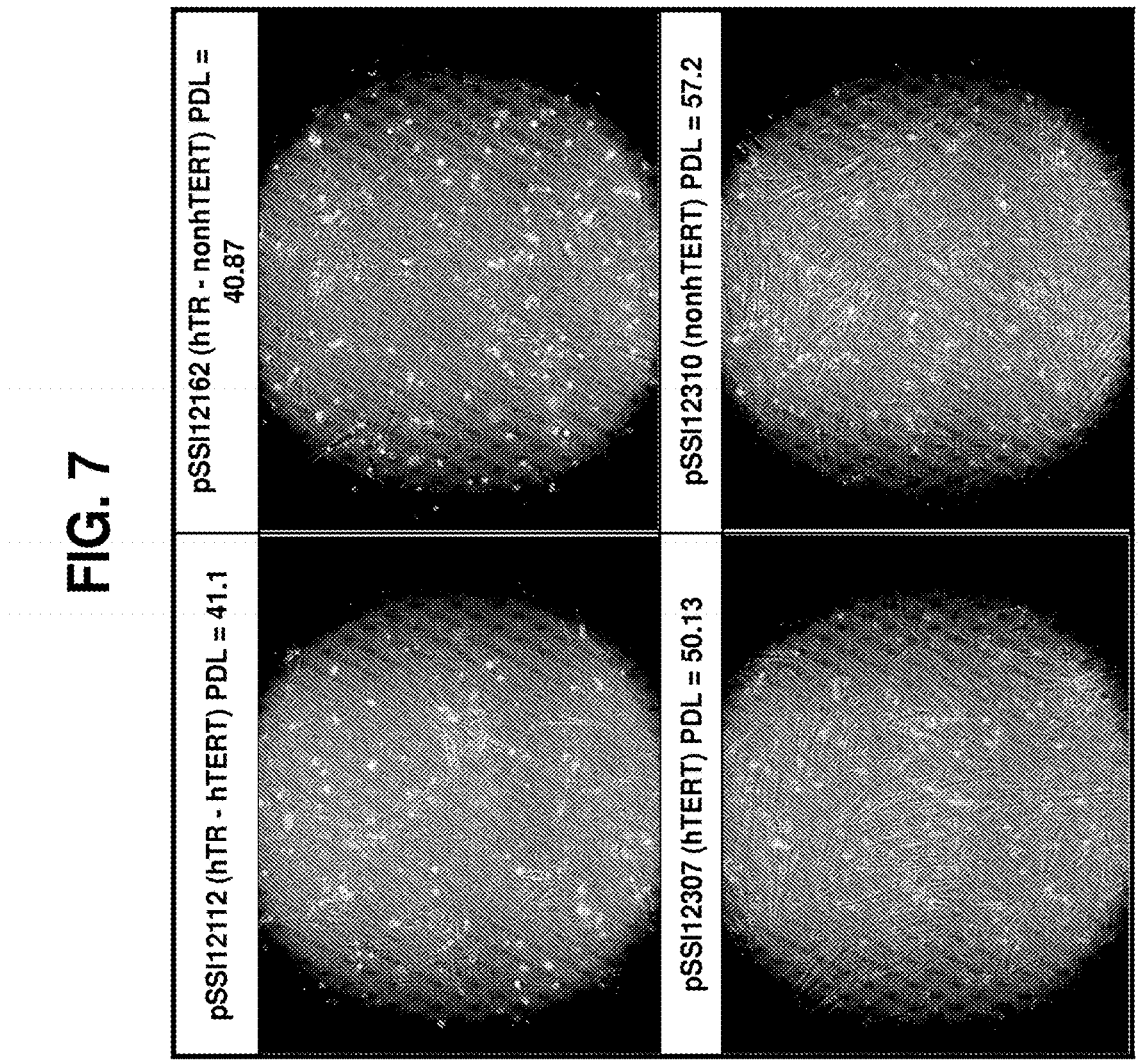
FIG. 7 depicts images comparing cell growth of cells that were maintained in 1.5 ug/ml BSD for 55 days post selection using the vectors pSSI112112, pSSI12162, pSSI12307 and pSSI12310.

FIG. 7 depicts images comparing cell growth of cells that were maintained in 1.5 ug/ml BSD for 55 days post selection using the vectors pSSI12112, pSSI12162, pSSI12307 and pSSI12310.

pSSI14342

(SEQ ID NO: 1)

```
TCACAGAACCCTAGTATTCAACCTGCCACCTCCCTCCCAACACACAGAGTACACAGTCCTTTCTC

CCCGGCTGGCCTTAAAAAGCATCATATCATGGGTAACAGACATATTCTTAGGTGTTATATTCCACA

CGGTTTCCTGTCGAGCCAAACGCTCATCAAGTGATATTAATAAACTCCCCGGGCAGCTCACTTAA

GTTCATGTCGCTGTCCAGCTGCTGAGCCACAGGCTGCTGTCCAACTTGCGGTTGCTTAACGGGC

GGCGAAGGAGAAGTCCACGCCTACATGGGGGGAGAGTCATAATCGTGCATCAGGATAGGGCGG

TGGTGCTGCAGCAGCGCGCGAATAAACTGCTGCCGCCGCCGCTCCGTCCTGCAGGAATACAACA

TGGCAGTGGTCTCCTCAGCGATGATTCGCACCGCCCGCAGCATAAGGCGCTTGTCCTCCGGGCA

CAGCAGCGCACCCTGATCTCACTTAAATCAGCACAGTAACTGCAGCACAGCACCACAATATTGTT

CAAAATCCCACAGTGCAAGGCGCTGTATCCAAAGCTCATGGCGGGGACCACAGAACCCACGTGG

CCATCATACCACAAGCGCAGGTAGATTAAGTGGCGACCCCTCATAAACACGCTGGACATAAACAT

TACCTCTTTTGGCATGTTGTAATTCACCACCTCCCGGTACCATATAAACCTCTGATTAAACATGGC

GCCATCCACCACCATCCTAAACCAGCTGGCCAAAACCTGCCCCGCCGGGNTATACACTGCAGGG

AACCGGGACTTGGACAATGACAAGTGGGAGAGCCCAGGACTCGTAACCATGGATCATCATGCTC

GTCATGATATCAATGTTGGCACAACACAGGCACACGTGCATACACTTCCTCAGGATTACAAGCTC

CTCCCGCGTTAGAACCATATCCCAGGGAACAACCCATTCCTGAATCAGCGTAAATCCCACACTGC

AGGGAAGACCTCGCACGTAACTCACGTTGTGCATTGTCAAAGTGTTACATTCGGGCAGCAGCGG

ATGATCCTCCAGTATGGTAGCGCGGGTTTCTGTCTCAAAAGGAGGTAGACGATCCCTACTGTACG

GAGTGCGCCGAGACAACCGAGATCGTGTTGGTCGTAGTGTCATGCCAAATGGAACGCCGGACGT

AGTCATATTTCCTGAAGCAAAACCAGGTGCGGGCGTGACAAACAGATCTGCGTCTCCGGTCTCG
```

-continued

```
CCGCTTAGATCGCTCTGTGTAGTAGTTGTAGTATATCCACTCTCTCAAAGCATCCAGGCGCCCCC

TGGCTTCGGGTTCTATGTAAACTCCTTCATGCGCCGCTGCCCTGATAACATCCACCACCGCAGAA

TAAGCCACACCCAGCCAACCTACACATTCGTTCTGCGAGTCACACACGGGAGGAGCGGGAAGAG

CTGGAAGAACCATGTTTTTTTTTTATTCCAAAAGATTATCCAAAACCTCAAATGAAGATCTATTA

AGTGAACGCGCTCCCCTCCGGTGGCGTGGTCAAACTCTACAGCCAAAGAACAGATAATGGCATT

TGTAAGATGTTGCACAATGGCTTCCAAAAGGCAAACGGCCCTCACGTCCAAGTGGACGTAAAGG

CTAAACCCTTCAGGGTGAATCTCCTCTATAAACATTCCAGCACCTTCAACCATGCCCAAATAATTC

TCATCTCGCCACCTTCTCAATATATCTCTAAGCAAATCCCGAATATTTAAGTCCGGGCCATTGTAA

AAAATTTGGCTCCAGAGCGCCCTCCACCTTCAGCCTCAAGCAGCGAATCATGATTGCAAAAATTC

AGGTTCCTCACAGACCTGTATAAGATTCAAAAGCGGAACATTAACAAAAATACCGCGATCCCGTA

GGTCCCTTCGCAGGGCCAGCTGAACATAATCGTGCAGGTCTGCACGGACCAGCGCGGCCACTT

CCCCGCCAGGAACCATGACAAAAGAACCCACACTGATTATGACACGCATACTCGGAGCTATGCTA

ACCAGCGTAGCCCCGATGTAAGCTTGTTGCATGGGCGGCGATATAAAATGCAAGGTGCTGCTCA

AAAAATCAGGCAAAGCCTCGCGCAAAAAAGAAAGCACATCGTAGTCATGCTCATGCAGATAAAGG

CAGGTAAGCTCCGGAACCACCACAGAAAAAGACACCATTTTTCTCTCAAACATGTCTGCGGGTTT

CTGCATAAACACAAAATAAAATAACAAAAAAACATTTAAACATTAGAAGCCTGTCTTACAACAGGAA

AAACAACCCTTATAAGCATAAGACGGACTACGGCCATGCCGGCGTGACCGTAAAAAAACTGGTCA

CCGTGATTAAAAAGCACCACCGACAGCTCCTCGGTCAGTCCGGAGTCATAATGTAAGACTCGGTA

AACACATCAGGTTGATTCACATCGGTCAGTGTTAAAAAGCGACCGAAATAGCCNGGGGGAATACA

ATACCCGCAGGCGTAGAGACAACATTACAGCCCCCATAGGAGGTATAACAAAATTAATAGGAGAG

AAAAACACATAAACACCTGAAAAACCCTCCTGCCTAGGCAAAATAGCACCCTCCCGCTCCAGAAC

AACATACAGCGCTTCCACAGCGGCAGCCATAACAGTCAGCCTTACCAGTAAAAAAGAAAACCTAT

TAAAAAAACACCACTCGACACGGCACCAGCTCAATCAGTCACAGTGTAAAAAAGGGCCAAGTGCA

GAGCGAGTATATATAGGACTAAAAAATGACGGTAACGGTTAAAGTCCACAAAAAAACACCCAGAAA

ACCGCACGCGAACCTACGCCCAGAAACGAAAGCCAAAAAACCCACAACTTCCTCAAATCGTCACT

TCCGTTTTCCCACGTTACGTCACTTCCCATTTTAAGAAAACTACAATTCCCAACACATACAAGTTAC

TCCGCCCTAAAACCTACGTCACCCGCCCCGTTCCCACGCCCCGCGCCACGTCACAAACTCCACC

CCCTCATTATCATATTGGCTTCAATCCAAAATAAGGTATATTATTGATGATGTTAATTAACATGCAT

GGATCCATATGCGGTGTGAAATACCGCACAGATGCGTAAGGAGAAAATACCGCATCAGGCGCTC

TTCCGCTTCCTCGCTCACTGACTCGCTGCGCTCGGTCGTTCGGCTGCGGCGAGCGGTATCAGCT

CACTCAAAGGCGGTAATACGGTTATCCACAGAATCAGGGGATAACGCAGGAAAGAACATGTGAG

CAAAAGGCCAGCAAAAGGCCAGGAACCGTAAAAAGGCCGCGTTGCTGGCGTTTTTCCATAGGCT

CCGCCCCCTGACGAGCATCACAAAAATCGACGCTCAAGTCAGAGGTGGCGAAACCCGACAGGA

CTATAAAGATACCAGGCGTTTCCCCCTGGAAGCTCCCTCGTGCGCTCTCCTGTTCCGACCCTGCC

GCTTACCGGATACCTGTCCGCCTTTCTCCCTTCGGGAAGCGTGGCGCTTTCTCATAGCTCACGCT

GTAGGTATCTCAGTTCGGTGTAGGTCGTTCGCTCCAAGCTGGGCTGTGTGCACGAACCCCCCGT

TCAGCCCGACCGCTGCGCCTTATCCGGTAACTATCGTCTTGAGTCCAACCCGGTAAGACACGAC

TTATCGCCACTGGCAGCAGCCACTGGTAACAGGATTAGCAGAGCGAGGTATGTAGGCGGTGCTA

CAGAGTTCTTGAAGTGGTGGCCTAACTACGGCTACACTAGAAGGACAGTATTTGGTATCTGCGCT

CTGCTGAAGCCAGTTACCTTCGGAAAAAGAGTTGGTAGCTCTTGATCCGGCAAACAAACCACCGC
```

-continued

```
TGGTAGCGGTGGTTTTTTTGTTTGCAAGCAGCAGATTACGCGCAGAAAAAAAGGATCTCAAGAAG

ATCCTTTGATCTTTTCTACGGGGTCTGACGCTCAGTGGAACGAAAACTCACGTTAAGGGATTTTG

GTCATGAGATTATCAAAAAGGATCTTCACCTAGATCCTTTTAAATTAAAAATGAAGTTTTAAATCAA

TCTAAAGTATATATGAGTAAACTTGGTCTGACAGTTACCAATGCTTAATCAGTGAGGCACCTATCT

CAGCGATCTGTCTATTTCGTTCATCCATAGTTGCCTGACTCCCCGTCGTGTAGATAACTACGATAC

GGGAGGGCTTACCATCTGGCCCCAGTGCTGCAATGATACCGCGAGACCCACGCTCACCGGCTC

CAGATTTATCAGCAATAAACCAGCCAGCCGGAAGGGCCGAGCGCAGAAGTGGTCCTGCAACTTT

ATCCGCCTCCATCCAGTCTATTAATTGTTGCCGGGAAGCTAGAGTAAGTAGTTCGCCAGTTAATA

GTTTGCGCAACGTTGTTGCCATTGCTGCAGCCATGAGATTATCAAAAGGATCTTCACCTAGATC

CTTTTCACGTAGAAAGCCAGTCCGCAGAAACGGTGCTGACCCCGGATGAATGTCAGCTACTGGG

CTATCTGGACAAGGGAAAACGCAAGCGCAAAGAGAAAGCAGGTAGCTTGCAGTGGGCTTACATG

GCGATAGCTAGACTGGGCGGTTTTATGGACAGCAAGCGAACCGGAATTGCCAGCTGGGGCGCC

CTCTGGTAAGGTTGGGAAGCCCTGCAAAGTAAACTGGATGGCTTTCTTGCCGCCAAGGATCTGAT

GGCGCAGGGGATCAAGCTCTGATCAAGAGACAGGATGAGGATCGTTTCGCATGATTGAACAAGA

TGGATTGCACGCAGGTTCTCCGGCCGCTTGGGTGGAGAGGCTATTCGGCTATGACTGGGCACAA

CAGACAATCGGCTGCTCTGATGCCGCCGTGTTCCGGCTGTCAGCGCAGGGGCGCCCGGTTCTTT

TTGTCAAGACCGACCTGTCCGGTGCCCTGAATGAACTGCAAGACGAGGCAGCGCGGCTATCGTG

GCTGGCCACGACGGGCGTTCCTTGCGCAGCTGTGCTCGACGTTGTCACTGAAGCGGGAAGGGA

CTGGCTGCTATTGGGCGAAGTGCCGGGGCAGGATCTCCTGTCATCTCACCTTGCTCCTGCCGAG

AAAGTATCCATCATGGCTGATGCAATGCGGCGGCTGCATACGCTTGATCCGGCTACCTGCCCATT

CGACCACCAAGCGAAACATCGCATCGAGCGAGCACGTACTCGGATGGAAGCCGGTCTTGTCGAT

CAGGATGATCTGGACGAAGAGCATCAGGGGCTCGCGCCAGCCGAACTGTTCGCCAGGCTCAAG

GCGAGCATGCCCGACGGCGAGGATCTCGTCGTGACCCATGGCGATGCCTGCTTGCCGAATATCA

TGGTGGAAAATGGCCGCTTTTCTGGATTCATCGACTGTGGCCGGCTGGGTGTGGCGGACCGCTA

TCAGGACATAGCGTTGGCTACCCGTGATATTGCTGAAGAGCTTGGCGGCGAATGGGCTGACCGC

TTCCTCGTGCTTTACGGTATCGCCGCTCCCGATTCGCAGCGCATCGCCTTCTATCGCCTTCTTGA

CGAGTTCTTCTGAATTTTGTTAAAATTTTTGTTAAATCAGCTCATTTTTTAACCAATAGGCCGAAAT

CGGCAACATCCCTTATAAATCAAAAGAATAGACCGCGATAGGGTTGAGTGTTGTTCCAGTTTGGA

ACAAGAGTCCACTATTAAAGAACGTGGACTCCAACGTCAAAGGGCGAAAAACCGTCTATCAGGGC

GATGGCCCACTACGTGAACCATCACCCAAATCAAGTTTTTTGCGGTCGAGGTGCCGTAAAGCTCT

AAATCGGAACCCTAAAGGGAGCCCCCGATTTAGAGCTTGACGGGGAAAGCCGGCGAACGTGGC

GAGAAAGGAAGGGAAGAAAGCGAAAGGAGCGGGCGCTAGGGCGCTGGCAAGTGTAGCGGTCA

CGCTGCGCGTAACCACCACACCCGCGCGCTTAATGCGCCGCTACAGGGCGCGTCCATTCGCCA

TTCAGGATCGAATTAATTCTTAATTAACATCATCAATAATATACCTTATTTTGGATTGAAGCCAATAT

GATAATGAGGGGGTGGAGTTTGTGACGTGGCGCGGGGCGTGGGAACGGGGCGGGTGACGTAG

TAGTGTGGCGGAAGTGTGATGTTGCAAGTGTGGCGGAACACATGTAAGCGACGGATGTGGCAAA

AGTGACGTTTTTGGTGTGCGCCGGTGTACACAGGAAGTGACAATTTTCGCGCGGTTTTAGGCGG

ATGTTGTAGTAAATTTGGGCGTAACCGAGTAAGATTTGGCCATTTTCGCGGGAAAACTGAATAAG

AGGAAGTGAAATCTGAATAATTTTGTGTTACTCATAGCGCGTAATACTGGTACCGCGGCCGCCTC

GAGTCTAGAGATATCGAATTCAAGCTTAAGGTGCACGGCCCACGTGGCCACTAGTAATTTTTCTG

CAGAAAACGTACCCGGGGATCCTCTAGGATCCCACCGAAAGGTTGCTCCTTAACACAGGCTAAG
```

-continued

```
GACCAGCTTCTTTGGGAGAGAACAGACGCAGGGGCGGGAGGGAAAAAGGGAGAGGCAGACGTC
ACTTCCCCTTGGCGGCTCTGGCAGCAGATTGGTCGGTTGAGTGGCAGAAAGGCAGACGGGGAC
TGGGCAAGGCACTGTCGGTGACATCACGGACAGGGCGACTTCTATGTAGATGAGGCAGCGCAG
AGGCTGCTGCTTCGCCACTTGCTGCTTCGCCACGAAGGAGTTCCCGTGCCCTGGGAGCGGGTTC
AGGACCGCGGATCGGAAGTGAGAATCCCAGCTGTGTGTCAGGGCTGGAAAGGGCTCGGGAGTG
CGCGGGGCAAGTGACCGTGTGTGTAAAGAGTGAGGCGTATGAGGCTGTGTCGGGGCAGAGCCC
GAAGATCCGGGTTGCGGAGGGTGGGCCTGGGAGGGGTGGTGGCCATTTTTTGTCTAACCCTAAC
TGAGAAGGGCGTAGGCGCCGTGCTTTTGCTCCCCGCGCGTGTTTTTCTCGCTGACTTTCAGCG
GGCGGAAAAGCCTCGGCCTGCCGCCTTCCACCGTTCATTCTAGAGCAAACAAAAAATGTCAGCT
GCTGGCCCGTTCGCCCCTCCCGGGGACCTGCGGCGGGTCGCCTGCCCAGCCCCCGAACCCCG
CCTGGAGGCCGCGGTCGGCCCGGGGCTTCTCCGGAGGCACCCACTGCCACCGCGAAGAGTTG
GGCTCTGTCAGCCGCGGGTCTCTCGGGGGCGAGGGCGAGGTTCAGGCCTTTCAGGCCGCAGG
AAGAGGAACGGAGCGAGTCCCCGCGCGCGGCGCGATTCCCTGAGCTGTGGGACGTGCACCCA
GGACTCGGCTCACACATGCAGTTCGCTTTCCTGTTGGTGGGGGAACGCCGATCGTGCGCATCC
GTCACCCCTCGCCGGCAATGGGGGCTTGTGAACCCCCAAACCTGACTGACTGGGCCAGTGTGCT
GCAAATTGGCAGGAGACGTGAAGGCACCTCCAAAGTCGACTTTCTGGAGTTTCAAAAACAGACC
GTACGATGCATTAGTTATTAATAGTAATCAATTACGGGGTCATTAGTTCATAGCCCATATATGGAG
TTCCGCGTTACATAACTTACGGTAAATGGCCCGCCTGGCTGACCGCCCAACGACCCCCGCCCAT
TGACGTCAATAATGACGTATGTTCCCATAGTAACGCCAATAGGGACTTTCCATTGACGTCAATGG
GTGGAGTATTTACGGTAAACTGCCCACTTGGCAGTACATCAAGTGTATCATATGCCAAGTACGCC
CCCTATTGACGTCAATGACGGTAAATGGCCCGCCTGGCATTATGCCCAGTACATGACCTTATGGG
ACTTTCCTACTTGGCAGTACATCTACGTATTAGTCATCGCTATTACCATGGTGATGCGGTTTTGGC
AGTACATCAATGGGCGTGGATAGCGGTTTGACTCACGGGGATTTCCAAGTCTCCACCCCATTGAC
GTCAATGGGAGTTTGTTTTGGCACCAAAATCAACGGGACTTTCCAAAATGTCGTAACAACTCCGC
CCCATTGACGCAAATGGGCGGTAGGCGTGTACGGTGGGAGGTCTATATAAGCAGAGCTGGTTTA
GTGAACCGTCAGATCCGCTAGCCCCACCATGCCGCGCGCTCCCCGCTGCCGAGCCGTGCGCTC
CCTGCTGCGCAGCCACTACCGCGAGGTGCTGCCGCTGGCCACGTTCGTGCGGCGCCTGGGGC
CCCAGGGCTGGCGGCTGGTGCAGCGCGGGACCCGGCGGCTTTCCGCGCGCTGGTGGCCCAG
TGCCTGGTGTGCGTGCCCTGGGACGCACGGCCGCCCCCCGCCGCCCCCTCCTTCCGCCAGGTG
TCCTGCCTGAAGGAGCTGGTGGCCCGAGTGCTGCAGAGGCTGTGCGAGCGCGGCGCGAAGAAC
GTGCTGGCCTTCGGCTTCGCGCTGCTGGACGGGGCCCGCGGGGGCGCCCCCGAGGCCTTCAC
CACCAGCGTGCGCAGCTACCTGCCCAACACGGTGACCGACGCACTGCGGGGAGCGGGGCGT
GGGGGCTGCTGTTGCGCCGCGTGGGCGACGACGTGCTGGTTCACCTGCTGGCACGCTGCGCG
CTCTTTGTGCTGGTGGCTCCCAGCTGCGCCTACCAGGTGTGCGGGCCGCCGCTGTACCAGCTC
GGCGCTGCCACTCAGGCCCGGCCCCCGCCACACGCTAGTGGACCCCGAAGGCGTCTGGGATG
CGAACGGGCCTGGAACCATAGCGTCAGGGAGGCCGGGGTCCCCCTGGGCCTGCCAGCCCCGG
GTGCGAGGAGGCGCGGGGGCAGTGCCAGCCGAAGTCTGCCGTTGCCCAAGAGGCCCAGGCGT
GGCGCTGCGCCTGAGCCGGAGCGGACGCCCGTTGGGCAGGGGTCCTGGGCCCACCCGGGCAG
GACGCGTGGACCGAGTGACCGTGGTTTCTGTGTGGTGTCACCTGCCAGACCCGCCGAAGAAGC
CACCTCTTTGGAGGGTGCGCTCTCTGGCACGCGCCACTCCCACCCATCCGTGGGCCGCCAGCA
```

-continued

```
CCACGCGGGCCCCCCATCCACATCGCGGCCACCACGTCCCTGGGACACGCCTTGTCCCCGGT

GTACGCCGAGACCAAGCACTTCCTCTACTCCTCAGGCGACAAGGAGCAGCTGCGGCCCTCCTTC

CTACTCAGCTCTCTGAGGCCCAGCCTGACTGGCGCTCGGAGGCTCGTGGAGACCATCTTTCTGG

GTTCCAGGCCCTGGATGCCAGGGACTCCCCGCAGGTTGCCCCGCCTGCCCCAGCGCTACTGGC

AAATGCGGCCCCTGTTTCTGGAGCTGCTTGGGAACCACGCGCAGTGCCCCTACGGGGTGCTCCT

CAAGACGCACTGCCCGCTGCGAGCTGCGGTCACCCCAGCAGCCGGTGTCTGTGCCCGGGAGAA

GCCCCAGGGCTCTGTGGCGGCCCCCGAGGAGGAGGACACAGACCCCCGTCGCCTGGTGCAGC

TGCTCCGCCAGCACAGCAGCCCCTGGCAGGTGTACGGCTTCGTGCGGGCCTGCCTGCGCCGGC

TGGTGCCCCCAGGCCTCTGGGGCTCCAGGCACAACGAACGCCGCTTCCTCAGGAACACCAAGA

AGTTCATCTCCCTGGGGAAGCATGCCAAGCTCTCGCTGCAGGAGCTGACGTGGAAGATGAGCGT

GCGGGCTGCGCTTGGCTGCGCAGGAGCCCAGGGGTTGGCTGTGTTCCGGCCGCAGAGCACC

GTCTGCGTGAGGAGATCCTGGCCAAGTTCCTGCACTGGCTGATGAGTGTGTACGTCGTCGAGCT

GCTCAGGTCTTTCTTTTATGTCACGGAGACCACGTTTCAAAAGAACAGGCTCTTTTTCTACCGGAA

GAGTGTCTGGAGCAAGTTGCAAAGCATTGGAATCAGACAGCACTTGAAGAGGGTGCAGCTGCGG

GAGCTGTCGGAAGCAGAGGTCAGGCAGCATCGGGAAGCCAGGCCCGCCCTGCTGACGTCCAGA

CTCCGCTTCATCCCCAAGCCTGACGGGCTGCGGCCGATTGTGAACATGGACTACGTCGTGGGAG

CCAGAACGTTCCGCAGAGAAAAGAGGGCCGAGCGTCTCACCTCCAGGGTGAAGGCACTGTTCA

GCGTGCTCAACTACGAGCGGGCGCGGCGCCCCGGCCTCCTGGGCGCCTCTGTGCTGGGCCTG

GACGATATCCACAGGGCCTGGCGCACCTTCGTGCTGCGTGTGCGGGCCCAGGACCCGCCGCCT

GAGCTGTACTTTGTCAAGGTGGATGTGACGGGCGCGTACGACACCATCCCCCAGGACAGGCTCA

CGGAGGTCATCGCCAGCATCATCAAACCCCAGAACACGTACTGCGTGCGTCGGTATGCCGTGGT

CCAGAAGGCCGCCCATGGGCACGTCCGCAAGGCCTTCAAGAGCCACGTCTCTACCTTGACAGAC

CTCCAGCCGTACATGCGACAGTTCGTGGCTCACCTGCAGGAGACCAGCCCGCTGAGGGATGCC

GTCGTCATCGAGCAGAGCTCCTCCCTGAATGAGGCCAGCAGTGGCCTCTTCGACGTCTTCCTAC

GCTTCATGTGCCACCACGCCGTGCGCATCAGGGGCAAGTCCTACGTCCAGTGCCAGGGGATCC

CGCAGGGCTCCATCCTCTCCACGCTGCTCTGCAGCCTGTGCTACGGCGACATGGAGAACAAGCT

GTTTGCGGGGATTCGGCGGGACGGGCTGCTCCTGCGTTTGGTGGATGATTTCTTGTTGGTGAGA

CCTCACCTCACCCACGCGAAAACCTTCCTCAGGACCCTGGTCCGAGGTGTCCCTGAGTATGGCT

GCGTGGTGAACTTGCGGAAGACAGTGGTGAACTTCCCTGTAGAAGACGAGGCCCTGGGTGGCA

CGGCTTTTGTTCAGATGCCGGCCCACGGCCTATTCCCCTGGTGCGGCCTGCTGCTGGATACCCG

GACCCTGGAGGTGCAGAGCGACTACTCCAGCTATGCCCGGACCTCCATCAGAGCCAGTCTCACC

TTCAACCGCGGCTTCAAGGCTGGGAGGAACATGCGTCGCAAACTCTTTGGGGTCTTGCGGCTGA

AGTGTCACAGCCTGTTTCTGGATTTGCAGGTGAACAGCCTCCAGACGGTGTGCACCAACATCTAC

AAGATCCTCCTGCTGCAGGCGTACAGGTTTCACGCATGTGTGCTGCAGCTCCCATTTCATCAGCA

AGTTTGGAAGAACCCCACATTTTTCCTGCGCGTCATCTCTGACACGGCCTCCCTCTGCTACTCCA

TCCTGAAAGCCAAGAACGCAGGGATGTCGCTGGGGGCCAAGGGCGCCGCCGGCCCTCTGCCCT

CCGAGGCCGTGCAGTGGCTGTGCCACCAAGCATTCCTGCTCAAGCTGACTCGACACCGTGTCAC

CTACGTGCCACTCCTGGGGTCACTCAGGACAGCCCAGACGCAGCTGAGTCGGAAGCTCCCGGG

GACGACGCTGACTGCCCTGGAGGCCGCAGCCAACCCGGCACTGCCCTCAGACTTCAAGACCAT

CCTGGACTGAGTCGAAACTCGCGGCCGCCATATGCATCCTAGGCCTATTAATATTCCGGAGTATA

CGTAGCCGGCTAACGTTAACTTGTTTATTGCAGCTTATAATGGTTACAAATAAAGCAATAGCATCA
```

-continued

```
CAAATTTCACAAATAAAGCATTTTTTTCACTGCATTCTAGTTGTGGTTTGTCCAAACTCATCAATGT
ATCTTAACGCGGATCTGGGCGTGGTTAAGGGTGGGAAAGAATATATAAGGTGGGGGTCTTATGTA
GTTTTGTATCTGTTTTGCAGCAGCCGCCGCCGCCATGAGCACCAACTCGTTTGATGGAAGCATTG
TGAGCTCATATTTGACAACGCGCATGCCCCCATGGGCCGGGGTGCGTCAGAATGTGATGGGCTC
CAGCATTGATGGTCGCCCCGTCCTGCCCGCAAACTCTACTACCTTGACCTACGAGACCGTGTCT
GGAACGCCGTTGGAGACTGCAGCCTCCGCCGCCGCTTCAGCCGCTGCAGCCACCGCCCGCGG
GATTGTGACTGACTTTGCTTTCCTGAGCCCGCTTGCAAGCAGTGCAGCTTCCCGTTCATCCGCCC
GCGATGACAAGTTGACGGCTCTTTTGGCACAATTGGATTCTTTGACCCGGGAACTTAATGTCGTT
TCTCAGCAGCTGTTGGATCTGCGCCAGCAGGTTTCTGCCCTGAAGGCTTCCTCCCCTCCCAATG
CGGTTTAAAACATAAATAAAAAACCAGACTCTGTTTGGATTTGGATCAAGCAAGTGTCTTGCTGTC
TTTATTTAGGGGTTTTGCGCGCGCGGTAGGCCCGGGACCAGCGGTCTCGGTCGTTGAGGGTCCT
GTGTATTTTTTCCAGGACGTGGTAAAGGTGACTCTGGATGTTCAGATACATGGGCATAAGCCCGT
CTCTGGGGTGGAGGTAGCACCACTGCAGAGCTTCATGCTGCGGGGTGGTGTTGTAGATGATCCA
GTCGTAGCAGGAGCGCTGGGCGTGGTGCCTAAAAATGTCTTTCAGTAGCAAGCTGATTGCCAGG
GGCAGGCCCTTGGTGTAAGTGTTTACAAAGCGGTTAAGCTGGGATGGGTGCATACGTGGGGATA
TGAGATGCATCTTGGACTGTATTTTTAGGTTGGCTATGTTCCCAGCCATATCCCTCCGGGGATTCA
TGTTGTGCAGAACCACCAGCACAGTGTATCCGGTGCACTTGGGAAATTTGTCATGTAGCTTAGAA
GGAAATGCGTGGAAGAACTTGGAGACGCCCTTGTGACCTCCAAGATTTTCCATGCATTCGTCCAT
AATGATGGCAATGGGCCCACGGGCGGCGGCCTGGGCGAAGATATTCTGGGATCACTAACGTCA
TAGTTGTGTTCCAGGATGAGATCGTCATAGGCCATTTTTACAAAGCGCGGGCGGAGGGTGCCAG
ACTGCGGTATAATGGTTCCATCCGGCCCAGGGGCGTAGTTACCCTCACAGATTTGCATTTCCCAC
GCTTTGAGTTCAGATGGGGGGATCATGTCTACCTGCGGGGCGATGAAGAAAACGGTTTCCGGGG
TAGGGGAGATCAGCTGGGAAGAAAGCAGGTTCCTGAGCAGCTGCGACTTACCGCAGCCGGTGG
GCCCGTAAATCACACCTATTACCGGGTGCAACTGGTAGTTAAGAGAGCTGCAGCTGCCGTCATC
CCTGAGCAGGGGGGCCACTTCGTTAAGCATGTCCCTGACTCGCATGTTTTCCCTGACCAAATCC
GCCAGAAGGCGCTCGCCGCCCAGCGATAGCAGTTCTTGCAAGGAAGCAAAGTTTTTCAACGGTT
TGAGACCGTCCGCCGTAGGCATGCTTTTGAGCGTTTGACCAAGCAGTTCCAGGCGGTCCCACAG
CTCGGTCACCTGCTCTACGGCATCTCGATCCAGCATATCTCCTCGTTTCGCGGGTTGGGCGGC
TTTCGCTGTACGGCAGTAGTCGGTGCTCGTCCAGACGGGCCAGGGTCATGTCTTTCCACGGGCG
CAGGGTCCTCGTCAGCGTAGTCTGGGTCACGGTGAAGGGGTGCGCTCCGGGCTGCGCGCTGGC
CAGGGTGCGCTTGAGGCTGGTCCTGCTGGTGCTGAAGCGCTGCCGGTCTTCGCCCTGCGCGTC
GGCCAGGTAGCATTTGACCATGGTGTCATAGTCCAGCCCCTCCGCGGCGTGGCCCTTGGCGCG
CAGCTTGCCCTTGGAGGAGGCGCCGCACGAGGGGCAGTGCAGACTTTTGAGGGCGTAGAGCTT
GGGCGCGAGAAATACCGATTCCGGGGAGTAGGCATCCGCGCCGCAGGCCCCGCAGACGGTCTC
GCATTCCACGAGCCAGGTGAGCTCTGGCCGTTCGGGGTCAAAAACCAGGTTTCCCCCATGCTTT
TTGATGCGTTTCTTACCTCTGGTTTCCATGAGCCGGTGTCCACGCTCGGTGACGAAAAGGCTGTC
CGTGTCGCCGTATACAGACTTGAGAGGCCTGTCCTCGAGCGGTGTTCCGCGGTCCTCCTCGTAT
AGAAACTCGGACCACTCTGAGACAAAGGCTCGCGTCCAGGCCAGCACGAAGGAGGCTAAGTGG
GAGGGGTAGCGGTCGTTGTCCACTAGGGGGTCCACTCGCTCCAGGGTGTGAAGACACATGTCG
CCCTCTTCGGCATCAAGGAAGGTGATTGGTTTGTAGGTGTAGGCCACGTGACCGGGTGTTCCTG
```

-continued

```
AAGGGGGGCTATAAAAGGGGGTGGGGGCGCGTTCGTCCTCACTCTCTTCCGCATCGCTGTCTGC

GAGGGCCAGCTGTTGGGGTGAGTACTCCCTCTGAAAAGCGGGCATGACTTCTGCGCTAAGATTG

TCAGTTTCCAAAAACGAGGAGGATTTGATATTCACCTGGCCCGCGGTGATGCCTTTGAGGGTGG

CCGCATCCATCTGGTCAGAAAAGACAATCTTTTTGTTGTCAAGCTTGGTGGCAAACGACCCGTAG

AGGGCGTTGGACAGCAACTTGGCGATGGAGCGCAGGGTTTGGTTTTTGTCGCGATCGGCGCGC

TCCTTGGCCGCGATGTTTAGCTGCACGTATTCGCGCGCAACGCACCGCCATTCGGGAAAGACGG

TGGTGCGCTCGTCGGGCACCAGGTGCACGCGCCAACCGCGGTTGTGCAGGGTGACAAGGTCAA

CGCTGGTGGCTACCTCTCCGCGTAGGCGCTCGTTGGTCCAGCAGAGGCGGCCGCCCTTGCGCG

AGCAGAATGGCGGTAGGGGGTCTAGCTGCGTCTCGTCCGGGGGGTCTGCGTCCACGGTAAAGA

CCCCGGGCAGCAGGCGCGCGTCGAAGTAGTCTATCTTGCATCCTTGCAAGTCTAGCGCCTGCTG

CCATGCGCGGGCGGCAAGCGCGCGCTCGTATGGGTTGAGTGGGGGACCCCATGGCATGGGGT

GGGTGAGCGCGGAGGCGTACATGCCGCAAATGTCGTAAACGTAGAGGGGCTCTCTGAGTATTCC

AAGATATGTAGGGTAGCATCTTCCACCGCGGATGCTGGCGCGCACGTAATCGTATAGTTCGTGC

GAGGGAGCGAGGAGGTCGGGACCGAGGTTGCTACGGGCGGGCTGCTCTGCTCGGAAGACTATC

TGCCTGAAGATGGCATGTGAGTTGGATGATATGGTTGGACGCTGGAAGACGTTGAAGCTGGCGT

CTGTGAGACCTACCGCGTCACGCACGAAGGAGGCGTAGGAGTCGCGCAGCTTGTTGACCAGCT

CGGCGGTGACCTGCACGTCTAGGGCGCAGTAGTCCAGGGTTTCCTTGATGATGTCATACTTATC

CTGTCCCTTTTTTTTCCACAGCTCGCGGTTGAGGACAAACTCTTCGCGGTCTTTCCAGTACTCTTG

GATCGGAAACCCGTCGGCCTCCGAACGGTAAGAGCCTAGCATGTAGAACTGGTTGACGGCCTGG

TAGGCGCAGCATCCCTTTTCTACGGGTAGCGCGTATGCCTGCGCGGCCTTCCGGAGCGAGGTGT

GGGTGAGCGCAAAGGTGTCCCTGACCATGACTTTGAGGTACTGGTATTTGAAGTCAGTGTCGTC

GCATCCGCCCTGCTCCCAGAGCAAAAAGTCCGTGCGCTTTTTGGAACGCGGATTTGGCAGGGCG

AAGGTGACATCGTTGAAGAGTATCTTTCCCGCGCGAGGCATAAAGTTGCGTGTGATGCGGAAGG

GTCCCGGCACCTCGGAACGGTTGTTAATTACCTGGGCGGCGAGCACGATCTCGTCAAAGCCGTT

GATGTTGTGGCCCACAATGTAAAGTTCCAAGAAGCGCGGGATGCCGTTGATGGAAGGCAATTTTT

TAAGTTCCTCGTAGGTGAGCTCTTCAGGGGAGCTGAGCCCGTGCTCTGAAAGGGCCCAGTCTGC

AAGATGAGGGTTGGAAGCGACGAATGAGCTCCACAGGTCACGGGCCATTAGCATTTGCAGGTGG

TCGCGAAAGGTCCTAAACTGGCGACCTATGGCCATTTTTTCTGGGGTGATGCAGTAGAAGGTAAG

CGGGTCTTGTTCCGAGGGGTCCCATCCAAGGTTCGCGGCTAGGTCTCGCGCGGCAGTCACTAGA

GGCTCATCTCCGCCGAACTTCATGACCAGCATGAAGGGCACGAGCTGCTTCCCAAAGGCCCCCA

TCCAAGTATAGGTCTCTACATCGTAGGTGACAAAGAGACGCTCGGTGCGAGGATGCGAGCCGAT

CGGGAAGAACTGGATCTCCCGCCACCAATTGGAGGAGTGGCTATTGATGTGGTGAAAGTAGAAG

TCGCTGCGAGGGGCCGAACACTCGTGCTGGCTTTTGTAAAAACGTGCGCAGTACTGGCAGGGGT

GCACGGGCTGTACATCCTGCACGAGGTTGACCTGACGACCGCGCACAAGGAAGCAGAGTGGGA

ATTTGAGCCCCTCGCCTGGCGGGTTTGGCTGGTGGTCTTCTACTTCGGCTGCTTGTCCTTGACC

GTCTGGCTGCTCGAGGGGAGTTACGGTGGATCGGACCACCACGCCGCGCGAGCCCAAAGTCCA

GATGTCCGCGCGCGGCGGTCGGAGCTTGATGACAACATCGCGCAGATGGGAGCTGTCCATGGT

CTGGAGCTCCCGCGGCGTCAGGTCAGGCGGGAGCTCCTGCAGGTTTACCTCGCATAGACGGGT

CAGGGCGCGGGCTAGATCCAGGTGATACCTAATTTCCAGGGGCTGGTTGGTGGCGGCGTCGAT

GGCTTGCAAGAGGCCGCATCCCCGCGGCGCGACTACGGTACCGCGCGGCGGGCGGTGGGCCG

CGGGGGTGTCCTTGGATGATGCATCTAAAAGCGGTGACGCGGGCGAGCCCCCGGAGGTAGGGG
```

```
GGGCTCCGGACCCGCCGGGAGAGGGGGCAGGGGCACGTCGGCGCCGCGCGCGGGCAGGAGC

TGGTGCTGCGCGCGTAGGTTGCTGGCGAACGCGACGACGCGGCGGTTGATCTCCTGAATCTGG

CGCCTCTGCGTGAAGACGACGGGCCCGGTGAGCTTGAGCCTGAAAGAGAGTTCGACAGAATCAA

TTTCGGTGTCGTTGACGGCGGCCTGGCGCAAAATCTCCTGCACGTCTCCTGAGTTGTCTTGATAG

GCGATCTCGGCCATGAACTGCTCGATCTCTTCCTCCTGGAGATCTCCGCGTCCGGCTCGCTCCA

CGGTGGCGGCGAGGTCGTTGGAAATGCGGGCCATGAGCTGCGAGAAGGCGTTGAGGCCTCCCT

CGTTCCAGACGCGGCTGTAGACCACGCCCCCTTCGGCATCGCGGGCGCGCATGACCACCTGCG

CGAGATTGAGCTCCACGTGCCGGGCGAAGACGGCGTAGTTTCGCAGGCGCTGAAAGAGGTAGT

TGAGGGTGGTGGCGGTGTGTTCTGCCACGAAGAAGTACATAACCCAGCGTCGCAACGTGGATTC

GTTGATATCCCCCAAGGCCTCAAGGCGCTCCATGGCCTCGTAGAAGTCCACGGCGAAGTTGAAA

AACTGGGAGTTGCGCGCCGACACGGTTAACTCCTCCTCCAGAAGACGGATGAGCTCGGCGACA

GTGTCGCGCACCTCGCGCTCAAAGGCTACAGGGGCCTCTTCTTCTTCTTCAATCTCCTCTTCCAT

AAGGGCCTCGCCTTCTTCTTCTTCTGGCGGCGGTGGGGGAGGGGGGACAGGGCGGCGAGGAC

GGCGCACCGGGAGGCGGTCGACAAAGCGCTCGATCATCTCCCCGCGGCGACGGCGCATGGTCT

CGGTGACGGCGCGGCCGTTCTCGCGGGGGCGCAGTTGGAAGACGCCGCCCGTCATGTCCCGG

TTATGGGTTGGCGGGGGGCTGCCATGCGGCAGGGATACGGCGCTAACGATGCATCTCAACAATT

GTTGTGTAGGTACTCCGCCGCCGAGGGACCTGAGCGAGTCCGCATCGACCGGATCGGAAAACC

TCTCGAGAAAGGCGTCTAACCAGTCACAGTCGCAAGGTAGGCTGAGCACCGTGGCGGGCGGCA

GCGGGCGGCGGTCGGGGTTGTTTCTGGCGGAGGTGCTGCTGATGATGTAATTAAAGTAGGCGG

TCTTGAGACGGCGGATGGTCGACAGAAGCACCATGTCCTTGGGTCCGGCCTGCTGAATGCGCAG

GCGGTCGGCCATGCCCCAGGCTTCGTTTTGACATCGGCGCAGGTCTTTGTAGTAGTCTTGCATG

AGCCTTTCTACCGGCACTTCTTCTTCTCCTTCCTCTTGTCCTGCATCTCTTGCATCTATCGCTGCG

GCGGCGGCGGAGTTTGGCCGTAGGTGGCGCCCTCTTCCTCCCATGCGTGTGACCCCGAAGCCC

CTCATCGGCTGAAGCAGGGCTAGGTCGGCGACAACGCGCTCGGCTAATATGGCCTGCTGCACCT

GCGTGAGGGTAGACTGGAAGTCATCCATGTCCACAAAGCGGTGGTATGCGCCCGTGTTGATGGT

GTAAGTGCAGTTGGCCATAACGGACCAGTTAACGGTCTGGTGACCCGGCTGCGAGAGCTCGGTG

TACCTGAGACGCGAGTAAGCCCTCGAGTCAAATACGTAGTCGTTGCAAGTCCGCACCAGGTACT

GGTATCCCACCAAAAAGTGCGGCGGCGGCTGGCGGTAGAGGGGCCAGCGTAGGGTGGCCGGG

GCTCCGGGGCGAGATCTTCCAACATAAGGCGATGATATCCGTAGATGTACCTGGACATCCAGG

TGATGCCGGCGGCGGTGGTGGAGGCGCGCGGAAAGTCGCGGACGCGGTTCCAGATGTTGCGC

AGCGGCAAAAAGTGCTCCATGGTCGGGACGCTCTGGCCGGTCAGGCGCGCGCAATCGTTGACG

CTCTACCGTGCAAAAGGAGAGCCTGTAAGCGGGCACTCTTCCGTGGTCTGGTGGATAAATTCGC

AAGGGTATCATGGCGGACGACCGGGGTTCGAGCCCCGTATCCGGCCGTCCGCCGTGATCCATG

CGGTTACCGCCCGCGTGTCGAACCCAGGTGTGCGACGTCAGACAACGGGGAGTGCTCCTTTT

GGCTTCCTTCCAGGCGCGGCGGCTGCTGCGCTAGCTTTTTTGGCCACTGGCCGCGCGCAGCGT

AAGCGGTTAGGCTGGAAAGCGAAAGCATTAAGTGGCTCGCTCCCTGTAGCCGGAGGGTTATTTT

CCAAGGGTTGAGTCGCGGGACCCCCGGTTCGAGTCTCGGACCGGCCGGACTGCGGCGAACGG

GGGTTTGCCTCCCCGTCATGCAAGACCCCGCTTGCAAATTCCTCCGGAAACAGGGACGAGCCCC

TTTTTTGCTTTTCCCAGATGCATCCGGTGCTGCGGCAGATGCGCCCCCCTCCTCAGCAGCGGCA

AGAGCAAGAGCAGCGGCAGACATGCAGGGCACCCTCCCCTCCTCCTACCGCGTCAGGAGGGGC
```

-continued

```
GACATCCGCGGTTGACGCGGCAGCAGATGGTGATTACGAACCCCCGCGGCGCCGGGCCGGC

ACTACCTGGACTTGGAGGAGGGCGAGGGCCTGGCGCGGCTAGGAGCGCCCTCTCCTGAGCGGT

ACCCAAGGGTGCAGCTGAAGCGTGATACGCGTGAGGCGTACGTGCCGCGGCAGAACCTGTTTC

GCGACCGCGAGGGAGAGGAGCCCGAGGAGATGCGGGATCGAAAGTTCCACGCAGGGCGCGAG

CTGCGGCATGGCCTGAATCGCGAGCGGTTGCTGCGCGAGGAGGACTTTGAGCCCGACGCGCGA

ACCGGGATTAGTCCCGCGCGCACACGTGGCGGCCGCCGACCTGGTAACCGCATACGAGCAG

ACGGTGAACCAGGAGATTAACTTTCAAAAAAGCTTTAACAACCACGTGCGTACGCTTGTGGCGCG

CGAGGAGGTGGCTATAGGACTGATGCATCTGTGGGACTTTGTAAGCGCGCTGGAGCAAAACCCA

AATAGGAAGCCGCTCATGGCGCAGCTGTTCCTTATAGTGCAGCACAGCAGGGACAACGAGGCAT

TCAGGGATGCGCTGCTAAACATAGTAGAGCCCGAGGGCCGCTGGCTGCTCGATTTGATAAACAT

CCTGCAGAGCATAGTGGTGCAGGAGCGCAGCTTGAGCCTGGCTGACAAGGTGGCCGCCATCAA

CTATTCCATGCTTAGCCTGGGCAAGTTTTACGCCCGCAAGATATACCATACCCCTTACGTTCCCAT

AGACAAGGAGGTAAAGATCGAGGGGTTCTACATGCGCATGGCGCTGAAGGTGCTTACCTTGAGC

GACGACCTGGGCGTTTATCGCAACGAGCGCATCCACAAGGCCGTGAGCGTGAGCCGGCGGCGC

GAGCTCAGCGACCGCGAGCTGATGCACAGCCTGCAAAGGGCCCTGGCTGGCACGGGCAGCGG

CGATAGAGAGGCCGAGTCCTACTTTGACGCGGGCGCTGACCTGCGCTGGGCCCCAAGCCGAGG

CGCCCTGGAGGCAGCTGGGGCCGGACCTGGGCTGGCGGTGGCACCCGCGCGCGCTGGCAACG

TCGGCGGCGTGGAGGAATATGACGAGGACGATGAGTACGAGCCAGAGGACGGCGAGTACTAAG

CGGTGATGTTTCTGATCAGATGATGCAAGACGCAACGGACCCGGCGGTGCGGGCGGCGCTGCA

GAGCCAGCCGTCCGGCCTTAACTCCACGGACGACTGGCGCCAGGTCATGGACCGCATCATGTC

GCTGACTGCGCGCAATCCTGACGCGTTCCGGCAGCAGCCGCAGGCCAACCGGCTCTCCGCAAT

TCTGGAAGCGGTGGTCCCGGCGCGCGCAAACCCCACGCACGAGAAGGTGCTGGCGATCGTAAA

CGCGCTGGCCGAAAACAGGGCCATCCGGCCCGACGAGGCCGGCCTGGTCTACGACGCGCTGC

TTCAGGGCGTGGCTCGTTACAACAGCGGCAAGGTGCAGACCAACCTGGACCGGCTGGTGGGGG

ATGTGCGCGAGGCCGTGGCGCAGCGTGAGCGCGCGCAGCAGCAGGGCAACCTGGGCTCCATG

GTTGCACTAAACGCCTTCCTGAGTACACAGCCCGCCAACGTGCCGCGGGGACAGGAGGACTACA

CCAACTTTGTGAGCGCACTGCGGCTAATGGTGACTGAGACACCGCAAAGTGAGGTGTACCAGTC

TGGGCCAGACTATTTTTTCCAGACCAGTAGACAAGGCCTGCAGACCGTAAACCTGAGCCAGGCTT

TCAAAAACTTGCAGGGGCTGTGGGGGGTGCGGGCTCCCACAGGCGACCGCGCGACCGTGTCTA

GCTTGCTGACGCCCAACTCGCGCCTGTTGCTGCTGCTAATAGCGCCCTTCACGGACAGTGGCAG

CGTGTCCCGGGACACATACCTAGGTCACTTGCTGACACTGTACCGCGAGGCCATAGGTCAGGCG

CATGTGGACGAGCATACTTTCCAGGAGATTACAAGTGTCAGCCGCGCGCTGGGGCAGGAGGACA

CGGGCAGCCTGGAGGCAACCCTAAACTACCTGCTGACCAACCGGCGGCAGAAGATCCCCTCGTT

GCACAGTTTAAACAGCGAGGAGGAGCGCATTTTGCGCTACGTGCAGCAGAGCGTGAGCCTTAAC

CTGATGCGCGACGGGGTAACGCCCAGCGTGGCGCTGGACATGACCGCGCGCAACATGGAACCG

GGCATGTATGCCTCAAACCGGCCGTTTATCAACCGCCTAATGGACTACTTGCATCGCGCGGCCG

CCGTGAACCCCGAGTATTTCACCAATGCCATCTTGAACCCGCACTGGCTACCGCCCCCTGGTTTC

TACACCGGGGATTCGAGGTGCCCGAGGGTAACGATGGATTCCTCTGGGACGACATAGACGACA

GCGTGTTTTCCCCGCAACCGCAGACCCTGCTAGAGTTGCAACAGCGCGAGCAGGCAGAGGCGG

CGCTGCGAAAGGAAAGCTTCCGCAGGCCAAGCAGCTTGTCCGATCTAGGCGCTGCGGCCCCGC

GGTCAGATGCTAGTAGCCCATTTCCAAGCTTGATAGGGTCTCTTACCAGCACTCGCACCACCCGC
```

-continued

```
CCGCGCCTGCTGGGCGAGGAGGAGTACCTAAACAACTCGCTGCTGCAGCCGCAGCGCGAAAAA

AACCTGCCTCCGGCATTTCCCAACAACGGGATAGAGAGCCTAGTGGACAAGATGAGTAGATGGA

AGACGTACGCGCAGGAGCACAGGGACGTGCCAGGCCCGCGCCCGCCCACCCGTCGTCAAAGG

CACGACCGTCAGCGGGGTCTGGTGTGGGAGGACGATGACTCGGCAGACGACAGCAGCGTCCTG

GATTTGGGAGGGAGTGGCAACCCGTTTGCGCACCTTCGCCCCAGGCTGGGGAGAATGTTTTAAA

AAAAAAAAGCATGATGCAAAATAAAAAACTCACCAAGGCCATGGCACCGAGCGTTGGTTTTCTT

GTATTCCCCTTAGTATGCGGCGCGCGGCGATGTATGAGGAAGGTCCTCCTCCCTCCTACGAGAG

TGTGGTGAGCGCGGCGCCAGTGGCGGCGGCGCTGGGTTCTCCCTTCGATGCTCCCCTGGACCC

GCCGTTTGTGCCTCCGCGGTACCTGCGGCCTACCGGGGGAGAAACAGCATCCGTTACTCTGA

GTTGGCACCCCTATTCGACACCACCCGTGTGTACCTGGTGGACAACAAGTCAACGGATGTGGCA

TCGCTGAACTACCAGAACGACCACAGGAACTTTCTGACCAGGGTCATTGAAAACAATGACTACAG

CCCGGGGGAGGCAAGCACACAGACCATCAATCTTGACGACCGGTCGCACTGGGGCGGCGACCT

GAAAACCATCCTGCATACCAACATGCCAAATGTGAACGAGTTCATGTTTACCAATAAGTTTAAGGC

GCGGGTGATGGTGTCGCGCTTGCCTACTAAGGACAATCAGGTGGAGCTGAAATACGAGTGGGTG

GAGTTGAGGCTGCCCGAGGGCAACTACTCCGAGACCATGACCATAGACCTTATGAACAACGCGA

TCGTGGAGCACTACTTGAAAGTGGGCAGACAGAACGGGGTTCTGGAAAGCGACATCGGGGTAAA

GTTTGACACCCGCAACTTCAGACTGGGGTTTGACCCCGTCACTGGTCTTGTCATGCCTGGGGTAT

ATACAAACGAAGCCTTCCATCCAGACATCATTTTGCTGCCAGGATGCGGGGTGGACTTCACCCAC

AGCCGCCTGAGGAACTTGTTGGGCATCCGCAAGGGGCAACCCTTCCAGGAGGGCTTTAGGATCA

CCTACGATGATCTGGAGGGTGGTAACATTCCCGCACTGTTGGATGTGGACGCCTACCAGGCGAG

CTTGAAAGATGACACCGAACAGGGCGGGGGTGGCGCAGGCGGCAGCAACAGCAGTGGCAGCG

GCGCGGAAGAGAACTCCAACGCGGCAGCCGCGGCAATGCAGCCGGTGGAGGACATGAACGATC

ATGCCATTCGCGGCGAGACCTTTGCCAGAGGGGCTGAGGAGAAGCGCGCTGAGGCCGAAGGAG

CGGCCGAAGCTGCCGCCCCCGCTGCGCAACCCGAGGTCGAGAAGCCTCAGAAGAAACCGGTGA

TCAAACCCCTGACAGAGGACAGCAAGAAACGCAGTTACAACCTAATAAGCAATGACAGCACCTTC

ACCCAGTACCGCAGCTGGTACCTTGCATACAACTACGGCGACCCTCAGACCGGAATCCGCTCAT

GGACCCTGCTTTGCACTCCTGACGTAACCTGCGGCTCGGAGCAGGTCTACTGGTCGTTGCCAGA

CATGATGCAAGACCCCGTGACCTTCCGCTCCACGCGCCAGATCAGCAACTTTCCGGTGGTGGGC

GCCGAGCTGTTGCCCGTGCACTCCAAGAGCTTCTACAACGACCAGGCCGTCTACTCCCAACTCA

TCCGCCAGTTTACCTCTCTGACCCACGTGTTCAATCGCTTTCCCGAGAACCAGATTTTGGCGCGC

CCGCCAGCCCCCACCATCACCACCGTCAGTGAAAACGTTCCTGCTCTCACAGATCACGGGACGC

TACCGCTGCGCAACAGCATCGGAGGAGTCCAGCGAGTGACCATTACTGACGCCAGACGCCGCA

CCTGCCCCTACGTTTACAAGGCCCTGGGCATAGTCTCGCCGCGCGTCCTATCGAGCCGCACTTT

TTGAGCAAGCATGTCCATCCTTATATCGCCCAGCAATAACACAGGCTGGGGCCTGCGCTTCCCAA

GCAAGATGTTTGGCGGGCCAAGAAGCGCTCCGACCAACACCCAGTGCGCGTGCGCGGGCACT

ACCGCGCGCCCTGGGGCGCGCACAAACGCGGCCGCACTGGGCGCACCACCGTCGATGACGCC

ATCGACGCGGTGGTGGAGGAGGCGCGCAACTACACGCCCACGCCGCCACCAGTGTCCACAGTG

GACGCGGCCATTCAGACCGTGGTGCGCGGAGCCCGGCGCTATGCTAAAATGAAGAGACGGCGG

AGGCGCGTAGCACGTCGCCACCGCCGCCGACCCGGCACTGCCGCCCAACGCGCGGCGGCGGC

CCTGCTTAACCGCGCACGTCGCACCGGCCGAGGGGCGGCCATGCGGGCCGCTCGAAGGCTGG
```

-continued

```
CCGCGGGTATTGTCACTGTGCCCCCAGGTCCAGGCGACGAGCGGCCGCCGCAGCAGCCGCG
GCCATTAGTGCTATGACTCAGGGTCGCAGGGGCAACGTGTATTGGGTGCGCGACTCGGTTAGCG
GCCTGCGCGTGCCCGTGCGCACCCGCCCGCCGCGCAACTAGATTGCAAGAAAAAACTACTTAGA
CTCGTACTGTTGTATGTATCCAGCGGCGGCGGCGCGCAACGAAGCTATGTCCAAGCGCAAAATC
AAAGAAGAGATGCTCCAGGTCATCGCGCCGGAGATCTATGGCCCCCCGAAGAAGGAAGAGCAG
GATTACAAGCCCCGAAAGCTAAAGCGGGTCAAAAAGAAAAAGAAAGATGATGATGATGAACTTGA
CGAGGAGGTGGAACTGCTGCAGGCTACCGCGCCCAGGCGAGGGGTAGAGTGGAAAGGTCGAGG
CGTAAAACGTGTTTTGCGACCCGGCACCACCGTAGTCTTTACGCCCGGTGAGCGCTCCACCCGC
ACCTACAAGCGCGTGTATGATGAGGTGTACGGCGACGAGGACCTGCTTGAGCAGGCCAACGAG
CGCCTCGGGGAGTTTGCCTACGGAAAGCGGCATAAGGACATGCTGGCGTTGCCGCTGGACGAG
GGCAACCCAACACCTAGGCTAAAGCCCGTAACACTGCAGGAGGTGCTGCCCGCGCTTGCACCGT
CCGAAGAAAAGCGCGGCCTAAAGCGCGAGTCTGGTGACTTGGCACCCACCGTGCAGCTGATGG
TACCCAAGCGCCAGCGACTGGAAGATGTCTTGGAAAAAATGACCGTGGAACCTGGGCTGGAGCC
CGAGGTCCGCGTGCGGCCAATCAAGCAGGTGGCGCCGGGACTGGGCGTGCAGACCGTGGACG
TTCAGATACCCACTACCAGTAGGACCAGTATTGCCACCGCCACAGAGGGCATGGAGACACAAAC
GTCCCCGGTTGCCTCAGCGGTGGCGGATGCCGCGGTGCAGGCGGTCGCTGCGGCCGCGTCCA
AGACCTCTACGGAGGTGCAAACGGACCCGTGGATGTTTCGCGTTTCAGCCCCCGGCGCCCGC
GCGGTTCGAGGAAGTACGGCGCCGCCAGCGCGCTACTGCCCGAATATGCCCTACATCCTTCCAT
TGCGCCTACCCGCGGCTATCGTGGCTACACCTACCGCCCCAGAAGAGGAGGAACTACCCGACGC
CGAACCACCACTGGAACCCGCCGCCGCCGTCGCCGTCGCCAGCCCGTGCTGGCCCCGATTTCC
GTGCGCAGGGTGGCTCGCGAAGGAGGCAGGACCCTGGTGCTGCCAACAGCGCGCTACCACCC
CAGCATCGTTTAAAAGCCGGTCTTTGTGGTTCTTGCAGATATGGCCCTCACCTGCCGCCTCCGTT
TCCCGGTGCCGGGATTCCGAGGAAGAATGCACCGTAGGAGGGGCATGGCCGGCCACGGCCTGA
CGGGCGGCATGCGTCGTGCGCACCACCGGCGGCGGCGCGCGTCGCACCGTCGCATGCGCGGC
GGTATCCTGCCCCTCCTTATTCCACTGATCGCCGCGGCGATTGGCGCCGTGCCCGGAATTGCAT
CCGTGGCCTTGCAGGCGCAGAGACACTGATTAAAAACAAGTTGCATGTGGAAAAATCAAAATAAA
AAGTCTGGACTCTCACGCTCGCTTGGTCCTGTAACTATTTTGTAGAATGGAAGACATCAACTTTGC
GTCTCTGGCCCCGCGACACGGCTCGCGCCCGTTCATGGGAAACTGGCAAGATATCGGCACCAG
CAATATGAGCGGTGGCGCCTTCAGCTGGGGCTCGCTGTGGAGCGGCATTAAAAATTTCGGTTCC
ACCGTTAAGAACTATGGCAGCAAGGCCTGGAACAGCAGCACAGGCCAGATGCTGAGGGATAAGT
TGAAAGAGCAAAATTTCCAACAAAAGGTGGTAGATGGCCTGGCCTCTGGCATTAGCGGGGTGGT
GGACCTGGCCAACCAGGCAGTGCAAAATAAGATTAACAGTAAGCTTGATCCCCGCCCTCCCGTA
GAGGAGCCTCCACCGGCCGTGGAGACAGTGTCTCCAGAGGGGCGTGGCGAAAAGCGTCCGCG
CCCCGACAGGGAAGAAACTCTGGTGACGCAAATAGACGAGCCTCCCTCGTACGAGGAGGCACTA
AAGCAAGGCCTGCCCACCACCCGTCCCATCGCGCCCATGGCTACCGGAGTGCTGGGCCAGCAC
ACACCCGTAACGCTGGACCTGCCTCCGCCCGCCGAGACCCAGGAGAAACCTGTGCTGCCAGGC
CCGACCGCCGTTGTTGTAACCCGTCCTAGCCGCGCGTCCCTGCGCCGCGCCGCCAGCGGTCCG
CGATCGTTGCGGCCCGTAGCCAGTGGCAACTGGCAAAGCACACTGAACAGCATCGTGGGTCTG
GGGGTGCAATCCCTGAAGCGCCGACGATGCTTCTGAATAGCTAACGTGTCGTATGTGTGTCATGT
ATGCGTCCATGTCGCCGCCAGAGGAGCTGCTGAGCCGCCGCGCGCCCGCTTTCCAAGATGGCT
ACCCCTTCGATGATGCCGCAGTGGTCTTACATGCACATCTCGGGCCAGGACGCCTCGGAGTACC
```

```
TGAGCCCCGGGCTGGTGCAGTTTGCCCGCGCCACCGAGACGTACTTCAGCCTGAATAACAAGTT

TAGAAACCCCACGGTGGCGCCTACGCACGACGTGACCACAGACCGGTCCGAGGGTTTGAGGCT

GCGGTTCATCCCTGTGGACCGTGAGGATACTGCGTACTCGTACAAGGCGCGGTTCACCCTAGCT

GTGGGTGATAACCGTGTGCTGGACATGGCTTCCACGTACTTTGACATCCGCGGCGTGCTGGACA

GGGGCCCTACTTTTAAGCCCTACTCTGGCACTGCCTACAACGCCCTGGCTCCCAAGGGTGCCCC

AAATCCTTGCGAATGGGATGAAGCTGCTACTGCTCTTGAAATAAACCTAGAAGAAGAGGAGGATG

ACAACGAAGACGAAGTAGACGAGCAAGCTGAGCAGCAAAAAACTCACGTATTTGGGCAGGCGCC

TTATTCTGGTATAAATATTACAAAGGAGGGTATTCAAATAGGTGTCGAAGGTCAAACACCTAAATA

TGCCGATAAAACATTTCAACCTGAACCTCAAATAGGAGAATCTCAGTGGTACGAAACTGAAATTAA

TCATGCAGCTGGGAGAGTCCTTAAAAAGACTACCCCAATGAAACCATGTTAGGGTTCATATGCAA

AACCCACAAATGAAATGGAGGGCAAGGCATTCTTGTAAAGCAACAAAATGGAAAGCTAGAAAGT

CAAGTGGAAATGCAATTTTTCTCAACTACTGAGGCGACCGCAGGCAATGGTGATAACTTGACTCC

TAAAGTGGTATTGTACAGTGAAGATGTAGATATAGAAACCCCAGACACTCATATTTCTTACATGCC

CACTATTAAGGAAGGTAACTGAGGAGAACTAATGGGCCAACAATCTATGCCCAACAGGCCTAATT

ACATTGCTTTTAGGGACAATTTTATTGGTCTAATGTATTACAACAGCACGGGTAATATGGGTGTTC

TGGCGGGCCAAGCATCGCAGTTGAATGCTGTTGTAGATTTGCAAGACAGAAACACAGAGCTTTCA

TACCAGCTTTTGCTTGATTCCATTGGTGATAGAACCAGGTACTTTTCTATGTGGAATCAGGCTGTT

GACAGCTATGATCCAGATGTTAGAATTATTGAAAATCATGGAACTGAAGATGAACTTCCAAATTAC

TGCTTTCCACTGGGAGGTGTGATTAATACAGAGACTCTTACCAAGGTAAAACCTAAAACAGGTCA

GGAAAATGGATGGGAAAAAGATGCTACAGAATTTTCAGATAAAAATGAAATAAGAGTTGGAAATAA

TTTTGCCATGGAAATCAATCTAAATGCCAACCTGTGGAGAAATTTCCTGTACTCCAACATAGCGCT

GTATTTGCCCGACAAGCTAAAGTACAGTCCTTCCAACGTAAAAATTTCTGATAACCCAAACACCTA

CGACTACATGAACAAGCGAGTGGTGGCTCCCGGGTTAGTGGACTGCTACATTAACCTTGGAGCA

CGCTGGTCCCTTGACTATATGGACAACGTCAACCCATTTAACCACCACCGCAATGCTGGCCTGCG

CTACCGCTCAATGTTGCTGGGCAATGGTCGCTATGTGCCCTTCCACATCCAGGTGCCTCAGAAGT

TCTTTGCCATTAAAAACCTCCTTCTCCTGCCGGGCTCATACACCTACGAGTGGAACTTCAGGAAG

GATGTTAACATGGTTCTGCAGAGCTCCCTAGGAAATGACCTAAGGGTTGAGGGAGCCAGGATTAA

GTTTGATAGCATTTGCCTTTACGCCACCTTCTTCCCCATGGCCCACAACACCGCCTCCACGCTTG

AGGCCATGCTTAGAAACGACACCAACGACCAGTCCTTTAACGACTATCTCTCCGCCGCCAACATG

CTCTACCCTATACCCGCCAACGCTACCAACGTGCCCATATCCATCCCCTCCCGCAACTGGGCGG

CTTTCCGCGGCTGGGCCTTGAGGCGCCTTAAGACTAAGGAAACCCCATCACTGGGCTCGGGCTA

CGACCCTTATTACACCTACTCTGGCTCTATACCCTACCTAGATGGAACCTTTTACCTCAACCACAC

CTTTAAGAAGGTGGCCATTACCTTTGACTCTTCTGTCAGCTGGCCTGGCAATGACCGCCTGCTTA

CCCCCAACGAGTTTGAAATTAAGCGCTCAGTTGACGGGGAGGGTTACAACGTTGCCCAGTGTAA

CATGACCAAAGACTGGTTCCTGGTACAAATGCTAGCTAACTACAACATTGGCTACCAGGGCTTCT

ATATCCCAGAGAGCTACAAGGACCGCATGTACTCCTTCTTTAGAAACTTCCAGCCCATGAGCCGT

CAGGTGGTGGATGATACTAAATACAAGGACTACCAACAGGTGGGCATCCTACACCAACACAACAA

CTCTGGATTTGTTGGCTACCTTGCCCCCACCATGCGCGAAGGACAGGCCTACCCTGCTAACTTCC

CCTATCCGCTTATAGGCAAGACCGCAGTTGACAGCATTACCCAGAAAAAGTTTCTTTGCGATCGC

ACCCTTTGGCGCATCCCATTCTCCAGTAACTTTATGTCCATGGGCGCACTCACAGACCTGGGCCA
```

-continued

```
AAACCTTCTCTACGCCAACTCCGCCCACGCGCTAGACATGACTTTTGAGGTGGATCCCATGGACG

AGCCCACCCTTCTTTATGTTTTGTTTGAAGTCTTTGACGTGGTCCGTGTGCACCGGCCGCACCGC

GGCGTCATCGAAACCGTGTACCTGCGCACGCCCTTCTCGGCCGGCAACGCCACAACATAAAGAA

GCAAGCAACATCAACAACAGCTGCCGCCATGGGCTCCAGTGAGCAGGAACTGAAAGCCATTGTC

AAAGATCTTGGTTGTGGGCCATATTTTTTGGGCACCTATGACAAGCGCTTTCCAGGCTTTGTTTCT

CCACACAAGCTCGCCTGCGCCATAGTCAATACGGCCGGTCGCGAGACTGGGGCCGTACACTGG

ATGGCCTTTGCCTGGAACCCGCACTCAAAAACATGCTACCTCTTTGAGCCCTTTGGCTTTTCTGA

CCAGCGACTCAAGCAGGTTTACCAGTTTGAGTACGAGTCACTCCTGCGCCGTAGCGCCATTGCTT

CTTCCCCCGACCGCTGTATAACGCTGGAAAAGTCCACCCAAAGCGTACAGGGGCCCAACTCGGC

CGCCTGTGGACTATTCTGCTGCATGTTTCTCCAGGCCTTTGCCAACTGGCCCCAAACTCCCATGG

ATCACAACCCCACCATGAACCTTATTACCGGGGTACCCAACTCCATGCTCAACAGTCCCCAGGTA

CAGCCCACCCTGCGTCGCAACCAGGAACAGCTCTACAGCTTCCTGGAGCGCCACTCGCCCTACT

TCCGCAGCCACAGTGCGCAGATTAGGAGCGCCACTTCTTTTTGTCACTTGAAAAACATGTAAAAA

TAATGTACTAGAGACACTTTCAATAAAGGCAAATGCTTTTATTTGTACACTCTCGGGTGATTATTTA

CCCCCACCCTTGCCGTCTGCGCCGTTTAAAAATCAAAGGGGTTCTGCCGCGCATCGCTATGCGC

CACTGGCAGGGACACGTTGCGATACTGGTGTTTAGTGCTCCACTTAAACTCAGGCACAACCATCC

GCGGCAGCTCGGTGAAGTTTTCACTCCACAGGCTGCGCACCATCACCAACGCGTTTAGCAGGTC

GGGCGCCGATATCTTGAAGTCGCAGTTGGGGCCTCCGCCCTGCGCGCGCGAGTTGCGATACAC

AGGGTTGCAGCACTGGAACACTATCAGCGCCGGGTGGTGCACGCTGGCCAGCACGCTCTTGTC

GGAGATCAGATCCGCGTCCAGGTCCTCCGCGTTGCTCAGGGCGAACGGAGTCAACTTTGGTAGC

TGCCTTCCCAAAAAGGGCGCGTGCCCAGGCTTTGAGTTGCACTCGCACCGTAGTGGCATCAAAA

GGTGACCGTGCCCGGTCTGGGCGTTAGGATACAGCGCCTGCATAAAAGCCTTGATCTGCTTAAA

AGCCACCTGAGCCTTTGCGCCTTCAGAGAAGAACATGCCGCAAGACTTGCCGGAAAACTGATTG

GCCGGACAGGCCGCGTCGTGCACGCAGCACCTTGCGTCGGTGTTGGAGATCTGCACCACATTTC

GGCCCCACCGGTTCTTCACGATCTTGGCCTTGCTAGACTGCTCCTTCAGCGCGCGCTGCCCGTT

TTCGCTCGTCACATCCATTTCAATCACGTGCTCCTTATTTATCATAATGCTTCCGTGTAGACACTTA

AGCTCGCCTTCGATCTCAGCGCAGGGGTGCAGCCACAAGGCGCAGCCCGTGGGCTCGTGATGC

TTGTAGGTCACCTCTGCAAACGACTGCAGGTACGCCTGCAGGAATCGCCCCATCATCGTCACAAA

GGTCTTGTTGCTGGTGAAGGTCAGCTGCAACCCGCGGTGCTCCTCGTTCAGCCAGGTCTTGCAT

ACGGCCGCCAGAGCTTCCACTTGGTCAGGCAGTAGTTTGAAGTTCGCCTTTAGATCGTTATCCAC

GTGGTACTTGTCCATCAGCGCGCGCGCAGCCTCCATGCCCTTCTCCCACGCAGACACGATCGGC

ACACTCAGCGGGTTCATCACCGTAATTTCACTTTCCGCTTCGCTGGGCTCTTCCTCTTCCTCTTGC

GTCCGCATACCACGCGCCACTGGGTCGTCTTCATTCAGCCGCCGCACTGTGCGCTTACCTCCTT

TGCCATGCTTGATTAGCACCGGTGGGTTGCTGAAACCCACCATTTGTAGCGCCACATCTTCTCTT

TCTTCCTCGCTGTCCACGATTACCTCTGGTGATGGCGGGCGCTCGGGCTTGGGAGAAGGGCGCT

TCTTTTTCTTCTTGGGCGCAATGGCCAAATCCGCCGCCGAGGTCGATGGCCGCGGGCTGGGTGT

GCGCGGCACCAGCGCGTCTTGTGATGAGTCTTCCTCGTCCTCGGACTCGATACGCCGCCTCATC

CGCTTTTTTGGGGGCGCCCGGGGAGGCGGCGGCGACGGGACGGGGACGACACGTCCTCCAT

GGTTGGGGGACGTCGCGCCGCACCGCGTCCGCGCTCGGGGGTGGTTTCGCGCTGCTCCTCTTC

CCGACTGGCCATTTCCTTCTCCTATAGGCAGAAAAAGATCATGGAGTCAGTCGAAGAAGGACA

GCCTAACCGCCCCCTCTGAGTTCGCCACCACCGCCTCCACCGATGCCGCCAACGCGCCTACCAC
```

-continued

```
CTTCCGCGTCGAGGCACCCCCGCTTGAGGAGGAGGAAGTGATTATCGAGCAGGACCCAGGTTTT
GTAAGCGAAGACGACGAGGACCGCTCAGTACCAACAGAGGATAAAAAGCAAGACCAGGACAACG
CAGAGGCAAACGAGGAACAAGTCGGGCGGGGGGACGAAAGGCATGGCGACTACCTAGATGTGG
GAGACGACGTGCTGTTGAAGCATCTGCAGCGCCAGTGCGCCATTATCTGCGACGCGTTGCAAGA
GCGCAGCGATGTGCCCCTCGCCATAGCGGATGTGAGCCTTGCCTACGAACGCCACCTATTCTCA
CCGCGCGTACCCCCAAACGCCAAGAAAACGGCACATGCGAGCCCAACCCGCGCCTCAACTTCT
ACCCCGTATTTGCCGTGCCAGAGGTGCTTGCCACCTATCACATCTTTTTCCAAAACTGCAAGATA
CCCCTATCCTGCCGTGCCAACCGCAGCCGAGCGGACAAGCAGCTGGCCTTGCGGCAGGGCGCT
GTCATACCTGATATCGCCTCGCTCAACGAAGTGCCAAAAATCTTTGAGGGTCTTGGACGCGACGA
GAAGCGCGCGGCAAACGCTCTGCAACAGGAAAACAGCGAAAATGAAAGTCACTCTGGAGTGTTG
GTGGAACTCGAGGGTGACAACGCGCGCCTAGCCGTACTAAAACGCAGCATCGAGGTCACCCACT
TTGCCTACCCGGCACTTAACCTACCCCCCAAGGTCATGAGCACAGTCATGAGTGAGCTGATCGT
GCGCCGTGCGCAGCCCCTGGAGAGGGATGCAAATTTGCAAGAACAAACAGAGGAGGGCCTACC
CGCAGTTGGCGACGAGCAGCTAGCGCGCTGGCTTCAAACGCGCGAGCCTGCCGACTTGGAGGA
GCGACGCAAACTAATGATGGCCGCAGTGCTCGTTACCGTGGAGCTTGAGTGCATGCAGCGGTTC
TTTGCTGACCCGGAGATGCAGCGCAAGCTAGAGGAAACATTGCACTACACCTTTCGACAGGGCT
ACGTACGCCAGGCCTGCAAGATCTCCAACGTGGAGCTCTGCAACCTGGTCTCCTACCTTGGAATT
TTGCACGAAAACCGCCTTGGGCAAAACGTGCTTCATTCCACGCTCAAGGGCGAGGCGCGCCGC
GACTACGTCCGCGACTGCGTTTACTTATTTCTATGCTACACCTGGCAGACGGCCATGGGCGTTTG
GCAGCAGTGCTTGGAGGAGTGCAACCTCAAGGAGCTGCAGAAACTGCTAAAGCAAAACTTGAAG
GACCTATGGACGGCCTTCAACGAGCGCTCCGTGGCCGCGCACCTGGCGGACATCATTTTCCCCG
AACGCCTGCTTAAAACCCTGCAACAGGGTCTGCCAGACTTCACCAGTCAAAGCATGTTGCAGAAC
TTTAGGAACTTTATCCTAGAGCGCTCAGGAATCTTGCCCGCCACCTGCTGTGCACTTCCTAGCGA
CTTTGTGCCCATTAAGTACCGCGAATGCCCTCCGCCGCTTTGGGGCCACTGCTACCTTCTGCAG
CTAGCCAACTACCTTGCCTACCACTCTGACATAATGGAAGACGTGAGCGGTGACGGTCTACTGGA
GTGTCACTGTCGCTGCAACCTATGCACCCCGCACCGCTCCCTGGTTTGCAATTCGCAGCTGCTTA
ACGAAAGTCAAATTATCGGTACCTTTGAGCTGCAGGGTCCCTCGCCTGACGAAAGTCCGCGGC
TCCGGGGTTGAAACTCACTCCGGGGCTGTGGACGTCGGCTTACCTTCGCAAATTTGTACCTGAG
GACTACCACGCCCACGAGATTAGGTTCTACGAAGACCAATCCCGCCCGCCAAATGCGGAGCTTA
CCGCCTGCGTCATTACCCAGGGCCACATTCTTGGCCAATTGCAAGCCATCAACAAAGCCCGCCA
AGAGTTTCTGCTACGAAAGGGACGGGGGGTTTACTTGGACCCCCAGTCCGGCGAGGAGCTCAAC
CCAATCCCCCCGCCGCCGCAGCCCTATCAGCAGCAGCCGCGGGCCCTTGCTTCCCAGGATGGC
ACCCAAAAAGAAGCTGCAGCTGCCGCCGCCACCCACGGAGGAGGAGGAATACTGGGACAGTCA
GGCAGAGGAGGTTTTGGACGAGGAGGAGGAGGACATGATGGAAGACTGGGAGAGCCTAGACGA
GGAAGCTTCCGAGGTCGAAGAGGTGTCAGACGAAACACCGTCACCCTCGGTCGCATTCCCCTCG
CCGGCGCCCCAGAAATCGGCAACCGGTTCCAGCATGGCTACAACCTCCGCTCCTCAGGCGCCG
CCGGCACTGCCCGTTCGCCGACCCAACCGTAGATGGGACACCACTGGAACCAGGGCCGGTAAG
TCCAAGCAGCCGCCGCCGTTAGCCCAAGAGCAACAACAGCGCCAAGGCTACCGCTCATGGCGC
GGGCACAAGAACGCCATAGTTGCTTGCTTGCAAGACTGTGGGGGCAACATCTCCTTCGCCCGCC
GCTTTCTTCTCTACCATCACGGCGTGGCCTTCCCCCGTAACATCCTGCATTACTACCGTCATCTCT
```

-continued

```
ACAGCCCATACTGCACCGGCGGCAGCGGCAGCGGCAGCAACAGCAGCGGCCACACAGAAGCAA

AGGCGACCGGATAGCAAGACTCTGACAAAGCCCAAGAAATCCACAGCGGCGGCAGCAGCAGGA

GGAGGAGCGCTGCGTCTGGCGCCCAACGAACCCGTATCGACCCGCGAGCTTAGAAACAGGATT

TTTCCCACTCTGTATGCTATATTTCAACAGAGCAGGGGCCAAGAACAAGAGCTGAAAATAAAAAAC

AGGTCTCTGCGATCCCTCACCCGCAGCTGCCTGTATCACAAAAGCGAAGATCAGCTTCGGCGCA

CGCTGGAAGACGCGGAGGCTCTCTTCAGTAAATACTGCGCGCTGACTCTTAAGGACTAGTTTCG

CGCCCTTTCTCAAATTTAAGCGCGAAAACTACGTCATCTCCAGCGGCCACACCCGGCGCCAGCA

CCTGTCGTCAGCGCCATTATGAGCAAGGAAATTCCCACGCCCTACATGTGGAGTTACCAGCCACA

AATGGGACTTGCGGCTGGAGCTGCCCAAGACTACTCAACCCGAATAAACTACATGAGCGCGGGA

CCCCACATGATATCCCGGGTCAACGGAATCCGCGCCCACCGAAACCGAATTCTCTTGGAACAGG

CGGCTATTACCACCACACCTCGTAATAACCTTAATCCCCGTAGTTGGCCCGCTGCCCTGGTGTAC

CAGGAAAGTCCCGCTCCCACCACTGTGGTACTTCCCAGAGACGCCCAGGCCGAAGTTCAGATGA

CTAACTCAGGGGCGCAGCTTGCGGGCGGCTTTCGTCACAGGGTGCGGTCGCCCGGGCAGGGTA

TAACTCACCTGACAATCAGAGGGCGAGGTATTCAGCTCAACGACGAGTCGGTGAGCTCCTCGCT

TGGTCTCCGTCCGGACGGGACATTTCAGATCGGCGGCGCCGGCCGTCCTTCATTCACGCCTCGT

CAGGCAATCCTAACTCTGCAGACCTCGTCCTCTGAGCCGCGCTCTGGAGGCATTGGAACTCTGC

AATTTATTGAGGAGTTTGTGCCATCGGTCTACTTTAACCCCTTCTCGGGACCTCCCGGCCACTAT

CCGGATCAATTTATTCCTAACTTTGACGCGGTAAAGGACTCGGCGGACGGCTACGACTGAATGTT

AAGTGGAGAGGCAGAGCAACTGCGCCTGAAACACCTGGTCCACTGTCGCCGCCACAAGTGCTTT

GCCCGCGACTCCGGTGAGTTTTGCTACTTTGAATTGCCCGAGGATCATATCGAGGGCCCGGCGC

ACGGCGTCCGGCTTACCGCCCAGGGAGAGCTTGCCCGTAGGCTGATTCGGGAGTTTACCCAGG

GCCCCCTGCTAGTTGAGCGGGACAGGGGACCCTGTGTTCTCACTGTGATTTGCAACTGTCCTAA

CCTTGGATTACATCAAGATCCTCTAGTTATAACTAGAGTACCCGGGGATCTTATTCCCTTTAACTA

ATAAAAAAAAATAATAAAGCATCACTTACTTAAAATCAGTTAGCAAATTTCTGTCCAGTTTATTCAG

GAGCACCTCCTTGCGCTCCTCCCAGCTCTGGTATTGGAGCTTCCTCCTGGCTGCAAACTTTCTCC

ACAATCTAAATGGAATGTCAGTTTCCTCCTGTTCCTGTCCATCCGCACCCACTATCTTCATGTTGT

TGCAGATGAAGCGCGCAAGACCGTCTGAAGATACCTTCAACCCCGTGTATCCATATGACACGGAA

ACCGGTCCTCCAACTGTGCCTTTTCTTACTCCTCCCTTTGTATCCCCCAATGGGTTTCAAGAGAGT

CCGCCTGGGGTACTCTCTTTGCGCCTATCCGAACCTCTAGTTACCTCCAATGGCATGCTTGCGCT

CAAAATGGGCAACGGCCTCTCTCTGGACGAGGCCGGCAACCTTACCTCCCAAAATGTAACCACT

GTGAGCCCACCTCTCAAAAAAACCAAGTCAAACATAAACCTGGAAATATCTGCACCCCTCACAGT

TACCTCAGAAGCCCTAACTGTGGCTGCCGCCGCACCTCTAATGGTCGCGGGCAACACACTCACC

ATGCAATCAGAGGCCGCGCTAACCGTGCAGGACTCCAAACTTAGGATTGCCACCCAAGGACCCC

TCACAGTGTCAGAAGGAAAGCTAGCCCTGCAAACATCAGGCCCCCTCACCACCACCGATAGCAG

TACCCTTACTATCACTGCCTCACCCCCTCTAACTACTGCCACTGGTAGCTTGGGCATTGACTTGAA

AGAGCCCATTTATACACAAAATGGAAAACTAGGACTAAAGTACGGGGCTCCTTTGCATGTAACAG

ACGAGCTAAACACTTTGACCGTAGCAACTGGTCCAGGTGTGACTATTAATAATACTTCCTTGCAAA

CTAAAGTTACTGGAGCCTTGGGTTTTGATTCACAAGGCAATATGCAACTTAATGTAGCAGGAGGA

CTAAGGATTGATTCTCAAAACAGACGCCTTATACTTGATGTTAGTTATCCGTTTGATGCTCAAAAC

CAACTAAATCTAAGACTAGGACAGGGCCCTCTTTTTATAAACTCAGCCCACAACTTGGATATTAAC

TACAACAAAGGCCTTTACTTGTTTACAGCTTCAAACAATTCCAAAAAGCTTGAGGTTAACCTAAGC
```

ACTGCCAAGGGGTTGATGTTTGACGCTACAGCCATAGCCATTAATGCAGGAGATGGGCTTGAATT

TGGTTCACCTAATGCACCAAACACAAATCCCCTCAAAACAAAAATTGGCCATGGCCTAGAATTTGA

TTCAAACAAGGCTATGGTTCCTAAACTAGGAACTGGCCTTAGTTTTGACAGCACAGGTGCCATTA

CAGTAGGAAACAAAAATAATGATAAGCTAACTTTGTGGACCACACCAGCTCCATCTCCTAACTGTA

GACTAAATGCAGAGAAAGATGCTAAACTCACTTTGGTCTTAACAAAATGTGGCAGTCAAATACTTG

CTACAGTTTCAGTTTTGGCTGTTAAAGGCAGTTTGGCTCCAATATCTGGAACAGTTCAAAGTGCTC

ATCTTATTATAAGATTTGACGAAAATGGAGTGCTACTAAACAATTCCTTCCTGGACCCAGAATATT

GGAACTTTAGAAATGGAGATCTTACTGAAGGCACAGCCTATACAAACGCTGTTGGATTTATGCCTA

ACCTATCAGCTTATCCAAAATCTCACGGTAAAACTGCCAAAAGTAACATTGTCAGTCAAGTTTACT

TAAACGGAGACAAAACTAAACCTGTAACACTAACCATTACACTAAACGGTACACAGGAAACAGGA

GACACAACTCCAAGTGCATACTCTATGTCATTTTCATGGGACTGGTCTGGCCACAACTACATTAAT

GAAATATTTGCCACATCCTCTTACACTTTTTCATACATTGCCCAAGAATAAAGAATCGTTTGTGTTA

TGTTTGAACGTGTTTATTTTTCAATTGCAGAAAATTTCAAGTCATTTTTGATTGAGTAGTATAGGCC

CACCACCACATAGCTTATACAGATCACCGTACCTTAATCAAAC pSSI10902 (SEQ ID NO: 2):
AATGTAGTCTTATGCAATACTCTTGTAGTCTTGCAACATGGTAACGATGAGTTAGCAACATGCCTT

ACAAGGAGAGAAAAAGCACCGTGCATGCCGATTGGTGGAAGTAAGGTGGTACGATCGTGCCTTA

TTAGGAAGGCAACAGACGGGTCTGACATGGATTGGACGAACCACTGAATTGCCGCATTGCAGAG

ATATTGTATTTAAGTGCCTAGCTCGATACATAAACGGGTCTCTCGGTTAGACCAGATCTGAGCCT

GGGAGCTCTCTGGCTAACTAGGGAACCCACTGCTTAAGCCTCAATAAAGCTTGCCTTGAGTGCTT

CAAGTAGTGTGTGCCCGTCTGTTGTGTGACTCTGGTAACTAGAGATCCCTCAGACCCTTTTAGTC

AGTGTGGAAAATCTCTAGCAGTGGCGCCCGAACAGGGACTTGAAAGCGAAAGGGAAACCAGAGG

AGCTCTCTCGACGCAGGACTCGGCTTGCTGAAGCGCGCACGGCAAGAGGCGAGGGGCGGCGA

CTGGTGAGTACGCCAAAAATTTTGACTAGCGGAGGCTAGAAGGAGAGAGATGGGTGCGAGAGCG

TCAGTATTAAGCGGGGGAGAATTAGATCGCGATGGGAAAAAATTCGGTTAAGGCCAGGGGGAAA

GAAAAAATATAAATTAAAACATATAGTATGGGCAAGCAGGGAGCTAGAACGATTCGCAGTTAATCC

TGGCCTGTTAGAAACATCAGAAGGCTGTAGACAAATACTGGGACAGCTACAACCATCCCTTCAGA

CAGGATCAGAAGAACTTAGATCATTATATAATACAGTAGGAACCCTCTATTGTGTGCATCAAAGGA

TAGAGATAAAAGACACCAAGGAAGCTTTAGACAAGATAGAGGAAGAGCAAAACAAAAGTAAGACC

ACCGCACAGCAAGCGGCCGCTGATCTTCAGACCTGGAGGAGGAGATATGAGGGACAATTGGAG

AAGTGAATTATATAAATATAAAGTAGTAAAAATTGAACCATTAGGAGTAGCACCCACCAAGGCAAA

GAGAAGAGTGGTGCAGAGAGAAAAAAGAGGAGTGGGAATAGGAGCTTTGTTCCTTGGGTTCTTG

GGAGCAGCAGGAAGCACTATGGGCGCAGCGTCAATGACGCTGACGGTACAGGCCAGACAATTAT

TGTCTGGTATAGTGCAGCAGCAGAACAATTTGCTGAGGGCTATTGAGGCGCAACAGCATCTGTTG

CAACTCACAGTCTGGGGCATCAAGCAGCTCCAGGCAAGAATCCTGGCTGTGGAAAGATACCTAA

AGGATCAACAGCTCCTGGGGATTTGGGGTTGCTCTGGAAAACTCATTTGCACCACTGCTGTGCCT

TGGAATGCTAGTTGGAGTAATAAATCTCTGGAACAGATTTGGAATCACACGACCTGGATGGAGTG

GGACAGAGAAATTAACAATTACACAAGCTTAATACACTCCTTAATTGAAGAATCGCAAAACCAGCA

AGAAAAGAATGAACAAGAATTATTGGAATTAGATAAATGGGCAAGTTTGTGGAATTGGTTTAACAT

AACAAATTGGCTGTGGTATATAAAATTATTCATAATGATAGTAGGAGGCTTGGTAGGTTTAAGAAT

AGTTTTTGCTGTACTTTCTATAGTGAATAGAGTTAGGCAGGGATATTCACCATTATCGTTTCAGAC

-continued

```
CCACCTCCCAACCCCGAGGGGACCCGACAGGCCCGAAGGAATAGAAGAAGAAGGTGGAGAGAG
AGACAGAGACAGATCCATTCGATTAGTGAACGGATCTCGACGGTATCGATTGGGCCCGAGATCT
CGCGCGCGAGGCCTGCCATGGGCATGCCTGCAGGTCGATGCGTGGCCGGCCTAGGATCCATAT
GGTACCGGTAAATGGCCCGCCTGGCTGACCGCCCAACGACCCCCGCCCATTGACGTCAATAATG
ACGTATGTTCCCATAGTAACGCCAATAGGGACTTTCCATTGACGTCAATGGGTGGAGTATTTACG
GTAAACTGCCCACTTGGCAGTACATCAAGTGTATCATATGCCAAGTACGCCCCCTATTGACGTCA
ATGACGGTAAATGGCCCGCCTGGCATTATGCCCAGTACATGACCTTATGGGACTTTCCTACTTGG
CAGTACATCTAGTATTAGTCATCGCTATTACCATGGTGATGCGGTTTTGGCAGTACATCAATGGGC
GTGGATAGCGGTTTGACTCACGGGGATTTCCAAGTCTCCACCCCATTGACGTCAATGGGAGTTTG
TTTTGGCACCAAAATCAACGGGACTTTCCAAAATGTCGTAACAACTCCGCCCCATTGACGCAAAT
GGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCC
GCGGCCGGGAACGGTGCATTGGAACGCGGATTCCCCGTGCCAAGAGTGACGTAAGTACCGCCT
ATAGACTCTATAGGCACACCCCTTTGGCTCTTATGCATGAATTAATAGGACTCACTATAGGGAGAC
AGACTGTTCCTTTCCTGGGTCTTTTCTGCAGGCTAGCCCCACCATGCCGCGCGCTCCCCGCTGC
CGAGCCGTGCGCTCCCTGCTGCGCAGCCACTACCGCGAGGTGCTGCCGCTGGCCACGTTCGTG
CGGCGCCTGGGGCCCCAGGGCTGGCGGCTGGTGCAGCGCGGGACCCGGCGGCTTTCCGCG
CGCTGGTGGCCCAGTGCCTGGTGTGCGTGCCCTGGGACGCACGGCCGCCCCCGCCGCCGCC
TCCTTCCGCCAGGTGTCCTGCCTGAAGGAGCTGGTGGCCCGAGTGCTGCAGAGGCTGTGCGAG
CGCGGCGCGAAGAACGTGCTGGCCTTCGGCTTCGCGCTGCTGGACGGGGCCCGCGGGGGCCC
CCCCGAGGCCTTCACCACCAGCGTGCGCAGCTACCTGCCCAACACGGTGACCGACGCACTGCG
GGGGAGCGGGCGTGGGGGCTGCTGTTGCGCCGCGTGGGCGACGACGTGCTGGTTCACCTGC
TGGCACGCTGCGCGCTCTTTGTGCTGGTGGCTCCCAGCTGCGCCTACCAGGTGTGCGGGCCGC
CGCTGTACCAGCTCGGCGCTGCCACTCAGGCCCGGCCCCCGCCACACGCTAGTGGACCCCGAA
GGCGTCTGGGATGCGAACGGGCCTGGAACCATAGCGTCAGGGAGGCCGGGGTCCCCCTGGGC
CTGCCAGCCCCGGGTGCGAGGAGGCGCGGGGGCAGTGCCAGCCGAAGTCTGCCGTTGCCCAA
GAGGCCCAGGCGTGGCGCTGCCCCTGAGCCGGAGCGGACGCCCGTTGGGCAGGGGTCCTGGG
CCCACCCGGGCAGGACGCGTGGACCGAGTGACCGTGGTTTCTGTGTGGTGTCACCTGCCAGAC
CCGCCGAAGAAGCCACCTCTTTGGAGGGTGCGCTCTCTGGCACGCGCCACTCCCACCCATCCGT
GGGCCGCCAGCACCACGCGGGCCCCCATCCACATCGCGGCCACCACGTCCCTGGGACACGC
CTTGTCCCCGGTGTACGCCGAGACCAAGCACTTCCTCTACTCCTCAGGCGACAAGGAGCAGCT
GCGGCCCTCCTTCCTACTCAGCTCTCTGAGGCCCAGCCTGACTGGCGCTCGGAGGCTCGTGGA
GACCATCTTTCTGGGTTCCAGGCCCTGGATGCCAGGGACTCCCCGCAGGTTGCCCCGCCTGCC
CCAGCGCTACTGGCAAATGCGGCCCCTGTTTCTGGAGCTGCTTGGGAACCACGCGCAGTGCCC
CTACGGGGTGCTCCTCAAGACGCACTGCCCGCTGCGAGCTGCGGTCACCCCAGCAGCCGGTGT
CTGTGCCCGGGAGAAGCCCCAGGGCTCTGTGGCGGCCCCGAGGAGGAGGACACAGACCCCC
GTCGCCTGGTGCAGCTGCTCCGCCAGCACAGCAGCCCCTGGCAGGTGTACGGCTTCGTGCGGG
CCTGCCTGCGCCGGCTGGTGCCCCAGGCCTCTGGGGCTCCAGGCACAACGAACGCCGCTTCC
TCAGGAACACCAAGAAGTTCATCTCCCTGGGGAAGCATGCCAAGCTCTCGCTGCAGGAGCTGAC
GTGGAAGATGAGCGTGCGGGCTGCGCTTGGCTGCGCAGGAGCCCAGGGGTTGGCTGTGTTCC
```

-continued

```
GGCCGCAGAGCACCGTCTGCGTGAGGAGATCCTGGCCAAGTTCCTGCACTGGCTGATGAGTGT
GTACGTCGTCGAGCTGCTCAGGTCTTTCTTTTATGTCACGGAGACCACGTTTCAAAAGAACAGGC
TCTTTTTCTACCGGAAGAGTGTCTGGAGCAAGTTGCAAAGCATTGGAATCAGACAGCACTTGAAG
AGGGTGCAGCTGCGGGAGCTGTCGGAAGCAGAGGTCAGGCAGCATCGGGAAGCCAGGCCCGC
CCTGCTGACGTCCAGACTCCGCTTCATCCCCAAGCCTGACGGGCTGCGGCCGATTGTGAACATG
GACTACGTCGTGGGAGCCAGAACGTTCCGCAGAGAAAAGAGGGCCGAGCGTCTCACCTCCAGG
GTGAAGGCACTGTTCAGCGTGCTCAACTACGAGCGGGCGCGGCGCCCCGGCCTCCTGGGCGCC
TCTGTGCTGGGCCTGGACGATATCCACAGGGCCTGGCGCACCTTCGTGCTGCGTGTGCGGGCC
CAGGACCCGCCGCCTGAGCTGTACTTTGTCAAGGTGGATGTGACGGGCGCGTACGACACCATCC
CCCAGGACAGGCTCACGGAGGTCATCGCCAGCATCATCAAACCCCAGAACACGTACTGCGTGCG
TCGGTATGCCGTGGTCCAGAAGGCCGCCCATGGGCACGTCCGCAAGGCCTTCAAGAGCCACGT
CTCTACCTTGACAGACCTCCAGCCGTACATGCGACAGTTCGTGGCTCACCTGCAGGAGACCAGC
CCGCTGAGGGATGCCGTCGTCATCGAGCAGAGCTCCTCCCTGAATGAGGCCAGCAGTGGCCTC
TTCGAGGTCTTCCTACGCTTCATGTGCCACCACGCCGTGCGCATCAGGGGCAAGTCCTACGTCC
AGTGCCAGGGGATCCCGCAGGGCTCCATCCTCTCCACGCTGCTCTGCAGCCTGTGCTACGGCG
ACATGGAGAACAAGCTGTTTGCGGGGATTCGGCGGGACGGGCTGCTCCTGCGTTTGGTGGATG
ATTTCTTGTTGGTGACACCTCACCTCACCCACGCGAAAACCTTCCTCAGGACCCTGGTCCGAGGT
GTCCCTGAGTATGGCTGCGTGGTGAACTTGCGGAAGAGAGTGGTGAACTTCCCTGTAGAAGACG
AGGCCCTGGGTGGCACGGCTTTTGTTCAGATGCCGGCCCACGGCCTATTCCCTGGTGCGGCC
TGCTGCTGGATACCCGGACCCTGGAGGTGCAGAGCGACTACTCCAGCTATGCCCGGACCTCCAT
CAGAGCCAGTCTCACCTTCAACCGCGGCTTCAAGGCTGGGAGGAACATGCGTCGCAAACTCTTT
GGGGTCTTGCGGCTGAAGTGTCACAGCCTGTTTCTGGATTTGCAGGTGAACAGCCTCCAGAGGG
TGTGCACCAACATCTACAAGATCCTCCTGCTGCAGGCGTACAGGTTTCACGCATGTGTGCTGCAG
CTCCCATTTCATCAGCAAGTTTGGAAGAACCCCACATTTTTCCTGCGCGTCATCTCTGACACGGC
CTCCCTCTGCTACTCCATCCTGAAAGCCAAGAACGCAGGGATGTCGCTGGGGGCCAAGGGCGC
CGCCGGCCCTCTGCCCTCCGAGGCCGTGCAGTGGCTGTGCCACCAAGCATTCCTGCTCAAGCT
GACTCGACACCGTGTCACCTACGTGCCACTCCTGGGGTCACTCAGGACAGCCCAGACGCAGCTG
AGTCGGAAGCTCCCGGGGACGACGCTGACTGCCCTGGAGGCCGCAGCCAACCCGGCACTGCC
CTCAGACTTCAAGACCATCCTGGACTGAGTCGAAACTCGAGGATCCGGCTGTGGAATGTGTGTC
AGTTAGGGTGTGGAAAGTCCCCAGGCTCCCCAGCAGGCAGAAGTATGCAAAGCATGCATCTCAA
TTAGTCAGCAACCAGGTGTGGAAAGTCCCCAGGCTCCCCAGCAGGCAGAAGTATGCAAAGCATG
CATCTCAATTAGTCAGCAACCATAGTCCCGCCCCTAACTCCGCCCATCCCGCCCCTAACTCCGCC
CAGTTCCGCCCATTCTCCGCCCCATGGCTGACTAATTTTTTTATTTATGCAGAGGCCGAGGCCG
CCTCGGCCTCTGAGCTATTCCAGAAGTAGTGAGGAGGCTTTTTTGGAGGCCGTCGGCCGCCACG
ACCGGTGCCGCCACCATCCCCTGACCCACGCCCCTGACCCCTCACAAGGAGACGACCTTCCATG
ACCGAGTACAAGCCCACGGTGCGCCTCGCCACCCGCGACGACGTCCCCCGGGCCGTACGCACC
CTCGCCGCCGCGTTCGCCGACTACCCTGCAACACGCCATACAGTGGACCCTGACCGCCACATCG
AGCGGGTCACCGAGCTGCAAGAACTCTTCCTCACGCGCGTCGGGCTCGACATCGGCAAGGTGT
GGGTCGCGGACGACGGCGCCGCGGTGGCGGTCTGGACCACGCCGGAGAGCGTCGAAGCGGG
GGCGGTGTTCGCCGAGATCGGCCCGCGCATGGCCGAGTTGAGCGGTTCCCGGCTGGCCGCGC
AGCAACAGATGGAAGGCCTCCTGGCGCCGCACCGGCCCAAGGAGCCCGCGTGGTTCCTGGCCA
```

```
CCGTCGGCGTCTCGCCCGACCACCAGGGCAAGGGTCTGGGCAGCGCCGTCGTGCTCCCCGGA

GTGGAGGCGGCCGAGCGCGCCGGGGTGCCCGCCTTCCTGGAGACCTCCGCGCCCCGCAACCT

CCCCTTCTACGAGCGGCTCGGCTTCACCGTCACCGCCGACGTCGAGGTGCCCGAAGGACCGCG

CACCTGGTGCATGACCCGCAAGCCCGGTGCCTGACGCCCGCCCCACGACCCGCAGCGCCCGAC

CGAAAGGAGGGCACGACCCCATGCATCGATAAAATAAAAGATTTTATTTAGTCTCCAGAAAAGG

GGGGAATGAAAGACCCCACCTGTAGGTTTGGCAAGCTAGGCCTATTAATATTCCGGAGTATACGT

AGCCGGCTAACGTTAACAACCGGTACGATGCATTAGTTATTAATAGTAATCAATTACGGGGTCATT

AGTTCATAGCCCATATATGGAGTTCCGCGTTACATAACTTACGGTAAATGGCCCGCCTGGCTGAC

CGCCCAACGACCGCCGCCCATTGACGTCAATAATGACGTATGTTCCCATAGTAAGGCCAATAGGG

ACTTTCCATTGACGTCAATGGGTGGAGTATTTACGGTAAACTGCCCACTTGGCAGTACATCAAGT

GTATCATATGCCAAGTACGCCCCCTATTGACGTCAATGACGGTAAATGGCCCGCCTGGCATTATG

CCCAGTACATGACCTTATGGGACTTTCCTACTTGGCAGTACATCTACGTATTAGTCATCGCTATTA

CCATGGTGATGCGGTTTTGGCAGTACATCAATGGGCGTGGATAGGGGTTTGACTGAGGGGGATT

TCCAAGTCTCCACCCCATTGACGTCAATGGGAGTTTGTTTTGGCACCAAAATCAACGGGACTTTC

CAAAATGTCGTAACAACTCCGCCCCATTGACGCAAATGGGCGGTAGGCGTGTACGGTGGGAGGT

CTATATAAGCAGAGCTGGTTTAGTGAACCGTCAGATCCGCTAGCGCTACCGGACTCAGATCTCGA

GCTCAAGGTTCGAATTCTGCAGTCGACCCACCATGGCTCTTTCAAACAAGTTTATCGGAGATGAC

ATGAAAATGACCTACCATATGGATGGCTGTGTCAATGGGCATTACTTTACCGTCAAAGGTGAAGG

CAGCGGGAAGCCATACGAAGGGACGCAGACCTCGACTTTTAAAGTCACCATGGCCAACGGTGGG

CCCCTTGCATTCTCCTTTGACATACTATCTACAGTGTTCATGTATGGAAATCGATGCTTTACTGCG

TATCCTACCAGTATGCCCGACTATTTCAAACAAGCATTTCCTGACGGAATGTCATATGAAAGGACT

TTTACCTATGAAGATGGAGGAGTTGCTACAGCCAGTTGGGAAATAAGCCTTAAAGGCAACTGCTT

TGAGCACAAATCCACGTTTCATGGAGTGAACTTTCCTGCTGATGGACCTGTGATGGCGAAGATGA

CAACTGGTTGGGACCCATCTTTTGAGAAAATGACTGTCTGCGATGGAATATTGAAGGGTGATGTC

ACCGCGTTCCTCATGCTGCAAGGAGGTGGCAATTACAGATGCCAATTCCACACTTCTTACAAGAC

AAAAAAACCGGTGACGATGCCACCAAACCATGCGGTGGAACATCGCATTGCGAGGACCGACCTT

GACAAAGGTGGCAACAGTGTTCAGCTGACGGAGCACGCTGTTGCACATATAACCTCTGTTGTCCC

TTTCTAGCGGCCGCGATAATCAACCTCTGGATTACAAAATTTGTGAAAGATTGACTGGTATTCTTA

ACTATGTTGCTCCTTTTACGCTATGTGGATACGCTGCTTTAATGCCTTTGTATCATGCTATTGCTTC

CCGTATGGCTTTCATTTTCTCCTCCTTGTATAAATCCTGGTTGCTGTCTCTTTATGAGGAGTTGTG

GCCCGTTGTCAGGCAACGTGGCGTGGTGTGCACTGTGTTTGCTGACGCAACCCCCACTGGTTGG

GGCATTGCCACCACCTGTCAGCTCCTTTCCGGGACTTTCGCTTTCCCCCTCCCTATTGCCACGGC

GGAACTCATCGCCGCCTGCCTTGCCCGCTGCTGGACAGGGGCTCGGCTGTTGGGCACTGACAA

TTCCGTGGTGTTGTCGGGGAAGCTGAGGTCCTTTCCATGGCTGCTCGCCTGTGTTGCCACCTGG

ATTCTGCGCGGGACGTCCTTCTGCTACGTCCCTTCGGCCCTCAATCCAGCGGACCTTCCTTCCC

GCGGCCTGCTGCCGGCTCTGCGGCCTCTTCCGCGTCTTCGCCTTCGCCCTCAGACGAGTCGGA

TCTCCCTTTGGGCCGCCTCCCCGCATCGGACGCGTGGTACCTTTAAGACCAATGACTTACAAGG

CAGCTGTAGATCTTAGCCACTTTTTAAAAGAAAAGGGGGGACTGGAAGGGCTAATTCACTCCCAA

CGAAGACAAGATCTGCTTTTTGCTTGTACTGGGTCTCTCTGGTTAGACCAGATCTGAGCCTGGGA

GCTCTCTGGCTAACTAGGGAACCCACTGCTTAAGCCTCAATAAAGCTTGCCTTGAGTGCTTCAAG
```

-continued

```
TAGTGTGTGCCCGTCTGTTGTGTGACTCTGGTAACTAGAGATCCCTCAGACCCTTTTAGTCAGTG

TGGAAAATCTCTAGCAGTAGTAGTTCATGTCATCTTATTATTCAGTATTTATAACTTGCAAAGAAAT

GAATATCAGAGAGTGAGAGGAACTTGTTTATTGCAGCTTATAATGGTTACAAATAAAGCAATAGCA

TCACAAATTTCACAAATAAAGCATTTTTTTCACTGCATTCTAGTTGTGGTTTGTCCAAACTCATCAA

TGTATCTTATCATGTCTGGCTCTAGCTATCCCGCCCCTAACTCCGCCCATCCCGCCCCTAACTCC

GCCCAGTTCCGCCCATTCTCCGCCCCATGGCTGACTAATTTTTTTATTTATGCAGAGGCCGAGG

CCGCCTCGGCCTCTGAGCTATTCCAGAAGTAGTGAGGAGGCTTTTTTGGAGGCCTAGGGACGTA

CCCAATTCGCCCTATAGTGAGTCGTATTACGCGCGCTCACTGGCCGTCGTTTTACAACGTCGTGA

CTGGGAAAACCCTGGCGTTACCCAACTTAATCGCCTTGCAGCACATCCCCCTTTCGCCAGCTGG

CGTAATAGCGAAGAGGCCCGCACCGATCGCCCTTCCCAACAGTTGCGCAGCCTGAATGGCGAAT

GGGACGCGCCCTGTAGCGGCGCATTAAGCGCGGCGGGTGTGGTGGTTACGCGCAGCGTGACC

GCTACACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGCTTTAC

GGCACCTCGACCCCAAAAAACTTGATTAGGGTGATGGTTCACGTAGTGGGCCATCGCCCTGATA

GACGGTTTTTCGCCCTTTGACGTTGGAGTCCACGTTCTTTAATAGTGGACTCTTGTTCCAAACTGG

AACAACACTCAACCCTATCTCGGTCTATTCTTTTGATTTATAAGGGATTTTGCCGATTTCGGCCTAT

TGGTTAAAAAATGAGCTGATTTAACAAAAATTTAACGCGAATTTTAACAAAATATTAACGCTTACAA

TTTAGGTGGCACTTTTCGGGGAAATGTGCGCGGAACCCCTATTTGTTTATTTTTCTAAATACATTC

AAATATGTATCCGCTCATGAGACAATAACCCTGATAAATGCTTCAATAATATTGAAAAAGGAAGAG

TATGAGTATTCAACATTTCCGTGTCGCCCTTATTCCCTTTTTTGCGGCATTTTGCCTTCCTGTTTTT

GCTCACCCAGAAACGCTGGTGAAAGTAAAAGATGCTGAAGATCAGTTGGGTGCACGAGTGGGTT

ACATCGAACTGGATCTCAACAGCGGTAAGATCCTTGAGAGTTTTCGCCCCGAAGAACGTTTTCCA

ATGATGAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCACAGAAA

AGCATCTTACGGATGGCATGACAGTAAGAGAATTATGCAGTGCTGCCATAACCATGAGTGATAAC

ACTGCGGCCAACTTACTTCTGACAACGATCGGAGGACCGAAGGAGCTAACCGCTTTTTTGCACAA

CATGGGGGATCATGTAACTCGCCTTGATCGTTGGGAACCGGAGCTGAATGAAGCCATACCAAAC

GACGAGCGTGACACCACGATGCCTGTAGCAATGGCAACAACGTTGCGCAAACTATTAACTGGCG

AACTACTTACTCTAGCTTCCCGGCAACAATTAATAGACTGGATGGAGGCGGATAAAGTTGCAGGA

CCACTTCTGCGCTCGGCCCTTCCGGCTGGCTGGTTTATTGCTGATAAATCTGGAGCCGGTGAGC

GTGGGTCTCGCGGTATCATTGCAGCACTGGGGCCAGATGGTAAGCCCTCCCGTATCGTAGTTAT

CTACACGACGGGGAGTCAGGCAACTATGGATGAACGAAATAGACAGATCGCTGAGATAGGTGCC

TCACTGATTAAGCATTGGTAACTGTCAGACCAAGTTTACTCATATATACTTTAGATTGATTTAAAAC

TTCATTTTTAATTTAAAAGGATCTAGGTGAAGATCCTTTTTGATAATCTCATGACCAAAATCCCTTA

ACGTGAGTTTTCGTTCCACTGAGCGTCAGACCCCGTAGAAAAGATCAAAGGATCTTCTTGAGATC

CTTTTTTTCTGCGCGTAATCTGCTGCTTGCAAACAAAAAAACCACCGCTACCAGCGGTGGTTTGTT

TGCCGGATCAAGAGCTACCAACTCTTTTTCCGAAGGTAACTGGCTTCAGCAGAGCGCAGATACCA

AATACTGTTCTTCTAGTGTAGCCGTAGTTAGGCCACCACTTCAAGAACTCTGTAGCACCGCCTAC

ATACCTCGCTCTGCTAATCCTGTTACCAGTGGCTGCTGCCAGTGGCGATAAGTCGTGTCTTACCG

GGTTGGACTCAAGACGATAGTTACCGGATAAGGCGCAGCGGTCGGGCTGAACGGGGGGTTCGT

GCACACAGCCCAGCTTGGAGGGAACGACCTACACCGAACTGAGATACCTACAGCGTGAGCTATG
```

```
AGAAAGCGCCACGCTTCCCGAAGGGAGAAAGGCGGACAGGTATCCGGTAAGCGGCAGGGTCGG

AACAGGAGAGCGCACGAGGGAGCTTCCAGGGGGAAACGCCTGGTATCTTTATAGTCCTGTCGGG

TTTCGCCACCTCTGACTTGAGCGTCGATTTTTGTGATGCTCGTCAGGGGGGCGGAGCCTATGGA

AAAACGCCAGCAACGCGGCCTTTTTACGGTTCCTGGCCTTTTGCTGGCCTTTTGCTCACATGTTC

TTTCCTGCGTTATCCCCTGATTCTGTGGATAACCGTATTACCGCCTTTGAGTGAGCTGATACCGCT

CGCCGCAGCCGAACGACCGAGCGCAGCGAGTCAGTGAGCGAGGAAGCGGAAGAGCGCCCAAT

ACGCAAACCGCCTCTCCCCGCGCGTTGGCCGATTCATTAATGCAGCTGGCACGACAGGTTTCCC

GACTGGAAAGCGGGCAGTGAGCGCAACGCAATTAATGTGAGTTAGCTCACTCATTAGGCACCCC

AGGCTTTACACTTTATGCTTCCGGCTCGTATGTTGTGTGGAATTGTGAGCGGATAACAATTTCACA

CAGGAAACAGCTATGACCATGATTACGCCAAGCGCGCAATTAACCCTCACTAAAGGGAACAAAAG

CTGGAGCTGCAAGCTT pSSI12112 (SEQ ID NO: 3):
AATGTAGTCTTATGCAATACTCTTGTAGTCTTGCAACATGGTAACGATGAGTTAGCAACATGCCTT

ACAAGGAGAGAAAAAGCACCGTGCATGCCGATTGGTGGAAGTAAGGTGGTACGATCGTGCCTTA

TTAGGAAGGCAACAGACGGGTCTGACATGGATTGGACGAACCACTGAATTGCCGCATTGCAGAG

ATATTGTATTTAAGTGCCTAGCTCGATACATAAACGGGTCTCTCTGGTTAGACCAGATCTGAGCCT

GGGAGCTCTCTGGCTAACTAGGGAACCCACTGCTTAAGCCTCAATAAAGCTTGCCTTGAGTGCTT

CAAGTAGTGTGTGCCCGTCTGTTGTGTGACTCTGGTAACTAGAGATCCCTCAGACCCTTTTAGTC

AGTGTGGAAAATCTCTAGCAGTGGCGCCCGAACAGGGACTTGAAAGCGAAAGGGAAACCAGAGG

AGCTCTCTCGACGCAGGACTCGGCTTGCTGAAGCGCGCACGGCAAGAGGCGAGGGGCGGCGA

CTGGTGAGTACGCCAAAAATTTTGACTAGCGGAGGCTAGAAGGAGAGAGATGGGTGCGAGAGCG

TCAGTATTAAGCGGGGGAGAATTAGATCGCGATGGGAAAAAATTCGGTTAAGGCCAGGGGGAAA

GAAAAAATATAAATTAAAACATATAGTATGGGCAAGCAGGGAGCTAGAACGATTCGCAGTTAATCC

TGGCCTGTTAGAAACATCAGAAGGCTGTAGACAAATACTGGGACAGCTACAACCATCCCTTCAGA

CAGGATCAGAAGAACTTAGATCATTATATAATACAGTAGCAACCCTCTATTGTGTGCATCAAAGGA

TAGAGATAAAAGACACCAAGGAAGCTTTAGACAAGATAGAGGAAGAGCAAAACAAAAGTAAGACC

ACCGCACAGCAAGCGGCCGCTGATCTTCAGACCTGGAGGAGGAGATATGAGGGACAATTGGAG

AAGTGAATTATATAAATATAAAGTAGTAAAAATTGAACCATTAGGAGTAGCACCCACCAAGGCAAA

GAGAAGAGTGGTGCAGAGAGAAAAAAGAGCAGTGGGAATAGGAGCTTTGTTCCTTGGGTTCTTG

GGAGCAGCAGGAAGCACTATGGGCGCAGCGTCAATGACGCTGACGGTACAGGCCAGACAATTAT

TGTCTGGTATAGTGCAGCAGCAGAACAATTTGCTGAGGGCTATTGAGGCGCAACAGCATCTGTTG

CAACTCACAGTCTGGGGCATCAAGCAGCTCCAGGCAAGAATCCTGGCTGTGGAAAGATACCTAA

AGGATCAACAGCTCCTGGGGATTTGGGGTTGCTCTGGAAAACTCATTTGCACCACTGCTGTGCCT

TGGAATGCTAGTTGGAGTAATAAATCTCTGGAACAGATTTGGAATCACACGACCTGGATGGAGTG

GGACAGAGAAATTAACAATTACACAAGCTTAATACACTCCTTAATTGAAGAATCGCAAAACCAGCA

AGAAAAGAATGAACAAGAATTATTGGAATTAGATAAATGGGCAAGTTTGTGGAATTGGTTTAACAT

AACAAATTGGCTGTGGTATATAAAATTATTCATAATGATAGTAGGAGGCTTGGTAGGTTTAAGAAT

AGTTTTTGCTGTACTTTCTATAGTGAATAGAGTTAGGCAGGGATATTCACCATTATCGTTTCAGAC

CCACCTCCCAACCCCGAGGGGACCCGAGAGGCCCGAAGGAATAGAAGAAGAAGGTGGAGAGAG

AGACAGAGACAGATCCATTCGATTAGTGAACGGATCTCGACGGTATCGATACTAGTAATTTTTCTG

CAGAAAACGTACCCGGGGATCCTCTAGGATCCCACCGAAAGGTTGCTCCTTAACACAGGCTAAG
```

```
GACCAGCTTCTTTGGGAGAGAACAGACGCAGGGGCGGGAGGGAAAAAGGGAGAGGCAGACGTC

ACTTCCCCTTGGCGGCTCTGGCAGCAGATTGGTCGGTTGAGTGGCAGAAAGGCAGACGGGGAC

TGGGCAAGGCACTGTCGGTGACATCACGGACAGGGCGACTTCTATGTAGATGAGGCAGCGCAG

AGGCTGCTGCTTCGCCACTTGCTGCTTCGCCACGAAGGAGTTCCCGTGCCCTGGGAGCGGGTTC

AGGACCGCGGATCGGAAGTGAGAATCCCAGCTGTGTGTCAGGGCTGGAAAGGGCTCGGGAGTG

CGCGGGGCAAGTGACCGTGTGTGTAAAGAGTGAGGCGTATGAGGCTGTGTCGGGGCAGAGCCC

GAAGATCCGGGTTGCGGAGGGTGGGCCTGGGAGGGGTGGTGGCCATTTTTTGTCTAACCCTAAC

TGAGAAGGGCGTAGGCGCCGTGCTTTTGCTCCCCGCGCGCTGTTTTTCTCGCTGACTTTCAGCG

GGCGGAAAAGCCTCGGCCTGCCGCCTTCCACCGTTCATTCTAGAGCAAACAAAAAATGTCAGCT

GCTGGCCCGTTCGCCCCTCCCGGGGACCTGCGGCGGGTCGCCTGCCCAGCCCCCGAACCCCG

CCTGGAGGCCGCGGTCGGCCCGGGGCTTCTCCGGAGGCACCCACTGCCACCGCGAAGAGTTG

GGCTCTGTCAGCCGCGGGTCTCTCGGGGGCGAGGGCGAGGTTCAGGCCTTTCAGGCCGCAGG

AAGAGGAACGGAGCGAGTCCCCGCGCGCGGCGCGATTCCCTGAGCTGTGGGACGTGCACCCA

GGACTCGGCTCACACATGCAGTTCGCTTTCCTGTTGGTGGGGGAACGCCGATCGTGCGCATCC

GTCACCCCTCGCCGGCAATGGGGGCTTGTGAACCCCCAAACCTGACTGACTGGGCCAGTGTGCT

GCAAATTGGCAGGAGACGTGAAGGCACCTCCAAAGTCGACTTTCTGGAGTTTCAAAAACAGACC

GTACATGTCCGCGGTCGCGACGTACCTACCGGGTAGGGGAGGCGCTTTTCCCAAGGCAGTCTG

GAGCATGCGCTTTAGCAGCCCCGCTGGGCACTTGGCGCTACACAAGTGGCCTCTGGCCTCGCA

CACATTCCACATCCACCGGTAGGCGCCAACCGGCTCCGTTCTTTGGTGGCCCCTTCGCGCCACC

TTCTACTCCTCCCCTAGTCAGGAAGTTCCCCCCCGCCCCGCAGCTCGCGTCGTGCAGGACGTGA

CAAATGGAAGTAGCACGTCTCACTAGTCTCGTGCAGATGGACAGCACCGCTGAGCAATGGAAGC

GGGTAGGCCTTTGGGGCAGCGGCCAATAGCAGCTTTGCTCCTTCGCTTTCTGGGCTCAGAGGCT

GGGAAGGGGTGGGTCCGGGGCGGGCTCAGGGGCGGGCTCAGGGGCGGGGCGGGCGCCCG

AAGTCCTCCGGAGGCCCGGCATTCTGCACGCTTCAAAAGCGCACGTCTGCCGCGCTGTTCTCCT

CTTCCTCATCTCCGGGCCTTTCGACTCTAGACACGTGTTGACAATTAATCATCGGCATAGTATATC

GGCATAGTATAATACGAGAAGGTGAGGAACTAAACCATGGCCAAGCCTTTGTCTCAAGAAGAATC

CACCCTCATTGAAAGAGCAACGGCTACAATCAACAGCATCCCCATCTCTGAAGACTACAGCGTCG

CCAGCGCAGCTCTCTCTAGCGACGGCCGCATCTTCACTGGTGTCAATGTATATCATTTTACTGGG

GGACCTTGTGCAGAACTCGTGGTGCTGGGCACTGCTGCTGCTGCGGCAGCTGGCAACCTGACTT

GTATCGTCGCGATCGGAAATGAGAAGAGGGGCATCTTGAGGCCCTGCGGAGGGTGCCGAGAGG

TGCTTCTCGATCTGCATCCTGGGATCAAAGCCATAGTGAAGGACAGTGATGGACAGCCGACGGC

AGTTGGGATTCGTGAATTGCTGCCCTCTGGTTATGTGTGGGAGGGCTAAGCACAATTCGAGCTC

GGTACGCGTATCGATGGCGCCAGCTGCAGGCGGCCGCCATATGCATCCTAGGCCTATTAATATT

CCGGAGTATACGTAGGCGGCTAACGTTAACAACCGGTACGATGCATTAGTTATTAATAGTAATCAA

TTACGGGGTCATTAGTTCATAGCCCATATATGGAGTTCCGCGTTACATAACTTACGGTAAATGGCC

CGCCTGGCTGACCGCCCAACGACCCCCGCCCATTGACGTCAATAATGACGTATGTTCCCATAGT

AACGCCAATAGGGACTTTCCATTGACGTCAATGGGTGGAGTATTTACGGTAAACTGCCCACTTGG

CAGTACATCAAGTGTATCATATGCCAAGTACGCCGCCTATTGAGGTCAATGAGGGTAAATGGCCC

GCCTGGCATTATGCCCAGTACATGACCTTATGGGACTTTCCTACTTGGCAGTACATCTACGTATTA

GTCATCGCTATTACCATGGTGATGCGGTTTTGGCAGTACATCAATGGGCGTGGATAGCGGTTTGA
```

-continued

```
CTCACGGGGATTTCCAAGTCTCCACCCCATTGACGTCAATGGGAGTTTGTTTTGGCACCAAAATC
AACGGGACTTTCCAAAATGTCGTAACAACTCCGCCCCATTGACGCAAATGGGCGGTAGGCGTGT
ACGGTGGGAGGTCTATATAAGCAGAGCTGGTTTAGTGAACCGTCAGATCCGCTAGCCCCACCAT
GCCGCGCGCTCCCCGCTGCCGAGCCGTGCGCTCCCTGCTGCGCAGCCACTACCGCGAGGTGCT
GCCGCTGGCCACGTTCGTGCGGCGCCTGGGGCCCCAGGGCTGGCGGCTGGTGCAGCGCGGG
GACCCGGCGGCTTTCCGCGCGCTGGTGGCCCAGTGCCTGGTGTGCGTGCCCTGGGACGCACG
GCCGCCCCCGCCGCCCCTCCTTCCGCCAGGTGTCCTGCCTGAAGGAGCTGGTGGCCCGAGT
GCTGCAGAGGCTGTGCGAGCGCGGCGCGAAGAACGTGCTGGCCTTCGGCTTCGCGCTGCTGGA
CGGGGCCCGCGGGGGCCCCCCCGAGGCCTTCACCACCAGCGTGCGCAGCTACCTGCCCAACA
CGGTGACCGACGCACTGCGGGGGAGCGGGGCGTGGGGGCTGCTGTTGCGCCGCGTGGGCGA
CGACGTGCTGGTTCACCTGCTGGCACGCTGCGCGCTCTTTGTGCTGGTGGCTCCCAGCTGCGC
CTACCAGGTGTGCGGGCCGCCGCTGTACCAGCTCGGCGCTGCCACTCAGGCCCGGCCCCCGC
CACACGCTAGTGGACCCCGAAGGCGTCTGGGATGCGAACGGGCCTGGAACCATAGCGTCAGGG
AGGCCGGGGTCCCCCTGGGCCTGCCAGCCCCGGGTGCGAGGAGGCGCGGGGGCAGTGCCAG
CCGAAGTCTGCCGTTGCCCAAGAGGCCGAGGCGTGGCGCTGCCGCTGAGGCGGAGGGGAGGC
CCGTTGGGCAGGGGTCCTGGGCCCACCCGGGCAGGACGCGTGGACCGAGTGACCGTGGTTTCT
GTGTGGTGTCACCTGCCAGACCCGCCGAAGAAGCCACCTCTTTGGAGGGTGCGCTCTCTGGCAC
GCGCCACTCCCACCCATCCGTGGGCCGCCAGCACCACGCGGGCCCCCCATCCACATCGCGGCC
ACCACGTCCCTGGGACACGCCTTGTCCCCCGGTGTACGCCGAGACCAAGCACTTCCTCTACTCC
TCAGGCGACAAGGAGCAGCTGCGGCCCTCCTTCCTACTCAGCTCTCTGAGGCCCAGCCTGACTG
GCGCTCGGAGGCTCGTGGAGACCATCTTTCTGGGTTCCAGGCCCTGGATGCCAGGGACTCCCC
GCAGGTTGCCCCGCCTGCCCCAGGGCTACTGGCAAATGCGGCCGCTGTTTCTGGAGCTGCTTG
GGAACCACGCGCAGTGCCCCTACGGGGTGCTCCTCAAGACGCACTGCCCGCTGCGAGCTGCGG
TCACCCCAGCAGCCGGTGTCTGTGCCCGGGAGAAGCCCCAGGGCTCTGTGGCGGCCCCGAG
GAGGAGGACACAGACCCCCGTCGCCTGGTGCAGCTGCTCCGCCAGCACAGCAGCCCCTGGCAG
GTGTAGGGCTTCGTGCGGGCCTGCCTGCGCCGGCTGGTGCCGCCAGGCCTCTGGGGCTCCAG
GCACAACGAACGCCGCTTCCTCAGGAACACCAAGAAGTTCATCTCCCTGGGGAAGCATGCCAAG
CTCTCGCTGCAGGAGCTGACGTGGAAGATGAGCGTGCGGGGCTGCGCTTGGCTGCGCAGGAGC
CCAGGGGTTGGCTGTGTTCCGGCCGCAGAGCACCGTCTGCGTGAGGAGATCCTGGCCAAGTTC
CTGCACTGGCTGATGAGTGTGTACGTCGTCGAGCTGCTGAGGTCTTTCTTTTATGTCAGGGAGAG
CACGTTTCAAAAGAACAGGCTCTTTTTCTACCGGAAGAGTGTCTGGAGCAAGTTGCAAAGCATTG
GAATCAGACAGCACTTGAAGAGGGTGCAGCTGCGGGAGCTGTCGGAAGCAGAGGTCAGGCAGC
ATCGGGAAGCCAGGCCCGCCCTGCTGACGTCCAGACTCCGCTTCATCCCCAAGCCTGACGGGC
TGCGGCCGATTGTGAACATGGACTACGTCGTGGGAGCCAGAACGTTCCGCAGAGAAAAGAGGG
CCGAGCGTCTCACCTCCAGGGTGAAGGCACTGTTCAGCGTGCTCAACTACGAGCGGGCGCGGC
GCCCCGGCCTCCTGGGCGCCTCTGTGCTGGGCCTGGACGATATCCACAGGGCCTGGCGCACCT
TCGTGCTGCGTGTGCGGGCCCAGGACCCGCCGCCTGAGCTGTACTTTGTCAAGGTGGATGTGA
CGGGCGCGTACGACACCATCCCCCAGGACAGGCTCACGGAGGTCATCGCCAGCATCATCAAAC
CCCAGAACACGTACTGCGTGCGTCGGTATGCCGTGGTCCAGAAGGCCGCCCATGGGCACGTCC
GCAAGGCCTTCAAGAGCCACGTCTCTACCTTGACAGACCTCCAGCCGTACATGCGACAGTTCGT
GGCTCACCTGCAGGAGACCAGCCCGCTGAGGGATGCCGTCGTCATCGAGCAGAGCTCCTCCCT
```

```
GAATGAGGCCAGCAGTGGCCTCTTCGACGTCTTCCTACGCTTCATGTGCCACCACGCCGTGCGC
ATCAGGGGCAAGTCCTACGTCCAGTGCCAGGGGATCCCGCAGGGCTCCATCCTCTCCACGCTG
CTCTGCAGCCTGTGCTACGGCGACATGGAGAACAAGCTGTTTGCGGGGATTCGGCGGGACGGG
CTGCTCCTGCGTTTGGTGGATGATTTCTTGTTGGTGACACCTCACCTCACCCACGCGAAAACCTT
CCTCAGGACCCTGGTCCGAGGTGTCCCTGAGTATGGCTGCGTGGTGAACTTGCGGAAGACAGTG
GTGAACTTCCCTGTAGAAGAGGAGGCCCTGGGTGGCAGGGCTTTTGTTGAGATGCCGGCCCAGG
GCCTATTCCCCTGGTGCGGCCTGCTGCTGGATACCCGGACCCTGGAGGTGCAGAGCGACTACT
CCAGCTATGCCCGGACCTCCATCAGAGCCAGTCTCACCTTCAACCGCGGCTTCAAGGCTGGGAG
GAACATGCGTCGCAAACTCTTTGGGGTCTTGCGGCTGAAGTGTCACAGCCTGTTTCTGGATTTGC
AGGTGAAGAGCCTCCAGAGGGTGTGCACCAACATCTACAAGATCCTCCTGCTGCAGGCGTACAG
GTTTCACGCATGTGTGCTGCAGCTCCCATTTCATCAGCAAGTTTGGAAGAACCCCACATTTTTCCT
GCGCGTCATCTCTGACACGGCCTCCCTCTGCTACTCCATCCTGAAAGCCAAGAACGCAGGGATG
TCGCTGGGGGCCAAGGGCGCCGCCGGCCCTCTGCCCTCCGAGGCCGTGCAGTGGCTGTGCCA
CCAAGCATTCCTGCTCAAGCTGACTCGACACCGTGTCACCTACGTGCCACTCCTGGGGTCACTC
AGGACAGCCCAGACGCAGCTGAGTCGGAAGCTCCCGGGGACGACGCTGACTGCCCTGGAGGC
CGCAGCCAACCCGGCACTGCCCTCAGACTTCAAGACCATCCTGGACTGAGTCGAAACTCGCGGC
CGCATGCGTCGACGCGTATCGATGCATCTTAAGTAGATGTACCTTTAAGACCAATGACTTACAAG
GCAGCTGTAGATCTTAGCCACTTTTTAAAAGAAAAGGGGGGACTGGAAGGGCTAATTCACTCCCA
ACGAAGACAAGATCTGCTTTTTGCTTGTACTGGGTCTCTCTGGTTAGACCAGATCTGAGCCTGGG
AGCTCTCTGGCTAACTAGGGAACCCACTGCTTAAGCCTCAATAAAGCTTGCCTTGAGTGCTTCAA
GTAGTGTGTGCCCGTCTGTTGTGTGACTCTGGTAACTAGAGATCCCTCAGACCCTTTTAGTCAGT
GTGGAAAATCTCTAGCAGTAGTAGTTCATGTCATCTTATTATTCAGTATTTATAACTTGCAAAGAAA
TGAATATCAGAGAGTGAGAGGAACTTGTTTATTGCAGCTTATAATGGTTACAAATAAAGCAATAGC
ATCACAAATTTCACAAATAAAGCATTTTTTTCACTGCATTCTAGTTGTGGTTTGTCCAAACTCATCA
ATGTATCTTATCATGTCTGGCTCTAGCTATCCCGCCCCTAACTCCGCCCATCCCGCCCCTAACTC
CGCCCAGTTCCGCCCATTCTCCGCCCCATGGCTGACTAATTTTTTTTATTTATGCAGAGGCCGAG
GCCGCCTCGGCCTCTGAGCTATTCCAGAAGTAGTGAGGAGGCTTTTTTGGAGGCCTAGGGACGT
ACCCAATTCGCCCTATAGTGAGTCGTATTACGCGCGCTCACTGGCCGTCGTTTTACAACGTCGTG
ACTGGGAAAACCCTGGCGTTACCCAACTTAATCGCCTTGCAGCACATCCCCCTTTCGCCAGCTGG
CGTAATAGCGAAGAGGCCCGCACCGATCGCCCTTCCCAACAGTTGCGCAGCCTGAATGGCGAAT
GGGACGCGCCCTGTAGCGGCGCATTAAGCGCGGCGGGTGTGGTGGTTACGCGCAGCGTGACC
GCTACACTTGCCAGCGCCCTAGCGCCCGCTCCTTTCGCTTTCTTCCCTTCCTTTCTCGCCACGTT
CGCCGGCTTTCCCCGTCAAGCTCTAAATCGGGGGCTCCCTTTAGGGTTCCGATTTAGTGCTTTAC
GGCACCTCGACCCCAAAAAACTTGATTAGGGTGATGGTTCACGTAGTGGGCCATCGCCCTGATA
GACGGTTTTTCGCCCTTTGACGTTGGAGTCCACGTTCTTTAATAGTGGACTCTTGTTCCAAACTGG
AACAACACTCAACCCTATCTCGGTCTATTCTTTTGATTTATAAGGGATTTTGCCGATTTCGGCCTAT
TGGTTAAAAAATGAGCTGATTTAACAAAAATTTAACGCGAATTTTAACAAAATATTAACGCTTACAA
TTTAGGTGGCACTTTTCGGGGAAATGTGCGCGGAACCCCTATTTGTTTATTTTTCTAAATACATTC
AAATATGTATCCGCTCATGAGACAATAACCCTGATAAATGCTTCAATAATATTGAAAAAGGAAGAG
TATGAGTATTCAACATTTCCGTGTCGCCCTTATTCCCTTTTTTGCGGCATTTTGCCTTCCTGTTTTT
```

-continued
```
GCTCACCCAGAAACGCTGGTGAAAGTAAAAGATGCTGAAGATCAGTTGGGTGCACGAGTGGGTT

ACATCGAACTGGATCTCAACAGCGGTAAGATCCTTGAGAGTTTTCGCCCCGAAGAACGTTTTCCA

ATGATGAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCACAGAAA

AGCATCTTACGGATGGCATGACAGTAAGAGAATTATGCAGTGCTGCCATAACCATGAGTGATAAC

ACTGCGGCCAACTTACTTCTGACAACGATCGGAGGACCGAAGGAGCTAACCGCTTTTTTGCACAA

CATGGGGATCATGTAACTCGCCTTGATCGTTGGGAACCGGAGCTGAATGAAGCCATACCAAAC

GACGAGCGTGACACCACGATGCCTGTAGCAATGGCAACAACGTTGCGCAAACTATTAACTGGCG

AACTACTTACTCTAGCTTCCCGGCAACAATTAATAGACTGGATGGAGGCGGATAAAGTTGCAGGA

CCACTTCTGCGCTCGGCCCTTCCGGCTGGCTGGTTTATTGCTGATAAATCTGGAGCCGGTGAGC

GTGGGTCTCGCGGTATCATTGCAGCACTGGGGCCAGATGGTAAGCCCTCCCGTATCGTAGTTAT

CTACACGACGGGGAGTCAGGCAACTATGGATGAACGAAATAGACAGATCGCTGAGATAGGTGCC

TCACTGATTAAGCATTGGTAACTGTCAGACCAAGTTTACTCATATATACTTTAGATTGATTTAAAAC

TTCATTTTTAATTTAAAAGGATCTAGGTGAAGATCCTTTTTGATAATCTCATGACCAAAATCCCTTA

ACGTGAGTTTTCGTTCCACTGAGCGTCAGACCCCGTAGAAAAGATCAAAGGATCTTCTTGAGATC

CTTTTTTTCTGCGCGTAATCTGCTGCTTGCAAACAAAAAAACCACCGCTACCAGCGGTGGTTTGTT

TGCCGGATCAAGAGCTACCAACTCTTTTTCCGAAGGTAACTGGCTTCAGCAGAGCGCAGATACCA

AATACTGTTCTTCTAGTGTAGCCGTAGTTAGGCCACCACTTCAAGAACTCTGTAGCACCGCCTAC

ATACCTCGCTCTGCTAATCCTGTTACCAGTGGCTGCTGCCAGTGGCGATAAGTCGTGTCTTACCG

GGTTGGACTCAAGACGATAGTTACCGGATAAGGCGCAGCGGTCGGGCTGAACGGGGGGTTCGT

GCACACAGCCCAGCTTGGAGGGAACGACCTACACCGAACTGAGATACCTACAGCGTGAGCTATG

AGAAAGCGCCACGCTTCCCGAAGGGAGAAAGGCGGACAGGTATCCGGTAAGCGGCAGGGTCGG

AACAGGAGAGCGCACGAGGGAGCTTCCAGGGGGAAACGCCTGGTATCTTTATAGTCCTGTCGGG

TTTCGCCACCTCTGACTTGAGCGTCGATTTTTGTGATGCTCGTCAGGGGGCGGAGCCTATGGA

AAAACGCCAGCAACGCGGCCTTTTTACGGTTCCTGGCCTTTTGCTGGCCTTTTGCTCACATGTTC

TTTCCTGCGTTATCCCCTGATTCTGTGGATAACCGTATTACCGCCTTTGAGTGAGCTGATACCGCT

CGCCGCAGCCGAACGACCGAGCGCAGCGAGTCAGTGAGCGAGGAAGCGGAAGAGCGCCCAAT

ACGCAAACCGCCTCTCCCCGCGCGTTGGCCGATTCATTAATGCAGCTGGCACGACAGGTTTCCC

GACTGGAAAGCGGGCAGTGAGCGCAACGCAATTAATGTGAGTTAGCTCACTCATTAGGCACCCC

AGGCTTTACACTTTATGCTTCCGGCTCGTATGTTGTGTGGAATTGTGAGCGGATAACAATTTCACA

CAGGAAACAGCTATGACCATGATTACGCCAAGCGCGCAATTAACCCTCACTAAAGGGAACAAAAG

CTGGAGCTGCAAGCTT
```

Although the foregoing invention has been described in some detail by way of Illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention,

What is claimed is:

1. A method of treating loss of memory in a mammalian subject, the method comprising: administering to the subject a lentiviral based nucleic acid vector comprising a coding sequence for telomerase RNA (TR) or telomerase reverse transcriptase (TERT) to treat the mammalian subject for loss of memory.

2. The method of claim 1, wherein the vector comprises a coding sequence for telomerase RNA (TR).

3. The method of claim 2, wherein telomerase RNA (TR) is human TR, or an active fragment or functional equivalent thereof.

4. The method of claim 1, wherein the vector comprises a coding sequence for telomerase reverse transcriptase (TERT).

5. The method of claim 4, wherein TERT is human TERT.

6. The method of claim 1, wherein the method is a gene therapy method.

7. The method of claim 1, wherein the nucleic acid sequence encoding TR or TERT is operably linked to a regulatory sequence that drives expression of the coding sequence.

8. The method of claim 1, wherein the vector is a non-integrative vector.

9. The method of claim 1, wherein the mammalian subject is an adult mammal.

10. The method of claim 9, wherein the adult mammal is an adult human.

11. The method of claim 9, wherein the adult mammal is an animal.

12. A method of treating loss of memory in a mammalian subject, the method comprising: administering to the subject an adeno-associated virus-based vector comprising a coding sequence for telomerase reverse transcriptase (TERT) to treat the mammalian subject for loss of memory.

13. The method of claim 12, wherein TERT is human TERT.

14. The method of claim 12, wherein the nucleic acid sequence encoding TERT is operably linked to a regulatory sequence that drives expression of the coding sequence.

15. The method of claim 14, wherein the regulatory sequence comprises the cytomegalovirus (CMV) promoter.

16. The method of claim 12, wherein the mammalian subject is an adult human.

17. The method of claim 12, wherein the vector is represented by the formula:

left inverted terminal repeat (LITR)-cytomegalovirus promoter (CMV)-telomerase reverse transcriptase coding sequence (TERT)-SV40 poly-adenylation signal (SV40pA)-right inverted terminal repeat (RITR).

18. The method of claim 17, wherein the vector is an AAV6 vector.

19. The method of claim 17, wherein the vector is an AAV8 vector.

20. The method of claim 17, wherein the vector is an AAV9 vector.

* * * * *